United States Patent
Soula et al.

[11] Patent Number: 6,133,199
[45] Date of Patent: Oct. 17, 2000

[54] PROCESS AND COMPOSITIONS PROMOTING BIOLOGICAL EFFECTIVENESS OF EXOGENOUS CHEMICAL SUBSTANCES IN PLANTS

[75] Inventors: Gérard G. Soula, Meyzieux; Rémi Meyrueix, Lyons; Alain J. L. Lemercier, St Bonnet de Mure; Nathan J. Bryson, Millery; Olivier Soula, Lyons, all of France; Anthony J. I. Ward, Clayton, Mo.; Jane L. Gillespie, St. Louis, Mo.; Ronald J. Brinker, Ellisville, Mo.

[73] Assignee: Monsanto Company, Saint Louis, Mo.

[21] Appl. No.: 09/124,318

[22] Filed: Jul. 29, 1998

Related U.S. Application Data

[60] Provisional application No. 60/082,974, Apr. 24, 1998, and provisional application No. 60/083,005, Apr. 24, 1998.

[30] Foreign Application Priority Data

Jul. 30, 1997 [FR] France .................................. 97-09983

[51] Int. Cl.$^7$ .................................................. A01N 25/30
[52] U.S. Cl. .................................. 504/206; 504/365
[58] Field of Search ........................... 504/206, 365

[56] References Cited

U.S. PATENT DOCUMENTS

| | | | |
|---|---|---|---|
| 3,799,758 | 3/1974 | Franz | 71/86 |
| 3,853,530 | 12/1974 | Franz | 71/76 |
| 4,140,513 | 2/1979 | Prill | 71/86 |
| 4,315,765 | 2/1982 | Large | 71/87 |

(List continued on next page.)

FOREIGN PATENT DOCUMENTS

| | | | |
|---|---|---|---|
| 57565/90 | 1/1991 | Australia | A01N 57/20 |
| 0 124 351 | 11/1984 | European Pat. Off. | C07F 9/38 |
| 0 148 169 | 10/1987 | European Pat. Off. | B01J 13/02 |
| 0 379 852 | 8/1990 | European Pat. Off. | A01N 57/20 |

(List continued on next page.)

OTHER PUBLICATIONS

Bakel. Chemical Abstracts, 105:97688c. Abstract of IN 156,233, Jun. 1985.

Wyrill & Burnside, *Weed Science* 25,275–287 (1977).

*Primary Examiner*—S. Mark Clardy
*Attorney, Agent, or Firm*—James C. Forbes

[57] ABSTRACT

A plant treatment composition for application of an anionic exogenous chemical substance such as glyphosate herbicide to foliage of a plant is provided. The composition is a colloidal dispersion having supramolecular aggregates dispersed in an aqueous application medium. The supramolecular aggregates comprise one or more amphiphilic salt(s) having anions of the exogenous chemical substance and cations derived by protonation of one or more polyamine(s) or polyamine derivative(s) each having (a) at least two nitrogen-containing groups, of which a number n not less than 1 are amino groups that can be protonated to form cationic primary, secondary or tertiary ammonium groups, and (b) at least one hydrocarbyl or acyl group having about 6 to about 30 carbon atoms. The composition contains (i) a molar amount X in total of the exogenous chemical substance, in all salt and acid forms thereof present, sufficient to elicit a biological response when the composition is applied to the foliage of the plant at a rate of about 10 to about 1000 l/ha, (ii) a molar amount A in total of said polyamine(s) and derivative(s) thereof and cations derived therefrom, and (iii) a zero or molar amount B in total of one or more monovalent base(s) and cations derived therefrom, said base(s) being other than a polyamine or derivative thereof, such that $nA/(nA+B)$ is about 0.01 to 1, and $(nA+B)/X$ is about 0.5 to about 10.

Also provided are a liquid concentrate composition which, upon dilution with water, forms a plant treatment composition as described above, and a process for making such a liquid concentrate composition. Plant treatment compositions of the invention are useful for eliciting a biological activity, for example herbicidal activity, in a plant when applied to foliage thereof.

39 Claims, 1 Drawing Sheet

U.S. PATENT DOCUMENTS

| | | | |
|---|---|---|---|
| 4,431,594 | 2/1984 | Broadhurst et al. | 260/502.5 F |
| 4,481,026 | 11/1984 | Prisbylla | 71/86 |
| 4,507,250 | 3/1985 | Bakel | 260/502.5 F |
| 4,853,026 | 8/1989 | Frisch et al. | 71/86 |
| 5,248,086 | 9/1993 | Waldrum et al. | 239/10 |
| 5,389,680 | 2/1995 | Ruminski | 514/563 |
| 5,464,807 | 11/1995 | Claude et al. | 504/206 |
| 5,668,085 | 9/1997 | Forbes et al. | 504/206 |
| 4,405,531 | 9/1983 | Franz | 260/501.12 |

FOREIGN PATENT DOCUMENTS

| | | | |
|---|---|---|---|
| 2 648 316 | 12/1990 | France | A01N 25/30 |
| WO 83/03608 | 10/1983 | WIPO | C07F 9/28 |
| WO 96/32839 | 10/1996 | WIPO . | |
| WO 98/06259 | 2/1998 | WIPO | A01N 25/00 |
| 0 485 207 | 5/1992 | European Pat. Off. | A01N 25/04 |

PROCESS AND COMPOSITIONS PROMOTING BIOLOGICAL EFFECTIVENESS OF EXOGENOUS CHEMICAL SUBSTANCES IN PLANTS

This application claims the benefit of French patent application number 97-09983 filed Jul. 30, 1997, U.S. provisional patent application Ser. No. 60/082,974 filed Apr. 24, 1998, and U.S. provisional patent application Ser. No. 60/083,005 filed Apr. 24, 1998.

FIELD OF THE INVENTION

The field of the present invention is that of exogenous chemical substances applied to foliage of plants, and relates particularly to a process and to compositions applied by that process for promoting biological effectiveness of such exogenous chemical substances.

The term "exogenous chemical substance" as used herein means a chemical substance, whether naturally or synthetically obtained, which is applied to a plant to result in expressing a desired biological activity. The term "biological activity" as used herein means elicitation of a stimulatory, inhibitory, regulatory, therapeutic, toxic or lethal response in the plant or in a pathogen, parasite or feeding organism present in or on the plant. Examples of exogenous chemical substances include, but are not limited to, chemical pesticides (such as herbicides, algicides, fungicides, bactericides, viricides, insecticides, miticides, nematicides and molluscicides), plant growth regulators, fertilizers and nutrients, gametocides, defoliants, desiccants, mixtures thereof and the like.

The term "biological effectiveness" is used herein to denote the degree to which a desired biological activity is expressed upon application of an exogenous chemical substance to foliage of a plant, or alternatively to denote the dosage or rate of application of the exogenous chemical substance that results in the desired biological activity being expressed to a given degree. For example, where the exogenous chemical substance is a herbicide, biological effectiveness can be measured by the degree of inhibition of plant growth resulting from application of a particular rate of the herbicide, or by the application rate of the herbicide required to cause a particular degree of inhibition, e.g., 50% or 85% inhibition. Thus increased or enhanced biological effectiveness of a herbicide can be exhibited for example as an increased level of plant growth inhibition at a given rate of the herbicide, or as a reduction in the minimum rate of the herbicide giving a certain threshold level of plant growth inhibition.

BACKGROUND OF THE INVENTION

For many purposes in agriculture and related endeavors it is desired to treat plants with exogenous chemical substances of various kinds. Many exogenous chemical substances are applied to foliage (i.e., leaves and other non-woody above-ground parts) of a plant, and have a site of action in the plant either close to or remote from the locus of application. Such substances are referred to herein as foliar-applied exogenous chemical substances.

Typically, when an exogenous chemical substance is applied to foliage by plant treatment processes known in the art, only a small portion of the amount applied reaches sites of action in the plant where a desired biological activity of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which the exogenous chemical substance is used.

Application to foliage of an exogenous chemical substance by processes known in the art does not universally result in inefficient delivery to sites of action. In some situations such processes provide excellent biological effectiveness, even at a low use rate of the exogenous chemical substance. In other situations the same processes, using the same rate of the exogenous chemical substance, provide inadequate biological effectiveness. Thus, these processes are inconsistent in the result they provide, or they cannot be relied upon to provide the desired result.

A problem is that it is seldom possible to identify in advance those situations where good biological effectiveness will be obtained, partly because so many factors influence efficiency of delivery. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable or consistent biological effectiveness of a foliar-applied exogenous chemical substance, the user typically applies the substance at a higher rate than truly necessary in the majority of situations.

Variability in biological effectiveness in field conditions is an especially troublesome problem in the case of exogenous chemical substances that are acids, and are typically formulated as water-soluble salts in which the exogenous chemical substance is present in an anionic form. Sometimes by converting such acid substances to esters, this variability can be moderated; however, in many cases esters show reduced biological effectiveness, for example due to inadequate conversion back to the parent acid once inside the treated plant. There remains a strong need for enhanced biological effectiveness, and enhanced reliability of biological effectiveness, of foliar-applied exogenous chemical substances, particularly anionic exogenous chemical substances.

The term "anionic exogenous chemical substance" as used herein means an exogenous chemical substance whose molecular structure includes one or more acid, or proton-donating, sites, and is therefore capable of forming an anion in the presence of a proton acceptor. The term therefore embraces substances that are zwitterionic. In describing an exogenous chemical substance as "anionic" herein, it is not implied that the exogenous chemical substance is necessarily in anionic form or that it is dissociated.

Benefits of a process providing greater reliability of biological effectiveness include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in *Weed Technology* 8, 331–386 (1994). Reduced use rates bring rewards not only environmentally but also economically, as the cost per unit area treated decreases.

Foliar-applied exogenous chemical substances have frequently been applied together with amphiphilic materials, particularly amphiphilic surface-active agents, otherwise known as surfactants. Surfactants can influence biological effectiveness of a foliar-applied exogenous chemical substance in numerous ways.

When a dilute aqueous composition of an exogenous chemical substance is applied to foliage by conventional hydraulic spraying, the presence of surfactant in the dilute aqueous composition can alter the size distribution of the spray droplets, typically increasing the percentage of spray volume in the form of small droplets and reducing the percentage of spray volume in the form of large droplets. As smaller droplets have lower momentum than larger droplets, these smaller droplets are less likely to rebound from a foliar surface and consequently are more likely to be retained on that surface. Spray retention can also be facilitated by adhesion between surfactant molecules in a spray droplet and the foliar surface, which in most plants is waxy and hydrophobic. This adhesion reduces not only rebound but also run-off of spray droplets from the foliar surface. Surfactants also tend to increase the area of contact between a spray droplet and a foliar surface, and in many cases enhance penetration of an exogenous chemical substance from the droplet into and through cuticles of leaves to reach internal leaf tissues.

Through these and perhaps other effects, amphiphilic materials including surfactants have long been known to increase the biological effectiveness of exogenous chemical substances. It is therefore commonplace for one or more surfactants to be included in commercial formulations of foliar-applied exogenous chemical substances, even in formulations that do not require the presence of surfactants for acceptable physical stability or handling properties, for example as emulsifying or suspending agents or dispersants.

One of the most extensively studied of foliar-applied anionic exogenous chemical substances, from the point of view of the role of surfactants in enhancing biological effectiveness, is the herbicide glyphosate. As well as being a phytotoxic agent, glyphosate has been used as a plant growth regulator.

Glyphosate in its strict sense is an acid compound, N-phosphonomethylglycine, but the word "glyphosate" is herein used in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of the salts disclosed, the counterion to glyphosate anion is a relatively low molecular weight, non-amphiphilic cation. Typical of such salts are alkali metal, for example sodium and potassium, salts; ammonium salt; and numerous salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup®) brand, Accord® brand and Roundup® Ultra brand herbicides of Monsanto Company, which contain the isopropylammonium salt, Roundup® Dry brand and Rival® brand herbicides of Monsanto Company, which contain the ammonium salt, Roundup® Geoforce brand herbicide of Monsanto Company, which contains the sodium salt, and Touchdown® brand herbicide of Zeneca, which contains the trimethylsulfonium salt.

Salts of glyphosate with higher molecular weight, amphiphilic cations have also been disclosed. Such amphiphilic cations include those having a hydrophilic moiety such as an ammonium, ethanolammonium, polyoxyethylene ammonium, or sulfonium group, and a hydrophobic moiety comprising 1 to 4 hydrocarbyl groups having in total more than 6 carbon atoms. For example, above-cited U.S. Pat. No. 4,405,531, the disclosure of which is incorporated herein by reference, discloses a wide range of primary, secondary and tertiary organic ammonium salts of glyphosate wherein the cation is amphiphilic as defined immediately above and has a molecular weight of less than about 300. International Publication No. WO 83/03608, European Patent Application No. 0 124 351 and U.S. Pat. No. 4,431,594 disclose various quaternary ammonium salts of glyphosate wherein the cation is amphiphilic. U.S. Pat. No. 5,668,085 discloses salts of glyphosate with amphiphilic cations derived from polyoxyethylene tertiary $C_{8-22}$ alkylamine surfactants, a specifically disclosed example being the N-cocoalkyl-N,N-diethanolammonium salt of glyphosate where "cocoalkyl" refers to a mixture of predominantly $C_{12}$ and $C_{14}$ alkyl chains, derived from coconut oil. In all organic ammonium salts of glyphosate specifically identified in the above disclosures, the cation has only one nitrogen-containing group, namely an amino or ammonium group, although above-cited U.S. Pat. No. 4,405,531 generically discloses salts prepared from low molecular weight organic amines "containing not more than 2 amine groups".

Glyphosate as a herbicide has many advantages, particularly environmental advantages including biodegradability and low ecotoxicity. However, studies have shown that even the most biologically effective formulations of glyphosate presently in use do not deliver glyphosate efficiently to sites in the plant where the glyphosate exerts its phytotoxic effect. Typically, only a small fraction of the applied herbicide arrives at such sites. The term "biodisponibilite" (approximately equivalent in meaning to the English word "bioavailability") is used in French patent application no. 97-08371 from which the present application claims priority, to refer to this fraction.

The small fraction of applied glyphosate which reaches sites of phytotoxic action is related to the fact that the glyphosate must go through several barriers. Among these, one of the most important is believed to be the lipophilic cuticle on the foliar surface to which the glyphosate is applied. It has therefore been theorized that it would be desirable to place the glyphosate into an amphiphilic medium which would provide greater compatibility between the lipophilic cuticle and the hydrophilic glyphosate, and thereby facilitate penetration of glyphosate into and through the cuticle. Similar thinking has been applied to other exogenous chemical substances, particularly those typically formulated as water-soluble salts.

That the concept of an amphiphilic medium as an aid to cuticular penetration and thereby enhanced biological effectiveness, for example of glyphosate, has validity is demonstrated by many studies in which foliar uptake or effectiveness has been enhanced by surfactants. An extensive study by Wyrill & Burnside, *Weed Science* 25, 275–287, 1977 led to a conclusion that "an effective surfactant is a critical component of any glyphosate spray mixture", but noted great variation among surfactant types in the degree of enhancement of herbicidal effectiveness afforded. In general, cationic surfactants gave greater enhancement than nonionic surfactants. Data are reported in International Publication No. WO 98/06259 for a wide range of cationic, nonionic, anionic and amphoteric surfactants applied either in mixture with, or in sequence following, a glyphosate composition.

Another approach to providing an amphiphilic medium has been to apply glyphosate together with a lipophilic agent, such as an oil, in the form of a water-in-oil emulsion or microemulsion. Such emulsions or microemulsions are disclosed in European Patent Application No. 0 379 852, U.S. Pat. No. 4,853,026 and U.S. Pat. No. 5,248,086. A disadvantage of such microemulsions is that, when provided as concentrate compositions, they are subject to the phenomenon of breaking of the emulsion upon dilution with water to concentrations suitable for application, for example, 5 grams of glyphosate, expressed as acid equivalent, per liter (g a.e./l). In other words, water-in-oil microemulsions tend not to withstand dilution in water. The failure of such microemulsions to provide improved cuticular penetration is perhaps related to this inability to withstand dilution.

Oil-in-water macroemulsion formulations of glyphosate have also been investigated. In these macroemulsions, the majority of the glyphosate is present in the continuous aqueous phase, as shown, for example, in European Patent Application No. 0 485 207. Such macroemulsions, in which the glyphosate and the lipophilic component are segregated, do not therefore provide glyphosate in an amphiphilic form, and have generally not enhanced delivery of glyphosate to its sites of phytotoxic action in the plant.

A different approach, illustrated in European Patent Specification No. 0 148 169, is to encapsulate a water-soluble herbicide such as glyphosate in a polymeric shell by interfacial polycondensation. In this technique, a water-in-oil emulsion having a lipophilic emulsifier based on alkylated polyvinylpyrrolidone is used. Polymerization to form the shell, by reaction of comonomers, occurs at the oil-water interface of the emulsion containing the herbicide, resulting in formation of a shell that encapsulates the herbicide.

All of the approaches summarized above, including formulating an anionic exogenous chemical substance as an amphiphilic salt, have met with limited success in overcoming the barriers to delivery of the exogenous chemical substance to its sites of biological action in the plant. It is an objective, therefore, of the present invention to provide a new composition or formulation of an exogenous chemical substance, in particular an anionic exogenous chemical substance, that can provide superior biological effectiveness when applied to foliage of a plant.

Another objective of the invention is to provide a composition or formulation of an exogenous chemical substance, in particular an anionic exogenous chemical substance, that is economical and simple to make.

Another objective of the invention, particularly as it applies to the herbicide glyphosate, is to provide a composition or formulation that meets the previously stated objectives while permitting maintenance of the non-ecotoxic and biodegradable character of glyphosate.

Another objective of the invention is to provide a composition or formulation of an exogenous chemical substance, particularly an anionic exogenous chemical substance, that can be applied in a dilute aqueous medium and does not lose its beneficial properties at high rates of dilution.

Another objective of the invention is to provide an aqueous composition or formulation of an anionic exogenous chemical substance in the form of an amphiphilic salt that is physically stable, even at high concentration, without the need for additional stabilizing agents such as dispersants or emulsifying agents.

Another objective of the invention is to provide a convenient and economical method for the preparation of a composition or formulation that meets the objectives stated above.

These and other objectives have been satisfied through design of a new approach for promoting transport of an anionic exogenous chemical substance into plants via foliage, and thereby promoting biological effectiveness of the exogenous chemical substance. This approach, as set out more fully below, involves the production of a colloidal dispersion of supramolecular aggregates, or nanoparticles, containing the exogenous chemical substance wholly or partly in the form of an amphiphilic salt thereof.

SUMMARY OF THE INVENTION

Figure 1:
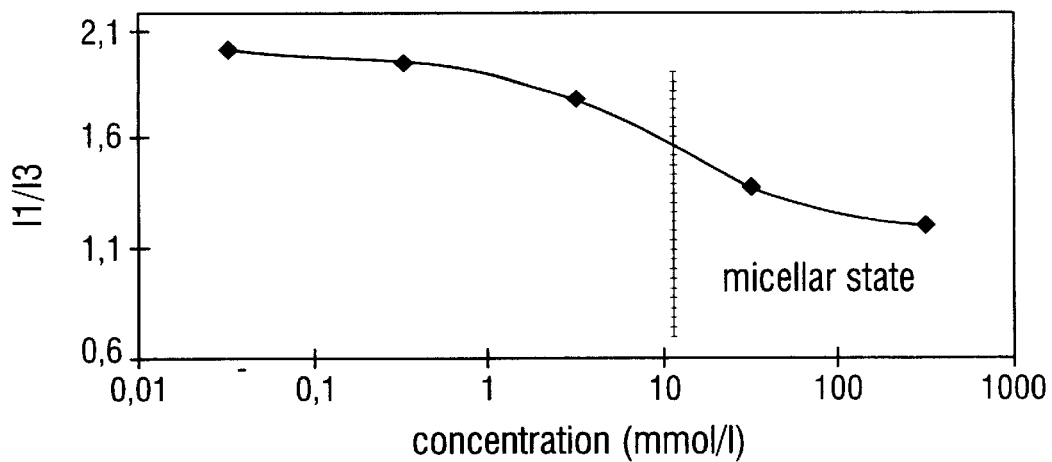
FIG. 1 shows the ratio of fluorescence spectrometry emission bands $I_1I_3$, at wavelengths of 373 and 384 nm respectively, as a function of molar concentration, on a logarithmic scale, of an amphiphilic salt of N-phosphonomethylglycine in an aqueous composition prepared according to Example 1 hereof. The lower $I_1/I_3$ ratio seen at concentrations above about 10 mM is indicative of the amphiphilic salt being in a micellar state.
Figure 2:
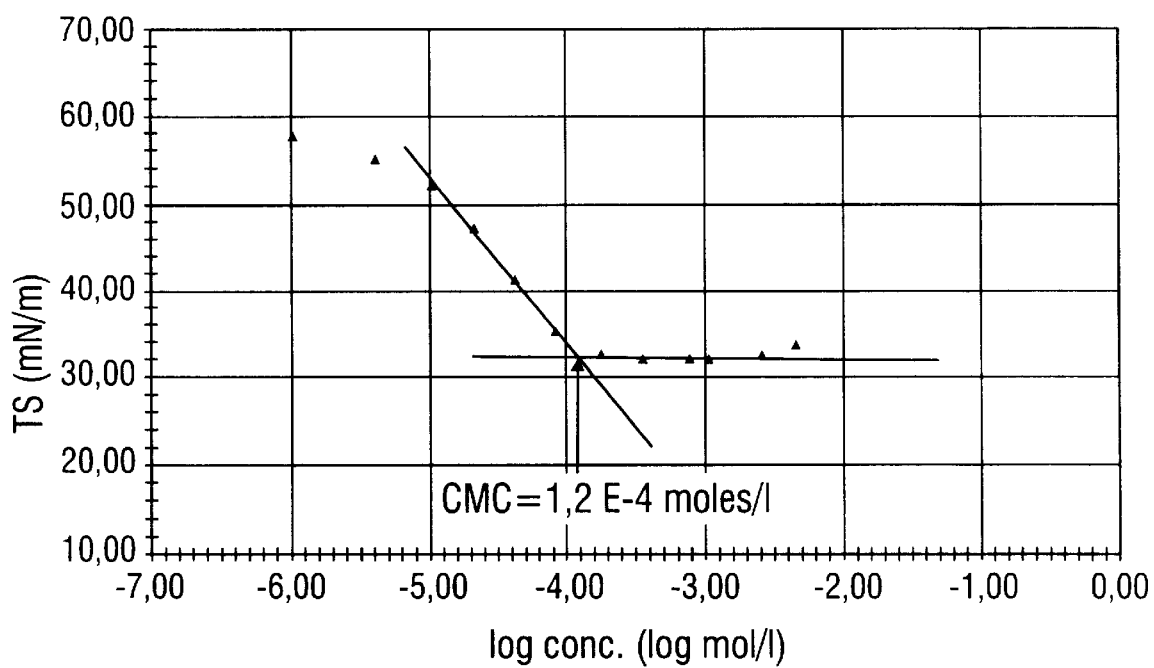
FIG. 2 shows surface tension of an aqueous composition of an amphiphilic salt of N-phosphonomethylglycine as a function of molar concentration of the salt, on a logarithmic scale. The concentration at the indicated break point is the critical micelle concentration (CMC) of the salt in question.

A plant treatment composition for application to foliage of a plant is now provided, comprising an aqueous application medium, in which supramolecular aggregates are colloidally dispersed. The supramolecular aggregates comprise one or more amphiphilic salt(s) having anions of an anionic exogenous chemical substance and cations derived by protonation of one or more polyamine(s) or polyamine derivative(s) each having (a) at least two nitrogen-containing groups, of which a number n not less than 1 are amino groups that can be protonated to form cationic primary, secondary or tertiary ammonium groups, and (b) at least one hydrocarbyl or acyl group having about 6 to about 30 carbon atoms. The composition contains (i) a molar amount X in total of the exogenous chemical substance, in all salt and acid forms thereof present, sufficient to elicit a biological response when the composition is applied to the foliage of the plant at a rate of about 10 to about 1000 l/ha, (ii) a molar amount A in total of said polyamine(s) and derivative(s) thereof and cations derived therefrom, and (iii) a zero or molar amount B in total of one or more monovalent base(s) and cations derived therefrom, said base(s) being other than a polyamine or derivative thereof, such that nA as a fraction of (nA+B) is about 0.01 to 1, and (nA+B) as a fraction of X is about 0.5 to about 10.

The term "polyamine" is used herein to mean an amine compound as required, when protonated, in a composition of the present invention, i.e., an amine compound having (a) at least two nitrogen-containing groups, of which a number n not less than 1 are amino groups that can be protonated to form cationic primary, secondary or tertiary ammonium groups, and (b) at least one hydrocarbyl or acyl group having about 6 to about 30 carbon atoms. Thus the term "polyamine" as used herein includes without restriction diamines, triamines, tetramines, pentamines and derivatives thereof falling within the definition immediately above.

Preferably n is not less than 2, and preferably more than one of the amino groups in the polyamine or derivative thereof are, when formulated in the composition with the exogenous chemical substance, in the form of cationic primary, secondary or tertiary ammonium groups.

The hydrocarbyl or acyl group of each of the polyamine (s) or polyamine derivative(s) preferably comprises a saturated or unsaturated fatty hydrocarbyl chain $R_g$. The polyamine(s) or derivative(s) thereof are preferably selected from the following compounds:

(i) compounds of formula I:

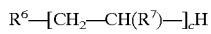

$$R^6-[CH_2-CH(R^7)-]_cH \qquad \text{I}$$

wherein c is an integer from 2 to about 6, $R^6$ is hydrogen, a $C_{1-6}$ alkyl group or a group —L—$R_g$ wherein $R_g$ is as defined above and L is a bonding function as defined below, and $R^7$ is a group —(CONR)$_j$—(CH$_2$)$_m$—NR$_2$ wherein j is 0 or 1, m is an integer from 0 to about 4, and each R is independently hydrogen, a $C_{1-6}$ alkyl group, or a group —L—$R_g$ wherein $R_g$ is as defined above and L is a bonding function as defined below, provided that at least one R or $R^6$ is such a group —L—$R_g$; and (ii) compounds of formula II:

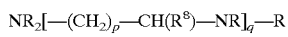

$$NR_2[-(CH_2)_p-CH(R^8)-NR]_q-R \qquad \text{II}$$

wherein $R^8$ is hydrogen or a $C_{1-6}$ alkyl group, p is an integer from 1 to about 5, q is an integer from 1 to about 10, and each R is independently hydrogen, a $C_{1-6}$ alkyl group, or a group —L—$R_g$ wherein $R_g$ is as defined above and L is a bonding function as defined below, provided that at least one R is such a group —L—$R_g$.

The bonding function L in —L—$R_g$ substituents of compounds of formulas I and II can represent any one of the following:

(i) a σ bond (single covalent bond);

(ii) a π bond (double bond) between carbon and carbon atoms (i.e., an ethylenic bond) in a compound of formula I, in which case a hydrogen atom is dropped from the carbon atom to which the $R_g$ group is linked by said a bond, or between carbon and nitrogen atoms in a compound of formula I or formula II, in which case an R group is dropped from the nitrogen atom to which the $R_g$ group is linked by said π bond;

(iii) a carbonyl bridge between the $R_g$ group and the nitrogen atom of an NR group forming, with the NR group, an amido function;

(iv) a succinyl bridge between the $R_g$ group and a nitrogen atom forming, with the nitrogen atom from which an R group is dropped, a succinimidyl function:

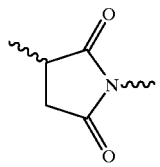

wherein the wavy line attached to the nitrogen atom represents a bond to the repeating group [—(CH$_2$)$_p$—CH($R^8$)—NR] shown in formula II, and the other wavy line represents a bond to the $R_g$ group;

(v) a bridge between the $R_g$ group and a nitrogen atom forming, with the nitrogen atom from which an R group is dropped, an imidazolinyl function:

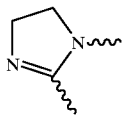

wherein the wavy line attached to the nitrogen atom represents a bond to the repeating group [—(CH$_2$)$_p$—CH($R^8$)—NR] shown in formula II, and the other wavy line represents a bond to the $R_g$ group; or (vi) another bonding function equivalent to any of the above.

The monovalent base(s) other than a polyamine or derivative thereof, if present, are preferably those producing alkali metal cations, ammonium cations, and organic ammonium and sulfonium cations having in total 1–6 carbon atoms.

In one illustrative embodiment, the anionic exogenous chemical substance is N-phosphonomethylglycine (glyphosate).

In one embodiment of the invention, nA as a fraction of (nA+B) is about 0.01 to about 0.2. In another embodiment, nA as a fraction of (nA+B) is about 0.1 to 1, preferably about 0.4 to 1.

A liquid, preferably aqueous, concentrate composition is also provided, which when diluted with a suitable amount of water forms a plant treatment composition as described above. A contemplated liquid concentrate composition contains in total at least about 5% by weight and up to about 50% or more by weight of the anionic exogenous chemical substance expressed as acid equivalent (a.e.).

Also provided is a process for making liquid concentrate compositions of the invention, comprising a neutralizing step and a conditioning step.

The neutralizing step comprises partial or complete neutralization of a first molar amount of an anionic exogenous chemical substance, for example glyphosate, with a molar amount A in total of one or more polyamine(s) or polyamine derivative(s) as defined above in a liquid, preferably aqueous, medium with agitation to make a liquid composition containing one or more amphiphilic salt(s) of the exogenous chemical substance. Optionally the neutralizing step further comprises introducing to the liquid composition, with agitation, a second molar amount of the exogenous chemical substance in the form of one or more salt(s) formed by partially or completely neutralizing the exogenous chemical substance with a molar amount B in total of one or more monovalent base(s) other than a polyamine or derivative thereof. The total molar amount nA of amino groups in the polyamine(s) or polyamine derivative(s), as a fraction of (nA+B), is about 0.01 to 1. The overall degree of neutralization of the exogenous chemical substance, i.e., (nA+B)/X, is about 0.5 to about 10. The salt(s) of the second molar amount of the exogenous chemical substance can be made in situ by neutralizing, in the liquid medium with agitation, this second molar amount with one or more monovalent base(s) before, during or after neutralization of the first molar amount; alternatively such salt(s) can be prepared separately by processes known in the art and added to the liquid medium before, during or after neutralization of the first molar amount.

The conditioning step comprises continuing the agitation of the liquid composition until supramolecular aggregates comprising amphiphilic salt(s) of the exogenous chemical substance formed by partially or completely neutralizing the exogenous chemical substance with one or more polyamine (s) or derivative(s) thereof are colloidally dispersed in the liquid medium.

It is to be understood that the terms "neutralizing" and "neutralization" as used herein refer simply to the admixture of acid and base, and do not necessarily imply reaction of all of the acid and base to form a salt.

Thus an embodiment of the present invention is a liquid concentrate composition prepared by the process just described. It is to be understood, however, that the invention is not limited to this particular embodiment.

Also provided is a process for eliciting a biological activity in a plant or in a pathogen, parasite or feeding organism present in or on the plant, comprising a step of applying to foliage of the plant a biologically effective amount of a plant treatment composition as provided herein.

Contemplated compositions have numerous benefits and advantages.

When applied to foliage of plants according to a process of the invention, a contemplated plant treatment composition in one embodiment provides enhanced biological effectiveness by comparison with commercial standard formulations of the same exogenous chemical substance. For example, at equal application rates of the exogenous chemical substance, a contemplated composition can elicit a greater biological response than a commercial standard formulation. To obtain a given level of biological response, a lower application rate of the exogenous chemical substance can be required when applied in the form of a contemplated composition than in the form of a commercial standard formulation.

A contemplated plant treatment composition in one embodiment is biologically effective at a given application rate on a broader spectrum of target species than commercial standard formulations.

A contemplated plant treatment composition in one embodiment provides greater reliability or consistency of biological effectiveness in a range of environmental conditions than commercial standard formulations.

A contemplated plant treatment composition in one embodiment is more rainfast, i.e., its biological effectiveness is less likely to be reduced by incidence of rain or overhead irrigation occurring within a short period, for example up to about 6 hours, after application, than commercial standard formulations.

A contemplated plant treatment composition in one embodiment provides an observable biological response in a shorter period after application than commercial standard formulations.

The advantages just cited of contemplated plant treatment compositions are not mutually exclusive; indeed in preferred embodiments a contemplated composition possesses more than one of these advantages. Other advantages and benefits will be evident from the detailed description and illustrative examples that follow.

DETAILED DESCRIPTION OF THE INVENTION

Exogenous Chemical Substances

Examples of anionic exogenous chemical substances that can be used in compositions of the present invention include, but are not limited to, chemical pesticides (such as herbicides, algicides, fungicides, bactericides, viricides, insecticides, aphicides, miticides, nematicides and molluscicides), plant growth regulators, fertilizers and nutrients, gametocides, defoliants, desiccants, mixtures thereof and the like. Although the disclosure herein relates to "an exogenous chemical substance", it is to be understood that more than one exogenous chemical substance can be included if desired in a composition of the invention.

A preferred group of anionic exogenous chemical substances consists of those that are normally applied post-emergence to foliage of plants, i.e., foliar-applied anionic exogenous chemical substances. An especially preferred group of foliar-applied anionic exogenous chemical substances consists of those that are systemic in plants, that is, translocated to some extent from their point of entry in the foliage to other parts of the plant where they can usefully exert their biological effect.

Especially preferred among these are herbicides, plant growth regulators and nematicides, particularly those that have a molecular weight, excluding counterions, of less than about 300.

Among such compounds, an even more preferred category consists of nematicides such as those disclosed in U.S. Pat. No. 5,389,680, the disclosure of which is incorporated herein by reference. Preferred nematicides of this group are 3,4,4-trifluoro-3-butenoic acid or N-(3,4,4-trifluoro-1-oxo-3-butenyl)glycine.

In one embodiment of the invention, the exogenous chemical substance is a herbicide. Suitable herbicides include, without restriction, acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Especially preferred herbicides are those whose molecular structure comprises at least one of each of amine, carboxylate, and either phosphonate or phosphinate functional groups. This category includes the herbicides N-phosphonomethylglycine (glyphosate) and DL-homoalanin-4-yl(methyl) phosphinate (glufosinate). Another preferred group of herbicides are those of the imidazolinone class, including imazameth, imazamethabenz, imazamox, imazapyr, imazaquin and imazethapyr.

The invention is illustrated herein by particular reference to glyphosate. Although glyphosate has three acid sites, and can therefore form tribasic salts, preferred aqueous compositions have a pH value not greater than about 8, at which pH value the fraction of glyphosate existing as a tribasic salt is negligibly small. Only the two acid sites that are significantly deprotonated at pH 8 are therefore considered herein. One of these is on the phosphonate moiety, and the other is on the carboxylate moiety, of the glyphosate molecule.

In plant treatment compositions of the invention, the amount of exogenous chemical substance present, in all forms thereof, is sufficient when applied to foliage of a plant to elicit the desired biological activity. Such compositions are sometimes referred to as "spray compositions", "sprayable compositions" or "ready-to-use compositions" and typically contain about 0.02% by weight to about 2% by weight of the exogenous chemical substance, expressed as acid equivalent (a.e.). For some purposes such compositions can contain up to about 5% a.e. by weight or even 10% a.e. by weight.

In liquid concentrate compositions of the invention, the amount of exogenous chemical substance present, in all forms thereof, provides, upon dilution in a suitable volume of water and application of the diluted composition to foliage of a plant, a sufficient amount to elicit the desired biological activity. Liquid concentrate compositions contain about 5% a.e. by weight to about 50% a.e. by weight or more of the exogenous chemical substance, in all forms thereof present. In typical liquid concentrate compositions the exogenous chemical substance is present in all forms thereof at about 20% to about 40% a.e. by weight.

As a significant portion of the cost of a packaged liquid concentrate composition is the volume-related cost of packaging, transport and storage, it is desirable to increase to the maximum practicable extent the concentration, or "loading", of exogenous chemical substance in the composition. Generally the factor that limits loading is physical stability of the composition under a range of storage conditions. The upper limit of loading depends on the nature and concentration of other ingredients in the composition and can be readily determined by routine experimentation using procedures known in the art.

For commercial purposes, loading is often expressed in weight/volume terms (e.g., grams per liter, g/l) rather than as a percentage by weight. Useful exogenous chemical substance, e.g., glyphosate, loadings for ready-to-use and concentrate compositions of the invention can range from about 1 g a.e./l to about 560 g a.e./l, typically about 1 g a.e./l to about 400 g a.e./l.

Amphiphilic Salt(s) of the First Molar Amount of the Exogenous Chemical Substance Compositions of the invention contain supramolecular aggregates comprising amphiphilic salt(s) formed by partial or complete neutralization of a first molar amount of the anionic exogenous chemical compound by one or more polyamine(s) as defined above or derivative(s) of such polyamine(s). It is to be understood that the presence of a significant portion of the anionic exogenous chemical compound outside such supramolecular aggregates, for example in solution in a continuous aqueous phase of the composition, does not remove such a composition from the scope of the present invention.

Polyamines and derivatives thereof useful in the invention have at least one hydrocarbyl or acyl group having about 6 to about 30, preferably about 8 to about 22, carbon atoms.

The polyamine(s) or derivative(s) thereof are preferably selected from compounds of formula II:

wherein $R^8$ is hydrogen or a $C_{1-6}$ alkyl group, p is an integer from 1 to about 5, q is an integer from 1 to about 10, and each R is independently hydrogen, a $C_{1-6}$ alkyl group, or a group —L—$R_g$ wherein $R_g$ is as defined above and L is a bonding function, provided that at least one R is such a group —L—$R_g$.

The bonding function can be of types (i) to (vi) as described above. A bonding function of type (v), forming an imidazolinyl ring, can arise by cyclization of a portion of a polyamine molecule of formula II, where the alkylene bridges between amino groups are ethylene bridges, i.e., where p is 1 and $R^8$ is hydrogen. Such cyclization can occur if heating is excessive during N-alkylation, for example, of tetraethylenepentamine with 1-bromododecane to make N-lauryl tetraethylenepentamine. Cyclization can incorporate the site of N-alkylation, in which case an imidazolinyl bridge as illustrated above results, but it can also occur elsewhere in the polyamine molecule. It is to be understood that polyamines useful in the present invention include partially cyclized polyamines.

However, it is preferred that in polyamines and derivatives of formula II, each bonding function L is independently of type (i), i.e., a σ bond, type (iii), i.e., a carbonyl bridge, or type (iv), i.e., a succinyl bridge. Where a bonding function L is a carbonyl or succinyl bridge, the nitrogen-containing group to which it is attached becomes an amido or imido group and can no longer be protonated to form a cationic ammonium group.

It is preferred that in polyamines and derivatives of formula II, all bonding functions L are the same. It is especially preferred that all bonding functions L are σ bonds, or that all bonding functions L are carbonyl bridges.

Most preferably in polyamines and derivatives of formula II, p is 1 to 5, $R^8$ is hydrogen, except where p is 1 in which case $R^8$ is hydrogen or a methyl group, q is 1 to 4, and bonding functions L are either all σ bonds or all carbonyl bridges.

Particularly preferred polyamines and derivatives thereof are derived by N-alkylation or N-acylation of compounds of formula III:

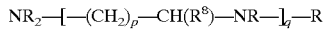

(p, q and $R^8$ being defined as immediately above) selected from ethylenediamine, 1,2-diaminopropane (otherwise known as propylenediamine), 1,3-diaminopropane (otherwise known as trimethylenediamine), 1,4-diaminobutane (otherwise known as butylenediamine), 1,6-diaminohexane (otherwise known as hexamethylenediamine), diethylenetriamine, triethylenetetramine, tetraethylenepentamine, bis(trimethylene)triamine (otherwise known as dipropylenetriamine), tris(trimethylene)tetramine (otherwise known as tripropylenetetramine), dibutylenetriamine and bis(hexamethylene)triamine (otherwise known as dihexamethylenetriamine).

Where L is a σ bond, $R_g$ is preferably a linear hydrocarbyl chain having at least 8, most preferably at least 10, carbon atoms. Illustrative examples of such hydrocarbyl chains include those with even numbers of carbon atoms, such as n-octyl, n-octenyl, n-decyl, n-decenyl, lauryl, lauroleyl, myristyl, myristoleyl, palmtyl, paintoleyl, stearyl, oleyl, linoleyl, arachidyl, gadoleyl, behenyl and erucyl chains. Chains with odd numbers of carbon atoms, such as n-nonyl and n-tridecyl are also useful, but are typically less abundantly available and consequently more expensive. In particularly preferred examples $R_g$ groups have 12, 14, 16 or 18 carbon atoms and are typically derived from lauric, myristic, palmitic, stearic, oleic, linolenic, linoleic or other natural fatty acids, with saturated chains such as lauryl, myristyl, palmityl or stearyl groups being especially preferred.

Where L is a carbonyl bridge, —L—$R_g$ (i.e., —CO—$R_g$ is preferably a linear acyl chain having at least 8, most preferably at least 10, carbon atoms. Illustrative examples of such acyl chains having even numbers of carbon atoms include n-octanoyl, n-octenoyl, n-decanoyl, n-decenoyl, lauroyl, lauroleoyl, myristoyl, myristoleoyl, palmitoyl, palmitoleoyl, stearoyl, oleoyl, linoleoyl, arachidoyl, gadoleoyl, behenoyl and erucoyl chains. Together with the adjacent nitrogen-containing group these chains become hydrocarbamide groups including, illustratively, n-octanamide, n-octenamide, n-decanamide, n-decenamide, lauramide, lauroleamide, myristamide, myristoleamide, palmitamide, palmitoleamide, stearamide, oleamide, linoleamide, arachidamide, gadoleamide, behenamide and erucamide groups. In particularly preferred examples, acyl chains have 12, 14, 16 or 18 carbon atoms and are typically derived from lauric, myristic, palmitic, stearic, oleic, linolenic, linoleic or other natural fatty acids, with saturated acyl chains such as lauroyl, myristoyl, palmtoyl or stearoyl chains being especially preferred.

In polyamines and derivatives thereof of formula II having more than one $R_g$ group, these $R_g$ groups can be linked via bonding functions L to the same or different nitrogen atoms. In a compound described herein as, for example, N,N-dilauryl triethylenetetramine it is not to be inferred that both lauryl groups are necessarily attached to the same nitrogen atom. Indeed, it is statistically more likely that they will be attached to different nitrogen atoms.

$R_g$ groups can be derived from a range of fatty acids occurring in a natural feedstock such as castor oil, coconut oil, olive oil, palm oil, soybean oil or beef tallow. For example, in N-cocoalkyl dipropylenetriamine, where the cocoalkyl moiety is derived from coconut oil, a variety of $R_g$ groups occur, of predominantly $C_{12}$ and $C_{14}$ chain lengths.

In the following illustrative examples of polyamines of formula II which can be useful in the invention, L is a σ bond: N-lauryl trimethylenediamine, N-stearyl trimethylenediamine, N-oleyl trimethylenediamine, N-lauryl butylenediamine, N-stearyl butylenediamine, N-lauryl hexamethylenediamine, N-myristyl hexamethylenediamine, N-lauryl dipropylenetriamine, N-oleyl dipropylenetriamine, N-(n-decyl) bis(hexamethylene)triamine, N-lauryl bis(hexamethylene) triamine, N-lauryl triethylenetetramine, N,N-dilauryl triethylenetetramine, N-palmityl triethylenetetramine, N-stearyl triethylenetetramine, N,N-distearyl triethylenetetramine, N-(n-octyl) tetraethylenepentamine, N-(n-octyl) tetraethylenepentamine, N-lauryl tetraethylenepentamine, N,N-dilauryl tetraethylenepentamine, N-lauroleyl tetraethylenepentamine, N-stearyl tetraethylenepentamine and N,N-distearyl tetraethylenepentamine.

In the following illustrative examples of polyamine derivatives of formula II which can be useful in the invention, L is a carbonyl bridge: n-octanamide, n-decanamide, lauramide, stearamide and oleamide derivatives of diethylenetriamine and bis(hexamethylene)triamine; and n-octanamide, di(n-octanamide), n-decanamide, di(n-decanamide), lauramide, dilauramide, stearamide, distearamide, oleamide and dioleamide derivatives of triethylenetetramine and tetraethylenepentamine.

A composition of the invention can advantageously be prepared by reaction of a polyamine with a natural oil or fat such as coconut oil, palm oil, castor oil, olive oil, soybean oil, beef tallow, etc. Without being bound by theory, it is believed that this reaction involves N-acylation of the polyamine by the fatty acid components of the oil or fat to form a crude mixture of fatty amide derivatives of the polyamine, together with free glycerol and other materials naturally present in the starting materials. Compositions prepared in this way are of relatively low cost and typically exhibit no loss of useful properties, although they can be purified if desired. It has surprisingly been found that certain compositions prepared as crude mixtures using a natural oil or fat as starting material can be loaded with an exogenous chemical compound such as glyphosate to a higher concentration than when prepared using relatively pure starting materials.

An illustrative example of a polyamine derivative of formula II where L is a succinyl bridge is the succinimide compound represented by the following formula:

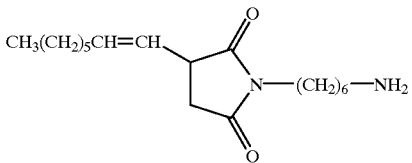

As indicated above, commercial preparations of polyamines and polyamine derivatives can contain a range of hydrocarbyl or acyl chain lengths, sometimes with varying degrees of unsaturation. Thus when amounts of a polyamine or derivative thereof are specified herein, it is to be understood that such amounts are inclusive of other polyamines or derivatives thereof present in the preparation used.

In some embodiments of the invention, the amphiphilic salt(s) of the exogenous chemical substance and one or more polyamine(s) or polyamine derivative(s) are the only salts of the exogenous chemical substance present in the composition. In such embodiments the first molar amount of the exogenous chemical substance represents the total molar amount X of the exogenous chemical substance present in salt form or accompanied by a base. The molar amount nA of amino groups, whether protonated or not, contributed by the polyamine(s) or derivative(s) thereof in such embodiments is about 1 mole per mole of anionic exogenous chemical substance in the case of a monobasic salt, and about 2 moles per mole of anionic exogenous chemical substance in the case of a dibasic salt. However, nA/X can be lower than 1, for example as low as about 0.5, and can be considerably in excess of 2. A value of nA/X<1 is consistent with a fraction of the anionic exogenous chemical substance being present in its acid form, while a value of nA/X>2 means that the polyamine(s) or derivative(s) thereof are present in an amount sufficient to contribute significantly more than 2 moles of amino groups per mole of anionic exogenous chemical substance. Indeed nA/X can, if desired, be as high as about 10, but preferably is not higher than about 5, more preferably not higher than about 2.

In general it is preferred to keep the amount of polyamine or derivative thereof as low as possible within the ranges disclosed above, as excess polyamine or polyamine derivative tends to restrict the maximum loading of exogenous chemical substance achievable in a concentrate composition.

Where one or more salt(s) of a second molar amount of the exogenous chemical substance with a total molar amount B of one or more monovalent base(s) are present in a composition of the invention, the amount of amphiphilic salt(s) of the exogenous chemical substance with polyamine (s) or polyamine derivative(s) is correspondingly reduced as a fraction of all salts of the exogenous chemical substance present. In general, to provide the benefits of the present invention, the molar amount of amino groups contributed by polyamine(s) and derivative(s) thereof should be not less than about 1% of all cation-forming groups present, i.e., nA as a fraction of (nA+B) is about 0.01 to 1.

In one embodiment of the invention, nA represents a relatively small fraction of (nA+B), for example about 0.01 to about 0.2. In this embodiment, it is a primary objective to prepare a stable concentrate composition with a high loading of the exogenous chemical substance on an acid equivalent basis. As polyamines and their derivatives have relatively high molecular weight, it is difficult to achieve the desired high loading except where relatively low molecular weight monovalent cations, for example sodium, ammonium or isopropylammonium cations, predominate.

In another embodiment of the invention, nA represents a larger fraction of (nA+B), for example about 0.1 to 1, preferably about 0.4 to 1. In this embodiment, it is a primary objective to maximize the biological effectiveness of the composition, even if this means a relatively low loading of the exogenous chemical substance has to be accepted. Compositions illustrated in the Examples herein have nA/(nA+B) substantially equal to 1; in reading these Examples it will be recognized that the illustrative compositions can optionally further contain a monovalent salt of the exogenous chemical substance, in these Examples glyphosate, other than a salt formed with a polyamine or derivative thereof. In such a case, nA/(nA+B) will become less than 1.

It is believed that in a typical concentrate liquid composition of the invention, a significant fraction, for example more than about 10% by weight, preferably more than about 50% by weight, of the amphiphilic salt(s) formed by the exogenous chemical substance and polyamine(s) or polyamine derivative(s) are located in the supramolecular aggregates which are colloidally dispersed in the liquid, preferably aqueous, medium. This can be verified by isolating the supramolecular aggregates from the medium by techniques known in the art such as filtration or centrifugation, and analyzing the two components thus obtained. Upon dilution of a concentrate composition in water to form a plant treatment composition, more of the amphiphilic salt(s) may be partitioned in the aqueous medium; however it is presently believed that even under these circumstances, in preferred compositions, most or substantially all of the amphiphilic salt(s) remain in the supramolecular aggregates.

Without being bound by theory, it is believed that location of a significant proportion of an exogenous chemical substance in supramolecular aggregates, as a result of the amphiphilic nature of salt(s) made by neutralizing the exogenous chemical substance with one or more polyamine(s) or polyamine derivative(s), accounts at least in part for the superior biological effectiveness of compositions of the invention when applied to foliage of plants, through improved penetration into and through cuticles.

Salt(s) of the Second Molar Amount of the Exogenous Chemical Substance

The second molar amount in one embodiment of the invention is essentially zero. However, if a second molar amount of the exogenous chemical substance is present as one or more salt(s) of monovalent base(s), such second molar amount can be present predominantly in the supramolecular aggregates, predominantly in the aqueous medium, or more or less equally in both. Such salt(s) can be amphiphilic or non-amphiphilic. Where a salt of the second molar amount is an amphiphilic salt, it is believed that it will be predominantly located in the supramolecular aggregates.

The cation(s) of salt(s) of the second molar amount of the exogenous chemical substance are provided by base(s) other than a polyamine or derivative thereof. Preferred such cations include (i) alkali metal, for example sodium and potassium, cations, (ii) ammonium cations, and (iii) organic ammonium and sulfonium cations having in total 1–6 carbon atoms.

Particular examples of cations useful in salts of the second molar amount of the exogenous chemical substance include sodium, ammonium, dimethylammonium, isopropylammonium, monoethanolammonium and trimethylsulfonium cations.

Characteristics of a Contemplated Composition

By selecting the particular amphiphilic salts disclosed herein, the colloidal dispersions of supramolecular aggregates formed, for example when compositions are prepared by a process as described herein, have surprisingly been found to exhibit a high degree of physical stability. The supramolecular aggregates themselves, as well as the composition as a whole, are physically stable, a feature which is of great benefit in the handling, storage and use of compositions of the invention.

A particularly unexpected discovery is that the supramolecular aggregates substantially maintain their structural integrity even upon dilution to levels useful for direct application to foliage of plants, for example a concentration of 0.5% by weight of the exogenous chemical substance, expressed as acid equivalent. In one embodiment, this structural integrity is not dependent on the presence of dispersants or emulsifying agents, or indeed of any surfactants other than the amphiphilic salt formed by the exogenous chemical substance with the polyamine or polyamine derivative (if indeed such amphiphilic salt(s) can be considered "surfactants"). However, as indicated below, surfactants other than the amphiphilic salt(s) of the exogenous chemical substance can optionally be present in compositions of the invention.

More precisely, aqueous concentrate compositions of the invention can be described as stable colloidal dispersions of supramolecular aggregates. By "stable" in this context it is meant that no phase separation occurs during storage of a composition without agitation at 15° C. for 48 hours. The more desirable aqueous concentrate compositions of the invention are colloidal dispersions in which no phase separation occurs during storage without agitation at constant or varying temperatures from about 10° C. to about 40° C. for 48 hours, even more desirably from about 0° C. to about 50° C. for 7 days, and most desirably about −10° C. to about 60° C. for 30 days. Stability at elevated temperatures for short time periods provides a good indication of long-term stability under normal storage conditions; it is contemplated that certain concentrate compositions of the invention will be stable for periods of 1 year or more under normal storage conditions.

The supramolecular aggregates of compositions of the invention are sometimes referred to as nanoparticles. The term "nanoparticle" has no universally accepted definition in the art; however as used herein the term refers to bodies whose longest dimension is of a size up to about 1 $\mu$m (1000 nm), and includes bodies that are not solid particulates.

The supramolecular aggregates present in compositions of the invention are of at least two types. A first type is of a size too small to be detectable by transmission electron microscopy, but measurable by other techniques known in the art such as dynamic light scattering. Supramolecular aggregates of this first type have characteristics of more or less spherical micelles, colloidal dispersions of which in an aqueous medium are variously referred to as emulsions, microemulsions, micellar emulsions and micellar solutions. Unless the context demands otherwise, the term "emulsion" as descriptive of a composition of the present invention is herein reserved for compositions where the micelles or other supramolecular aggregates contain, in addition to amphiphilic salt(s) of an exogenous chemical substance, an oil as described in greater detail below. In the absence of such oil, the micelles, or supramolecular aggregates of the first type, typically have a mean diameter of about 1 to about 10 nm, most commonly about 2 to about 5 nm.

It should be noted that the compositions containing oil in addition to amphiphilic salt(s) as disclosed immediately above are to be distinguished from those mentioned earlier wherein an oil is reacted with a polyamine to form a mixture of N-acylated polyamines which are then reacted with an anionic exogenous chemical substance in acid form to prepare such amphiphilic salts.

In common with other micellar dispersions, compositions of the invention exhibit a critical micelle concentration (CMC), which is a concentration of an amphiphilic material below which molecules of the amphiphilic material do not aggregate to form micelles. Compositions of the invention preferably have a CMC not greater than about 30 mM, more preferably not greater than about 1 mM. Some compositions of the invention have a CMC as low as 35 $\mu$M or even lower. A method for determining the CMC of a composition of the invention is provided in the Examples herein.

It is, at least in part, the very low CMC of preferred compositions of the invention that enables the supramolecular aggregates, or micelles, to survive dilution to the levels useful as spray compositions. For example, a concentrate composition containing 169 g/l (1 mole) of glyphosate, all in the form of an amphiphilic salt with N-cocoalkyl trimethylenediamine, when diluted 100 times with water, provides a spray composition having a 10 mM concentration of the amphiphilic salt. This salt has a CMC of about 160 $\mu$M. Even if only 5% of the glyphosate in the concentrate composition is in the form of this amphiphilic salt, with the remaining glyphosate in the form of non-amphiphilic salts, the concentration of the amphiphilic salt following 100-fold dilution with water is, at 500 $\mu$M, still above the CMC for this salt, so that micelles will still be present.

Compositions of the invention can also contain supramolecular aggregates of a second type. These are typically 20–100 nm in size and are normally spherical. They are too large to be simple micelles and are believed to be vesicular, multilamellar or liposome-like in structure. The size of supramolecular aggregates larger than simple micelles can be measured by observation using transmission electron microscopy (TEM) with the negative staining technique. A suitable colorant is sodium silicotungstate, $Na_4(Si(W_3O_{10})_4) \cdot 20H_2O$.

Typically, concentrate compositions of the invention are clear or slightly turbid. Concentrate compositions that are milky or opaque are not excluded from the invention, but are less likely to show long-term stability and are less preferred for this reason. In general, concentrate compositions wherein a high proportion of the polyamine or polyamine derivative compounds are "single-tailed", i.e., have only one hydrophobic hydrocarbyl or acyl group per molecule, tend to be clear, while those having a mixture of single-tailed and twin- or multi-tailed polyamines or polyamine derivatives are commonly turbid, milky or opaque.

Other Optional Ingredients

Optionally, compositions of the invention can contain agriculturally acceptable materials other than an exogenous chemical substance or a salt thereof as described herein.

For example, more than one exogenous chemical substance can be included. An additional anionic exogenous chemical substance can be included, selected for example from those hereinbefore listed. Alternatively or in addition, an exogenous chemical substance that is other than anionic as defined herein can be included. For example, a glyphosate composition of the invention can optionally contain, in addition to glyphosate, an anionic herbicidal compound such as acifluorfen, bilanafos, 2,4-D, dicamba, fluazifop, fluoroglycofen, glufosinate, imazamox, imazapyr, imazaquin, imazethapyr, MCPA, nonanoic acid or picloram. Such additional anionic compound is present as salt(s) comprising cations derived from polyamine(s) or derivatives thereof, and optionally from monovalent base(s) other than a polyamine or derivative thereof, as described herein. Similarly, a composition of the invention containing salts of an anionic herbicide can optionally contain a herbicidal compound that is other than anionic, such as for example an ester derivative of an anionic herbicide, acetochlor, aclonifen, alachlor, atrazine, bensulfuron, bifenox, butachlor, chlorimuron, chlorsulfuron, clomazone, cyanazine, diflufenican, diquat, dithiopyr, diuron, flazasulfuron, flumetsulam, flumioxazin, fluometuron, flupoxam, halosulfuron, isoproturon, isoxaben, metolachlor, metsulfuron, nicosulfuron, oryzalin, oxyfluorfen, paraquat, pendimethalin, phenmedipham, propachlor, propanil, pyridate, sethoxydim, simazine, sulfometuron, thiazopyr, triallate, triasulfuron or trifluralin.

Exogenous chemical substances useful in compositions of the invention can be selected from those listed in standard reference works such as *The Pesticide Manual,* 11th Edition, British Crop Protection Council (1997), and *Farm Chemicals Handbook '97,* Meister Publishing Company (1997).

Various agriculturally acceptable adjuvants or excipient substances can also be included, whether or not their purpose is to contribute directly to the biological effectiveness of an exogenous chemical substance in a treated plant. For example, where the exogenous chemical substance is a herbicide, liquid nitrogen fertilizer or ammonium sulfate can be included in the composition. In some instances it can be desirable to include microencapsulated acid in the composition, to lower the pH of a spray solution on contact with foliage.

Other optional components of compositions of the invention include agents to modify color, odor, viscosity, gelling properties, freezing point, stability or texture.

One or more surfactant(s), other than amphiphilic salts of an exogenous chemical substance, can also be included in a contemplated composition. A wide range of surfactants is available to the formulator of exogenous chemical substances and can be selected readily from standard works such as *McCutcheon's Emulsifiers and Detergents,* 1997 Edition, MC Publishing Company, or *Handbook of Industrial Surfactants,* 2nd Edition, Gower (1997).

There is no restriction on the type or chemical class of surfactant that can be used. Nonionic, anionic, cationic and amphoteric types, or combinations of more than one of these types, are all useful in particular situations.

Many surfactants useful herein have a chemical structure that comprises one or more moieties each consisting of a single $C_{2-4}$ alkylene oxide unit or a polymerized or copolymerized chain of $C_{2-4}$ alkylene oxide units. Such surfactants are referred to as polyoxyalkylene surfactants and include nonionic, anionic, cationic and amphoteric types. Polyoxyalkylene surfactants useful in presently contemplated compositions contain about 2 to about 100 $C_{2-4}$ alkylene oxide units. In preferred polyoxyalkylene surfactants the alkylene oxide units form one or more chain(s) of either ethylene oxide or copolymerized ethylene oxide and propylene oxide, each chain of alkylene oxide units having a terminal hydrogen or a $C_{1-4}$ alkyl or $C_{1-4}$ acyl end-cap.

Hydrophobic moieties of surfactants useful in compositions of the invention can be essentially hydrocarbon-based, in which case the hydrophobic moieties are typically $C_{8-24}$, preferably $C_{12-18}$, alkyl, alkenyl, alkynyl, alkylaryl or acyl groups. These groups can be linear or branched hydrocarbyl or acyl chains. Alternatively, the hydrophobic moieties can contain silicon atoms, for example in the form of siloxane groups such as heptamethyltrisiloxane groups, or fluorine atoms, for example as partially fluorinated alkyl or perfluoroalkyl chains.

Among nonionic surfactants, especially preferred classes include polyoxyethylene alkyl, alkenyl, alkynyl or alkylaryl ethers, such as polyoxyethylene primary or secondary alcohols, alkylphenols or acetylenic diols; polyoxyethylene alkyl or alkenyl esters, such as ethoxylated fatty acids; sorbitan alkylesters, whether ethoxylated or not; glyceryl alkylesters; sucrose esters; and alkyl polyglycosides. Representative specific examples of such nonionic surfactants include polyoxyethylene (9) nonylphenol, Neodol™ 25-7 of Shell (a polyoxyethylene (7) $C_{12-15}$ linear primary alcohol), Tergitol™ 15-S-9 of Union Carbide (a polyoxyethylene (9) $C_{12-15}$ secondary alcohol), Tween™ 20 of ICI (a polyoxyethylene (20) sorbitan monolaurate), Surfynol™ 465 of Air Products (a polyoxyethylene (10) 2,4,7,9-tetramethyl-5-decyne-4,7-diol) and Agrimul™ PG-2069 of Henkel (a $C_{9-11}$ alkyl polyglucoside).

Among anionic surfactants, especially preferred classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Among cationic surfactants, especially preferred classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) ethoxytrimethylammonium chloride. Particularly preferred polyoxyethylene alkyletheramines are those disclosed in International Publication No. WO 96/32839.

Many cationic quaternary ammonium surfactants of diverse structures are known in the art to be useful in combination with glyphosate and other exogenous chemical substances and can be used in compositions contemplated herein; such quaternary ammonium surfactants have formula VII:

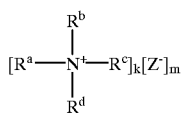

VII where $Z^-$ is a suitable anion such as chloride, bromide, iodide, acetate, salicylate, sulfate or phosphate; k and m are integers such that the positive electrical charges on cations balance the negative electrical charges on anions; and options for $R^a$, $R^b$, $R^c$ and $R^d$ include the following, without limitation:

(i) $R^a$ is a benzyl or $C_{8-24}$, preferably a $C_{12-18}$, alkyl or alkenyl group, and $R^b$, $R^c$ and $R^d$ are independently $C_{1-4}$ alkyl, preferably methyl, groups;

(ii) $R^a$ and $R^b$ are independently $C_{8-24}$, preferably $C_{12-18}$, alkyl or alkenyl groups, and $R^c$ and $R^d$ are independently $C_{1-4}$ alkyl, preferably methyl, groups;

(iii) $R^a$ is a $C_{8-24}$, preferably a $C_{12-18}$, alkyl or alkenyl group, $R^b$ is a polyoxyalkylene chain having about 2 to about 100 $C_{2-4}$ alkylene oxide units, preferably ethylene oxide units, and $R^c$ and $R^d$ are independently $C_{1-4}$ alkyl, preferably methyl, groups;

(iv) $R^a$ is a $C_{8-24}$, preferably a $C_{12-18}$, alkyl or alkenyl group, $R^b$ and $R^c$ are polyoxyalkylene chains having in total about 2 to about 100 $C_{2-4}$ alkylene oxide units, preferably ethylene oxide units, and $R^d$ is a $C_{1-4}$ alkyl, preferably a methyl, group; or (v) $R^a$ is a polyoxyalkylene chain having about 2 to about 100 $C_{2-4}$ alkylene oxide units in which $C_{3-4}$ alkylene oxide units, preferably propylene oxide units, predominate, and $R^b$, $R^c$ and $R^d$ are independently $C_{1-4}$ alkyl, preferably methyl or ethyl, groups. Particularly preferred quaternary ammonium surfactants of this type are those disclosed in U.S. Pat. No. 5,464,807.

In a preferred embodiment of the present invention, an amphiphilic quaternary ammonium compound, or mixture of such compounds, is present, having formula VIII:

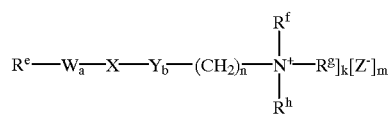

VIII wherein $R^e$ is a hydrocarbyl or haloalkyl group having about 6 to about 22 carbon atoms; W and Y are independently O or NH; a and b are independently 0 or 1 but at least one of a and b is 1; X is CO, SO or $SO_2$; n is 2 to 4; $R^f$, $R^g$ and $R^h$ are independently $C_{1-4}$ alkyl; and k, m and $Z^-$ have the same meanings as in formula VII. $R^e$ in one particular embodiment is a hydrocarbyl group having about 12 to about 18 carbon atoms. $R^e$ can also be fluorinated. In one specific embodiment, $R^e$ is perfluorinated, and preferably has about 6 to about 12 carbon atoms. In one particularly preferred embodiment, $R^e$ is a saturated perfluoroalkyl group having about 6 to about 12 carbon atoms, X is CO or $SO_2$, Y is NH, a is 0, b is 1, n is 3, $R^f$, $R^g$ and $R^h$ are methyl groups, k and m are each 1, and $Z^-$ is a chloride, bromide or iodide anion.

Sulfonylamino compounds of formula VIII, i.e., those wherein X is $SO_2$, Y is NH, a is 0 and b is 1, are especially preferred. Suitable examples include 3-(((heptadecafluorooctyl)sulfonyl)amino)-N,N,N-trimethyl-1-propaminium iodide, available for example as Fluorad™ FC-135 from 3M Company, and the corresponding chloride. It is believed that Fluorad™ FC-754 of 3M Company comprises the corresponding chloride.

When included, amphiphilic quaternary ammonium compound(s) of formula VIII are present in an adjuvant amount, i.e., an amount sufficient to provide visibly improved biological effectiveness of the exogenous chemical substance by comparison with a composition lacking such compound(s). "Visibly improved" in the present context means that, in a side-by-side comparison, a difference in biological effectiveness in favor of the composition containing the amphiphilic quaternary ammonium compound(s) would be evident to an experienced technician in the art relating to the particular class of exogenous chemical substance being applied, for example a weed scientist in the case where the exogenous chemical substance is a herbicide such as glyphosate.

When present, one or more amphiphilic quaternary ammonium compound(s) of formula VIII are preferably included in a ratio of total weight of such compound(s) to weight of the anionic exogenous chemical substance, expressed as acid equivalent, of about 1:3 to about 1:100.

Suitable concentrations of a compound of formula VIII are about 0.001% to about 1% by weight in a plant treatment composition, and about 0.01% to about 10% by weight in a liquid concentrate composition of the invention.

Yet another class of excipient material that can be useful in compositions of the present invention is an oil, such as a triglyceride ester of fatty acids of animal, vegetable or synthetic origin, a paraffin, a polysiloxane, or a fatty acid or an ester or amide thereof. Such an oil, or mixture of oils, is present in an adjuvant amount as defined above. Examples of suitable oils include triglyceride esters of the coconut oil type, such as the product Miglyol™ 812 of Hüls, corn oil, olive oil, $C_{12-15}$ alkyl benzoate, eicosapentaenoic and docosahexaenoic acids and alkyl and triglyceride esters thereof and triglyceride ester of caprylic acid. Oils can be fractionated or not. Fractionation permits elimination of certain fatty acid chain lengths so as to modify melting point.

In a particular embodiment of the invention, one or more oil(s) are included, each having a chemical structure corresponding to formula IX:

$$R^{14}-CO-Y-R^{15} \qquad \text{IX}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and Y is O or NH. $R^{14}$ and $R^{15}$ are preferably linear hydrocarbyl chains. $R^{14}$ preferably has about 11 to about 21 carbon atoms and is preferably derived from a natural saturated or unsaturated fatty acid. $R^{15}$ is preferably an alkyl group with 1 to about 6 carbon atoms. Especially preferred oils of formula IX are therefore $C_{1-6}$ alkylesters or $C_{1-6}$ alkylamides of fatty acids. It is further preferred that $R^{14}$ is saturated in about 40% to 100% by weight of all compounds of formula IX present in the composition.

In certain preferred embodiments, an oil is included that is a $C_{1-4}$ alkylester of a $C_{12-18}$ fatty acid, more preferably a $C_{1-4}$ alkylester of a $C_{12-18}$ saturated fatty acid. Examples include methyl oleate, ethyl oleate, isopropyl myristate, isopropyl palmitate and butyl stearate. Butyl stearate is especially preferred.

When present, one or more oil(s) of formula IX are preferably included in a ratio of total weight of such oil(s) to weight of the cationic exogenous chemical substance, expressed as acid equivalent, of about 1:3 to about 1:100.

Suitable concentrations of an oil of formula IX are about 0.001% to about 1% by weight in a plant treatment composition, and about 0.01% to about 10% by weight in a liquid concentrate composition of the invention.

Oil(s), if present, can be emulsified in a composition of the invention by means of the amphiphilic salt(s) of the exogenous chemical substance. If desired, additional surfactant(s) can be included as emulsifier(s) for such oil(s). It is believed that the presence of oil, especially an oil of formula IX, in the composition can further enhance penetration of the exogenous chemical substance into or through plant cuticles, perhaps as a result of the more lipophilic character imparted to the composition.

The effect of including a suitable oil in a composition of the invention is generally to enlarge the supramolecular aggregates to form swollen micelles or emulsion particles. In such a composition, the mean size of supramolecular aggregates can be within the range defined above for compositions lacking oil, or larger, for example up to about 1000 nm.

Process for Making a Composition of the Invention

Liquid concentrate compositions in accordance with the present invention can be prepared by the following general procedure; however, the invention is not limited to compositions made by this procedure.

In a suitable process, the first step is a neutralizing step. This step comprises neutralization of a first molar amount of an anionic exogenous chemical substance with one or more polyamine(s) or polyamine derivative(s) in a liquid medium, preferably an aqueous medium, with agitation to make a liquid composition containing one or more amphiphilic salt(s) of the exogenous chemical substance. In an example of the neutralizing step where the exogenous chemical substance is glyphosate, a first molar amount of glyphosate acid is added to water together with a molar amount A of a polyamine or polyamine derivative having (a) at least two nitrogen-containing groups, of which a number n not less than 1 are amino groups that can be protonated to form cationic primary, secondary or tertiary ammonium groups, and (b) at least one hydrocarbyl group having about 6 to about 30 carbon atoms. The molar amount nA of amino groups in the polyamine or polyamine derivative added is about 0.5 to about 10, preferably about 0.5 to about 5, and more preferably about 0.5 to about 2, moles per mole of glyphosate, resulting in the making of a monobasic salt, a dibasic salt or a mixture of such monobasic and dibasic salts. The relative molar proportions of monobasic and dibasic salts is a function of the quantity of the polyamine or derivative thereof added per mole of glyphosate.

Optionally the neutralizing step further comprises introducing to the liquid composition, with agitation, a second molar amount of the exogenous chemical substance in the form of one or more salt(s) comprising monovalent cations other than those derived from a polyamine or derivative thereof. In an example of this optional introduction as part of the neutralizing step where the exogenous chemical substance is glyphosate, a second molar amount of glyphosate is added in the form of a monobasic salt, a dibasic salt, or a mixture of such monobasic and dibasic salts comprising such monovalent cations.

The salt(s) of the second molar amount of the exogenous chemical substance can be prepared separately in advance, or made in situ by neutralizing, in the liquid medium with agitation, this second molar amount with one or more monovalent base(s) other than a polyamine or derivative thereof In either case, introduction of such salt(s) can occur before, during or after neutralization of the first molar amount of the exogenous chemical substance.

The neutralizing step takes place with agitation, preferably moderate agitation, for example using a magnetic stirrer. In a preferred embodiment, the neutralizing step is conducted at a temperature higher than the melting point of the polyamine used. Typically the temperature of the liquid medium during the neutralizing step is about 50° C. to about 100° C. However, with certain selected polyamines or derivatives thereof, the neutralization step can satisfactorily be conducted at ambient temperature, for example around 20–25° C.

In a suitable process, the second step is a conditioning step. This step comprises continuing the agitation of the liquid composition until supramolecular aggregates comprising amphiphilic salt(s) of the exogenous chemical substance formed by neutralizing the exogenous chemical substance with a polyamine or derivative thereof are colloidally dispersed in the liquid medium. Agitation, preferably moderate agitation, can be provided, for example, by the same device used to agitate during the neutralizing step. It is preferred, but not required, to maintain an elevated temperature, similar to that provided during the neutralizing step, throughout the conditioning step. The conditioning step can last for a period of about 5 minutes to about 48 hours and results in spontaneous formation of a stable colloidal dispersion of supramolecular aggregates, typically in the form of micelles and larger aggregates as described above.

Optional ingredients other than salt(s) of the exogenous chemical substance can be dissolved or dispersed in the liquid medium prior to, during or after the neutralization step and prior to, during or after the conditioning step. An optimum order of addition can readily be established for any composition by routine experimentation.

In one embodiment, a composition of the invention is prepared by a procedure comprising an acylating step, a neutralizing step and a conditioning step. The acylating step of this embodiment comprises mixing in a suitable vessel a natural oil or fat with a polyamino compound of formula III:

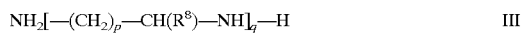

wherein p is 1 to 5, $R^8$ is hydrogen, except where p is 1 in which case $R^8$ is hydrogen or a methyl group, and q is 1 to 4; and heating the resulting mixture with agitation for a sufficient period of time to permit reaction of the oil or fat with the polyamino compound to form a reaction product. Suitable reaction temperatures and times can readily be determined by routine experimentation; in general a satisfactory result can be obtained by heating to a temperature of about 100° C. to about 300° C., preferably about 150° C. to about 250° C., for example around 200° C., for a period of about 1 hour to about 8 hours, for example around 4 hours. Without being bound by theory, it is believed that in this step of the process fatty acyl groups in the oil or fat are transferred from glycerol to amino groups in the polyamino compound, resulting in the formation of hydrocarbamide derivatives of the polyamino compound. Free glycerol and/or partially esterified glycerol derived from the oil or fat remains in the reaction product, which can also contain unreacted starting materials.

The amounts of the oil or fat and of the polyamino compound are selected such that if all acyl groups present in the oil or fat were transferred to amino groups of the polyamino compound, on average at least one amino group of each molecule of the polyamino compound would remain capable of being protonated to form a cationic ammonium group. Preferably the relative amounts of starting materials used are calculated to provide, as the predominant component of the reaction product, a monoacylated polyamine.

In the neutralizing step of this embodiment, a suitable amount of the reaction product of the acylation step is added together with an anionic exogenous chemical substance, for example glyphosate, in a liquid, preferably aqueous, medium with agitation to partially or completely neutralize the anionic exogenous chemical substance. Typically the temperature of the liquid medium during the neutralizing step is about 50° C. to about 100° C.

The conditioning step comprises continuing agitation of the liquid composition resulting from the neutralizing step until supramolecular aggregates comprising amphiphilic salts of the exogenous chemical substance are colloidally dispersed in the liquid medium.

Optionally, in this embodiment, a purification step can be inserted immediately after the acylation step. In the purification step water-soluble compounds formed during the acylation step, principally glycerol, and unreacted polyamino compound are partially or completely removed from the reaction product, by any procedure known in the art. An illustrative procedure comprises adding a mixture of water and organic solvent, e.g., toluene, to the reaction product to form an emulsion, then adding ethanol until the emulsion breaks to form an aqueous phase and an organic phase. If desired, the organic phase can then be washed one or more times with water, each time adding ethanol to break the resulting emulsion. Finally the organic phase is dried, for example over magnesium sulfate, and the solvent is evaporated leaving a residue which can then be used in the neutralizing step.

In a variant of the process just described, a transesterified (e.g., methylated) oil or fat such as methylated soybean oil is used as a starting material in place of the natural oil or fat. In this variant, the acylation step illustratively comprises reacting methylated oil or fat with a polyamino compound of formula III, at a temperature and for a time period similar to that described above. As hydrocarbamide derivatives of the polyamino compound are produced, methanol is released. This can be extracted during the reaction, for example using a Dean-Stark apparatus.

Application of a Contemplated Composition to Foliage

Exogenous chemical substances should be applied to plants at a rate sufficient to give the desired effect. These application rates are usually expressed as amount of exogenous chemical substance per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give, consistently and reliably, at least 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific exogenous chemical substance is within the skill of the ordinary agricultural scientist. Those of skill in the art will likewise recognize that individual plant conditions, weather and growing conditions, as well as the specific exogenous chemical substance and composition thereof selected, will influence the degree of biological effectiveness achieved in practicing this invention. Useful application rates for exogenous chemical substances employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (Kochia scoparia), mallow (Malva spp.), wild buckwheat, smartweed, etc. (Polygonum spp.), purslane (Portulaca spp.), russian thistle (Salsola spp.), sida (Sida spp.), wild mustard (Sinapis arvensis) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, glyphosate compositions of the present invention, and a process for treating plants with such compositions, can be useful on any of the above species. In a particular contemplated process, a plant treatment composition of the invention comprising one or more amphiphilic glyphosate salt(s) is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola and corn.

Application of plant treatment compositions to foliage of plants is preferably accomplished by spraying, using any conventional means for spraying liquids, such as spray nozzles, atomizers, or the like. Compositions of the present invention can be used in precision farming techniques, in which apparatus is employed to vary the amount of exogenous chemical substance applied to different parts of a field, depending on variables such as the particular plant species present, soil composition, and the like. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

A contemplated process for eliciting a desired biological activity in a plant or in a pathogen, parasite or feeding organism present in or on a plant further comprises, prior to the step of applying a plant treatment composition of the invention to foliage of the plant, a step of diluting, in a suitable volume of water, a liquid concentrate composition as provided herein to form the plant treatment composition.

EXAMPLES

The following Examples are provided for illustrative purposes only and are not intended to limit the scope of the present invention. The Examples will permit better understanding of the invention and perception of its advantages and certain variations of execution.

Mole ratios nA/X, i.e., moles of amino groups from polyamine or polyamine derivative compounds per mole of exogenous chemical compound (illustratively glyphosate), given in the following Examples relate to the relative molar amounts added in preparing the compositions of these Examples, and not necessarily to the relative molar amounts present in the finished compositions.

Certain compositions of the Examples are described as containing an N-alkyl or N,N-dialkyl polyamine (see for instance Example 4, "N-lauryl triethylenetetramine", or Example 10, "N,N-distearyl tetraethylenepentamine"). It is to be understood that in these compositions a range of degrees of alkylation is present. Some polyamine molecules present can be non-alkylated; others can carry one alkyl group, others two and still others higher numbers of alkyl groups per polyamine molecule. Thus an N-alkyl polyamine composition in reality contains a mixture in which the average degree of alkylation is 1, while an N,N-alkyl polyamine composition in reality contains a mixture in which the average degree of alkylation is 2. The same concept applies to acylated polyamines, i.e., hydrocarbamide and dihydrocarbamide derivatives (see for instance Example 33, "n-octanamide derivative of tetraethylenepentamine", or Example 45, "distearamide derivative of triethylenetetramine"). Several compositions of the Examples have fractional degrees of alkylation or acylation, such as 1.2 or 1.5, which clearly represent an average of a range of individual degrees of alkylation or acylation.

The term "alkyl", as used conventionally in referring to fatty hydrocarbyl chains derived from natural oils and fats, is to be understood in the Examples herein as encompassing unsaturated as well as saturated chains. Thus, for instance, "cocoalkyl" and "tallowalkyl" relate to hydrocarbyl chains derived respectively from coconut oil (in which the most abundant hydrocarbyl chain is saturated $C_{12}$, i.e., lauryl) and beef tallow (in which the most abundant hydrocarbyl chain is unsaturated $C_{18}$, i.e., oleyl).

The pH values given for compositions of the Examples are not necessarily reproducible. Illustratively, in Example 20, two separate preparations of the same composition, having the same mole ratio of amino groups to glyphosate, but with some differences in process conditions, give markedly different pH values.

Example 1

Glyphosate acid, in the form of a wet cake having a glyphosate assay of 86.5% a.e. by weight, is introduced in an amount of 1.2 g (equivalent to 6.1 mmol) to a 30 ml flask. N-tallowalkyl tripropylenetetramine (Inipol™ PS of CECA), abbreviated in tables herein as "tallow-TPTA" is then added in the amount of 0.8 g. Next, 20 ml of deionized water (ion-exchanged and passed through a 0.2 μm filter) is added to provide an aqueous medium for neutralization of the glyphosate with the N-tallowalkyl tripropylenetetramine.

The flask is stoppered and placed in a water bath at 60° C. for 2 hours. Magnetic agitation is applied to ensure thorough mixing.

A stable colloidal dispersion is obtained which is clear and of low viscosity and has a pH of about 4 when diluted with deionized water to a glyphosate a.e. concentration of 0.5%. The colloidal suspension is characterized by the following procedures.

Stability of the colloidal suspension is determined by observation. If no phase separation appears in the preparation flask upon storage for 48 hours without agitation, at 15° C., the colloidal suspension is considered stable for purposes of the present Example.

The CMC is determined by measuring surface tension at 25° C. over a range of concentrations by the plate method, otherwise known as the Wilhemy method, using a Kruss K12 automatic tensiometer. As the composition is diluted, surface tension initially is largely unaffected. After the CMC is reached, further dilution results in a progressive increase in surface tension, which eventually approaches that of pure water. If, on a graph, surface tension is plotted against concentration on a logarithmic scale, a curve is produced having a sharp break at a particular point below which surface tension is affected and above which surface tension is not or scarcely affected by concentration. The concentration at this break point corresponds to the CMC.

Evidence of micellar structure can be provided by fluorescence spectrometry. The ratio of emission bands $I_1/I_3$, at wavelengths of 373 and 384 nm respectively, obtained using a pyrene probe excited at a wavelength of 332 nm is characteristic of the environment in which the probe is immersed. For example, in a hydrophobic environment such as heptane, $I_1/I_3$=0.6; in a hydrophilic medium, $I_1/I_3$=1.9; and in a micellar state, $I_1/I_3$= 1.2. FIG. 1 shows $I_1/I_3$ as a function of molar concentration, on a logarithmic scale, of the aqueous composition prepared according to Example 1 hereof. The lower $I_1/I_3$ ratio seen at concentrations above about 10 mM is indicative of the amphiphilic salt being in a micellar state.

Results for Example 1 are presented in Table 1 below.

Example 2

The procedure of Example 1 is followed, except that the polyamine used is N-tallowalkyl dipropylenetriamine (Trinoram™ S of CECA), abbreviated in tables herein as "tallow-DPTA". The weight of polyamine introduced is 0.823 g. Results for Example 2 are presented in Table 1 below.

Example 3

The procedure of Example 1 is followed, except that the polyamine used is N-cocoalkyl trimethylenediamine (Dinoram™ C of CECA), abbreviated in tables herein as "coco-TDA". The weight of polyamine introduced is 0.823 g. Results for Example 3 are presented in Table 1 below.

TABLE 1

Results for Examples 1–3

| Example | Polyamine[1] | Mole ratio[2] | Appearance | CMC (μM) | Surface tension at CMC (mN/m) |
|---|---|---|---|---|---|
| 1 | tallow-TPTA | 1.18 | clear | 840 | 32.5 |
| 2 | tallow-DPTA | 1.05 | clear | 120 | 32 |
| 3 | coco-TDA | 1.11 | clear | 160 | 27 |

[1]abbreviations for polyamines can be understood by reference to the Examples.
[2]mole ratio of amino groups to glyphosate a.e. (nA/X); for molecular weight calculation, tallowalkyl considered as $C_{18}H_{35}$ (oleyl), cocoalkyl considered as $C_{12}H_{25}$ (lauryl).

Example 4

N-lauryl triethylenetetramine, abbreviated in tables herein as "1C12-TETA", is synthesized by the following procedure. Into a 1 liter vessel are introduced 50.0 g triethylenetetramine hydrate, purity 98% (Aldrich), 69.0 g 1-bromododecane, purity 95% (Aldrich), 30.0 g sodium bicarbonate and 400 ml ethanol to form a reaction mixture. The reaction mixture is heated at boiling point for 24 hours and then allowed to cool. Salts are removed by filtration and ethanol by distillation. The residue is recovered in a toluene-water mixture, forming an emulsion to which ethanol is added until the emulsion is broken to form separate aqueous and organic phases. After separation of the aqueous phase, the organic phase is washed with water, followed by addition of sufficient ethanol to break the resulting emulsion as in the previous step. The aqueous phase is again separated and the organic phase once again washed with water followed by ethanol addition as before. Finally the organic phase is dried over magnesium sulfate and the solvent is evaporated. The resulting N-lauryl triethylenetetramine residue is dried overnight under vacuum.

A colloidal composition of the invention is prepared by the following procedure. Into a 500 ml screw-capped vial are introduced 19.0 g N-lauryl triethylenetetramine synthesized as above and 12.0 g pure glyphosate acid. Deionized water in an amount of 209.0 g is added to provide an aqueous medium for neutralization of the glyphosate with the N-lauryl triethylenetetramine. The mixture is maintained for a processing time of 4 hours at 50° C. with stirring to ensure neutralizing and conditioning of the mixture to produce a homogeneous turbid composition having a glyphosate a.e. concentration of 5.0% by weight. This is cooled to room temperature.

Example 5

N-stearyl triethylenetetramine, abbreviated in tables herein as "1C18-TETA", is synthesized by a procedure similar to that of Example 4. The reaction mixture consists of 50.0 g triethylenetetramine hydrate, purity 98% (Aldrich), 101.5 g 1-bromooctadecane, purity 96% (Aldrich), 33.3 g sodium bicarbonate and 400 ml ethanol.

A colloidal composition of the invention is then prepared by a procedure similar to that of Example 4, except that 12.0 g pure glyphosate acid is neutralized with 24.0 g N-stearyl triethylenetetramine synthesized as above, in 204.0 g deionized water. Processing time is 2 hours, at 50° C.

Example 6

N,N-distearyl triethylenetetramine, abbreviated in tables herein as "2C18-TETA", is synthesized by a procedure similar to that of Example 4. The reaction mixture consists of 40.0 g technical grade triethylenetetramine, purity 60% (Aldrich), 109.2 g 1-bromooctadecane, purity 96% (Aldrich), 34.5 g sodium bicarbonate and 600 ml ethanol.

A colloidal composition of the invention is then prepared by a procedure similar to that of Example 4, except that 12.0 g pure glyphosate acid is neutralized with 24.6 g N,N-distearyl triethylenetetramine synthesized as above, in 203.4 g deionized water. Processing time is 2 hours, at 60° C.

Example 7

N-(n-octyl) tetraethylenepentamine, abbreviated in tables herein as "1C8-TEPA", is synthesized by a procedure similar to that of Example 4. The reaction mixture consists of 92.0 g tetraethylenepentamine (Aldrich), 50.0 g 1-bromooctane, purity 99% (Aldrich), 28.3 g sodium bicarbonate and 400 ml ethanol.

A colloidal composition of the invention is then prepared by a procedure similar to that of Example 4, except that 12.0 g pure glyphosate acid is neutralized with 8.4 g N-(n-octyl) tetraethylenepentamine synthesized as above, in 219.6 g deionized water. Processing time is 2 hours, at 50° C.

Example 8

N-lauryl tetraethylenepentamine, abbreviated in tables herein as "1C12-TEPA", is synthesized by a procedure similar to that of Example 4. The reaction mixture consists of 71.0 g technical grade tetraethylenepentamine (Aldrich), 50.0 g 1-bromododecane, purity 95% (Aldrich), 25.0 g sodium bicarbonate and 500 ml ethanol.

A colloidal composition of the invention (Example 8a) is then prepared by a procedure similar to that of Example 4, except that 12.0 g pure glyphosate acid is neutralized with 12.6 g N-lauryl tetraethylenepentamine synthesized as above, in 215.4 g deionized water. Processing time is 2 hours, at 50° C.

A second colloidal composition of the invention (Example 8b) is prepared by a similar procedure, except that 16.0 g pure glyphosate acid is neutralized with 16.8 g N-lauryl tetraethylenepentamine synthesized as above, in 287.2 g deionized water. Processing time is 6 hours, at 70° C.

Example 9

N-stearyl tetraethylenepentamine, abbreviated in tables herein as "1C18-TEPA", is synthesized by a procedure similar to that of Example 4. The reaction mixture consists of 73.8 g technical grade tetraethylenepentamine (Aldrich), 104.0 g 1-bromooctadecane, purity 96% (Aldrich), 32.7 g sodium bicarbonate and 400 ml ethanol.

A colloidal composition of the invention is then prepared by a procedure similar to that of Example 4, except that 12.0 g pure glyphosate acid is neutralized with 20.4 g N-stearyl tetraethylenepentamine synthesized as above, in 207.6 g deionized water. Processing time is 3 hours, at 50° C.

Example 10

N,N-distearyl tetraethylenepentamine, abbreviated in tables herein as "2C18-TEPA", is synthesized by a procedure similar to that of Example 4. The reaction mixture consists of 26.4 g technical grade tetraethylenepentamine (Aldrich), 74.5 g 1-bromooctadecane, purity 96% (Aldrich), 23.5 g sodium bicarbonate and 400 ml ethanol.

A colloidal composition of the invention (Example 10a) is then prepared by a procedure similar to that of Example 4, except that 11.8 g pure glyphosate acid is neutralized with 27.5 g N,N-distearyl tetraethylenepentamine synthesized as above, in 200.7 g deionized water. Processing time is 3 hours, at 50° C.

A second colloidal composition of the invention (Example 10b) is prepared by a similar procedure, except that 12.0 g pure glyphosate acid is neutralized with 33.0 g N,N-distearyl tetraethylenepentamine synthesized as above, in 195.0 g deionized water. Processing time is 6 hours, at 60° C.

Example 11

A colloidal composition of the invention (Example 11a) is prepared by a procedure similar to that of Example 4, except that 12.0 g pure glyphosate acid is neutralized with 8.2 g N-cocoalkyl trimethylenediamine (Dinoram™ C of CECA), abbreviated in tables herein as "coco-TDA", in 219.8 g deionized water. Processing time is 2 hours, at 50° C.

A second colloidal composition of the invention (Example 11b) is prepared by a similar procedure, except that 16.0 g pure glyphosate acid is neutralized with 11.7 g N-cocoalkyl trimethylenediamine, in 292.3 g deionized water. Processing time is 1 hour, at 70° C.

Example 12

A colloidal composition of the invention (Example 12a) is prepared by a procedure similar to that of Example 4, except that 12.0 g pure glyphosate acid is neutralized with 10.7 g N-tallowalkyl trimethylenediamine (Inipol™ DS of CECA), abbreviated in tables herein as "tallow-TDA", in 217.3 g deionized water. Processing time is 2 hours, at 50° C.

A second colloidal composition of the invention (Example 12b) is prepared by a similar procedure, except that 16.0 g pure glyphosate acid is neutralized with 14.2 g N-tallowalkyl trimethylenediamine, in 289.8 g deionized water. Processing time is 1 hour, at 70° C.

Example 13

A colloidal composition of the invention (Example 13a) is prepared by a procedure similar to that of Example 4, except that 12.0 g pure glyphosate acid is neutralized with 9.4 g N-stearyl trimethylenediamine (Dinoram™ SH of CECA), abbreviated in tables herein as "1C18-TDA", in 218.6 g deionized water. Processing time is 2 hours, at 50° C.

A second colloidal composition of the invention (Example 13b) is prepared by a similar procedure, except that 16.0 g pure glyphosate acid is neutralized with 12.6 g N-stearyl trimethylenediamine, in 291.4 g deionized water. Processing time is 1 hour, at 70° C.

Example 14

A colloidal composition of the invention (Example 14a) is prepared by a procedure similar to that of Example 4, except that 12.0 g pure glyphosate acid is neutralized with 9.6 g N-tallowalkyl dipropylenetriamine (Trinoram™ S of CECA), abbreviated in tables herein as "tallow-DPTA", in 218.4 g deionized water. Processing time is 2 hours, at 50° C.

A second colloidal composition of the invention (Example 14b) is prepared by a similar procedure, except that 16.0 g pure glyphosate acid is neutralized with 12.8 g N-tallowalkyl dipropylenetriamine, in 296 g deionized water. Processing time is 1 hour, at 70° C.

Example 15

A colloidal composition of the invention is prepared by a procedure similar to that of Example 4, except that 12.0 g pure glyphosate acid is neutralized with 7.2 g N-cocoalkyl dipropylenetriamine (Trinoram™ C of CECA), abbreviated in tables herein as "coco-DPTA", in 220.8 g deionized water. Processing time is 2 hours, at 50° C.

Example 16

N-lauryl butylenediamine, abbreviated in tables herein as "1C12-BDA", is synthesized by a procedure similar to that of Example 4. The reaction mixture consists of 50.0 g 1,4-diaminobutane, purity 99% (Aldrich), 141.5 g 1-bromododecane, purity 97% (Aldrich), 60.0 g sodium bicarbonate and 400 ml ethanol.

A colloidal composition of the invention is then prepared by a procedure similar to that of Example 4, except that 12.0 g pure glyphosate acid is neutralized with 12.8 g N-lauryl butylenediamine synthesized as above, in 215.2 g deionized water. Processing time is 2 hours, at 50° C.

Example 17

N-stearyl butylenediamine, abbreviated in tables herein as "1C18-BDA", is synthesized by a procedure similar to that of Example 4. The reaction mixture consists of 50.0 g 1,4-diaminobutane, purity 99% (Aldrich), 172.0 g 1-bromooctadecane, purity 96% (Aldrich), 54.2 g sodium bicarbonate and 400 ml ethanol.

A colloidal composition of the invention is then prepared by a procedure similar to that of Example 4, except that 12.1 g pure glyphosate acid is neutralized with 26.9 g N-stearyl butylenediamine synthesized as above, in 201.0 g deionized water. Processing time is 3 hours, at 60° C.

Example 18

N-lauryl hexamethylenediamine, abbreviated in tables herein as "1C12-HDA", is synthesized by a procedure similar to that of Example 4. The reaction mixture consists of 30.0 g 1,6-diaminohexane (hexamethylenediamine), purity 98% (Aldrich), 64.4 g 1-bromododecane, purity 95% (Aldrich), 27.2 g sodium bicarbonate and 400 ml ethanol.

A colloidal composition of the invention (Example 18a) is then prepared by a procedure similar to that of Example 4, except that 11.5 g pure glyphosate acid is neutralized with 14.1 g N-lauryl hexamethylenediamine synthesized as above, in 209.4 g deionized water. Processing time is 3 hours, at 50° C.

A second colloidal composition of the invention (Example 18b) is prepared by a similar procedure, except that 13.0 g pure glyphosate acid is neutralized with 26.1 g N-lauryl hexamethylenediamine synthesized as above, in 220.9 g deionized water. Processing time is 5 hours, at 60° C.

Example 19

N-(n-decyl) bis(hexamethylene)triamine, abbreviated in tables herein as "1C10-DHTA", is synthesized by a procedure similar to that of Example 4. The reaction mixture consists of 51.4 g bis(hexamethylene)triamine, purity 99% (Aldrich), 50.0 g 1-bromodecane, purity 97% (Aldrich), 25.0 g sodium bicarbonate and 400 ml ethanol.

A colloidal composition of the invention is then prepared by a procedure similar to that of Example 4, except that 12.0 g pure glyphosate acid is neutralized with 13.8 g N-(n-decyl) bis(hexamethylene)triamine synthesized as above, in 214.2 g deionized water. Processing time is 2 hours, at 60° C.

Example 20

N-lauryl bis(hexamethylene)triamine, abbreviated in tables herein as "1C12-DHTA", is synthesized by a procedure similar to that of Example 4. The reaction mixture consists of 50.0 g bis(hexamethylene)triamine, purity 99% (Aldrich), 57.0 g 1-bromododecane, purity 95% (Aldrich), 24.4 g sodium bicarbonate and 400 ml ethanol.

A colloidal composition of the invention (Example 20a) is then prepared by a procedure similar to that of Example 4, except that 12.0 g pure glyphosate acid is neutralized with 11.0 g N-lauryl bis(hexamethylene)triamine synthesized as above, in 217.0 g deionized water. Processing time is 2 hours, at 60° C.

A second colloidal composition of the invention (Example 20b) is prepared by a similar procedure, except that 9.0 g pure glyphosate acid is neutralized with 8.3 g N-lauryl bis(hexamethylene)triamine synthesized as above, in 162.7 g deionized water. Processing time is 4 hours, at 70° C.

Example 21

N,N-dilauryl triethylenetetramine, abbreviated in tables herein as "2C12-TETA", is synthesized by a procedure similar to that of Example 4. The reaction mixture consists of 50.0 g technical grade triethylenetetramine, purity 60% (Aldrich), 102.3 g 1-bromododecane, purity 97% (Aldrich), 43.0 g sodium bicarbonate and 500 ml ethanol.

A colloidal composition of the invention is then prepared by a procedure similar to that of Example 4, except that 12.0 g pure glyphosate acid is neutralized with 14.3 g N,N-dilauryl triethylenetetramine synthesized as above, in 213.7 g deionized water. Processing time is 3 hours, at 60° C.

Example 22

N-myristyl hexamethylenediamine, abbreviated in tables herein as "1C14-HDA", is synthesized by a procedure similar to that of Example 4. The reaction mixture consists of 64.0 g 1,6-diaminohexane (hexamethylenediamine), purity 98% (Aldrich), 140.0 g 1-bromotetradecane, purity 97% (Aldrich), 53.0 g sodium bicarbonate and 400 ml ethanol.

A colloidal composition of the invention is then prepared by a procedure similar to that of Example 4, except that 12.0 g pure glyphosate acid is neutralized with 18.9 g N-myristyl hexamethylenediamine synthesized as above, in 209.1 g deionized water. Processing time is 3 hours, at 60° C.

Example 23

An N-(n-octenyl)succinimide derivative of hexamethylenediamine, abbreviated in tables herein as "1C8=S-HDA", is synthesized by the following procedure. Into a 1 liter vessel are introduced 54.8 g hexamethylenediamine, purity 98% (Aldrich), 100.0 g octenylsuccinic anhydride (Unipex) and 400 ml xylene to form a reaction mixture. The reaction mixture is heated at boiling point for 48 hours. The water (10 ml) generated during formation of the succinimide is extracted during the reaction using a Dean-Stark apparatus. The xylene is then evaporated and the resulting residue, 135 g of an N-(n-octenyl) succinimide derivative of hexamethylenediamine, is recovered.

A colloidal composition of the invention is prepared by the following procedure. Into a 500 ml screw-capped vial are introduced 65.0 g N-(n-octenyl)succinimide derivative of hexamethylenediamine synthesized as above and 12.0 g pure glyphosate acid. Deionized water in an amount of 163.0 g is added to provide an aqueous medium for neutralization of the glyphosate with the N-(n-octenyl)succinimide derivative of hexamethylenediamine. The mixture is maintained for a processing time of 3 hours at 60° C. with stirring to ensure neutralizing and conditioning of the mixture to produce a homogeneous turbid composition having a glyphosate a.e. concentration of 5.0% by weight. This is cooled to room temperature.

Example 24

A mixture of lauramide derivatives of diethylenetriamine having a lauroyl to diethylenetriamine mole ratio of 1.5:1, abbreviated in tables herein as "1.5C11-CO-DETA", is synthesized by the following procedure. Into a 250 ml vessel are introduced 15.0 g diethylenetriamine, purity 99% (Aldrich) and 47.2 g methyl laurate, purity 98% (Aldrich) to form a reaction mixture. The reaction mixture is heated at 200° C. for 4 hours. The methanol (10 ml) generated during formation of the amide is extracted during the reaction using a Dean-Stark apparatus.

A colloidal composition of the invention is then prepared by a procedure similar to that of Example 4, except that 12.0 g pure glyphosate acid is neutralized with 27.6 g of the diethylenetriamine derivatives mixture synthesized as above, in 200.4 g deionized water. Processing time is 3 hours, at 50° C.

Example 25

A mixture of oleamide derivatives of diethylenetriamine having an oleoyl to diethylenetriamine mole ratio of 1.2:1, abbreviated in tables herein as "1.2C17=CO-DETA", is synthesized by a procedure similar to that of Example 24. The reaction mixture consists of 35.0 g diethylenetriamine, purity 99% (Aldrich) and 121.7 g methyl oleate, purity 98% (Aldrich).

A colloidal composition of the invention is then prepared by a procedure similar to that of Example 4, except that 12.0 g pure glyphosate acid is neutralized with 44.3 g of the diethylenetriamine derivatives mixture synthesized as above, in 183.7 g deionized water. Processing time is 5 hours, at 50° C.

Example 26

A mixture of n-decanamide derivatives of triethylenetetramine having an n-decanoyl to triethylenetetramine mole ratio of 1.2:1, abbreviated in tables herein as "1.2C9-CO-TETA", is synthesized by a procedure similar to that of Example 24. The reaction mixture consists of 32.7 g triethylenetetramine htydrate, purity 98% (Aldrich) and 50.0 g methyl n-decanoate, purity 99% (Aldrich).

A colloidal composition of the invention is then prepared by a procedure similar to that of Example 4, except that 12.0 g pure glyphosate acid is neutralized with 11.0 g of the triethylenetetramine derivatives mixture synthesized as above, in 217.0 g deionized water. Processing time is 5 hours, at 50° C.

Example 27

A di(n-decanamide) derivative of triethylenetetramine, abbreviated in tables herein as "2C9-CO-TETA", is synthesized by a procedure similar to that of Example 24. The reaction mixture consists of 31.4 g triethylenetetramine hydrate, purity 98% (Aldrich) and 80.0 g methyl n-decanoate, purity 99% (Aldrich).

A colloidal composition of the invention is then prepared by a procedure similar to that of Example 4, except that 12.0 g pure glyphosate acid is neutralized with 31.6 g of the triethylenetetramine derivative synthesized as above, in 196.4 g deionized water. Processing time is 5 hours, at 50° C.

Example 28

A dilauramide derivative of triethylenetetramine, abbreviated in tables herein as "2C11-CO-TETA", is synthesized by a procedure similar to that of Example 24. The reaction mixture consists of 20.0 g triethylenetetramine hydrate, purity 98% (Aldrich) and 58.7 g methyl laurate, purity 98% (Aldrich).

A colloidal composition of the invention is then prepared by a procedure similar to that of Example 4, except that 12.0 g pure glyphosate acid is neutralized with 33.5 g of the triethylenetetramine derivative synthesized as above, in 196 g deionized water. Processing time is 5 hours, at 50° C.

Example 29

A mixture of stearamide derivatives of triethylenetetramine having a stearoyl to triethylenetetramine mole ratio of 1.2:1, abbreviated in tables herein as "1.2C17-CO-TETA", is synthesized by a procedure similar to that of Example 24. The reaction mixture consists of 30.0 g triethylenetetramine hydrate, purity 98% (Aldrich) and 65.5 g methyl stearate, purity 98% (Aldrich).

A colloidal composition of the invention is then prepared by a procedure similar to that of Example 4, except that 12.0 g pure glyphosate acid is neutralized with 24.0 g of the triethylenetetramine derivatives mixture synthesized as above, in 204.0 g deionized water. Processing time is 5 hours, at 50° C.

Example 30

A mixture of stearamide derivatives of triethylenetetramine having a stearoyl to triethylenetetramine mole ratio of 1.5:1, abbreviated in tables herein as "1.5C17-CO-TETA", is synthesized by a procedure similar to that of Example 24. The reaction mixture consists of 19.6 g triethylenetetramine hydrate, purity 98% (Aldrich) and 60.0 g methyl stearate, purity 98% (Aldrich).

A colloidal composition of the invention is then prepared by a procedure similar to that of Example 4, except that 12.0 g pure glyphosate acid is neutralized with 31.4 g of the triethylenetetramine derivatives mixture synthesized as above, in 196.6 g deionized water. Processing time is 5 hours, at 50° C.

Example 31

A mixture of oleamide derivatives of triethylenetetramine having a oleoyl to triethylenetetramine mole ratio of 1.2:1, abbreviated in tables herein as "1.2C17=CO-TETA", is synthesized by a procedure similar to that of Example 24. The reaction mixture consists of 28.7 g triethylenetetramine hydrate, purity 98% (Aldrich) and 100.0 g methyl oleate, purity 98% (Aldrich).

A colloidal composition of the invention (Example 31a) is then prepared by a procedure similar to that of Example 4, except that 12.0 g pure glyphosate acid is neutralized with 41.2 g of the triethylenetetramine derivatives mixture synthesized as above, in 186.4 g deionized water. Processing time is 5 hours, at 50° C.

A second colloidal composition of the invention (Example 31b) is prepared by a similar procedure, except that 6.1 g pure glyphosate acid is neutralized with 20.6 g of the triethylenetetramine derivatives mixture synthesized as above, in 93.3 g deionized water. Processing time is 5 hours, at 60° C.

Example 32

A mixture of n-decanamide derivatives of tetraethylenepentamine having an n-decanoyl to tetraethylenepentamine mole ratio of 1.2:1, abbreviated in tables herein as "1.2C9-CO-TEPA", is synthesized by a procedure similar to that of Example 24. The reaction mixture consists of 84.5 g technical grade tetraethylenepentamine (Aldrich) and 100.0 g methyl n-decanoate, purity 99% (Aldrich).

A colloidal composition of the invention is then prepared by a procedure similar to that of Example 4, except that 12.0 g pure glyphosate acid is neutralized with 7.3 g of the tetraethylenepentamine derivatives mixture synthesized as above, in 220.7 g deionized water. Processing time is 3 hours, at 50° C.

Example 33

An n-octanamide derivative of tetraethylenepentamine, abbreviated in tables herein as "1C7-CO-TEPA", is synthesized by a procedure similar to that of Example 24. The reaction mixture consists of 64.0 g technical grade tetraethylenepentamine (Aldrich) and 53.4 g methyl n-octanoate, 98% (Aldrich).

A colloidal composition of the invention is then prepared by a procedure similar to that of Example 4, except that 12.0 g pure glyphosate acid is neutralized with 8.2 g of the tetraethylenepentamine derivative synthesized as above, in 219.8 g deionized water. Processing time is 4 hours, at 50° C.

Example 34

A mixture of n-decanamide derivatives of tetraethylenepentamine having an n-decanoyl to tetraethylenepentamine mole ratio of 1.5:1, abbreviated in tables herein as "1.5C9-CO-TEPA", is synthesized by a procedure similar to that of Example 24. The reaction mixture consists of 20.4 g technical grade tetraethylenepentamine (Aldrich) and 30.0 g methyl n-decanoate, purity 99% (Aldrich).

A colloidal composition of the invention is then prepared by a procedure similar to that of Example 4, except that 12.0 g pure glyphosate acid is neutralized with 11.0 g of the tetraethylenepentamine derivatives mixture synthesized as above, in 217.0 g deionized water. Processing time is 5 hours, at 50° C.

Example 35

A di(n-decanamide) derivative of tetraethylenepentamine, abbreviated in tables herein as "2C9-CO-TEPA", is synthesized by a procedure similar to that of Example 24. The reaction mixture consists of 29.8 g technical grade tetraethylenepentamine (Aldrich) and 58.7 g methyl n-decanoate, purity 99% (Aldrich).

A colloidal composition of the invention is then prepared by a procedure similar to that of Example 4, except that 12.0 g pure glyphosate acid is neutralized with 14.2 g of the tetraethylenepentamine derivative synthesized as above, in 215 g deionized water. Processing time is 5 hours, at 50° C.

Example 36

A mixture of lauramide derivatives of tetraethylenepentamine having a lauroyl to tetraethylenepentamine mole ratio of 1.2:1, abbreviated in tables herein as "1.2C11-CO-TEPA", is synthesized by a procedure similar to that of Example 24. The reaction mixture consists of 56.7 g technical grade tetraethylenepentamine (Aldrich) and 64.7 g methyl laurate, purity 99.5% (Aldrich).

A colloidal composition of the invention is then prepared by a procedure similar to that of Example 4, except that 12.0 g pure glyphosate acid is neutralized with 14.2 g of the tetraethylenepentamine derivatives mixture synthesized as above, in 215 g deionized water. Processing time is 5 hours, at 50° C.

Example 37

A dilauramide derivative of tetraethylenepentamine, abbreviated in tables herein as "2C11-CO-TEPA", is synthesized by a procedure similar to that of Example 24. The reaction mixture consists of 30.0 g technical grade tetraethylenepentamine (Aldrich) and 67.8 g methyl laurate, purity 99.5% (Aldrich).

A colloidal composition of the invention is then prepared by a procedure similar to that of Example 4, except that 12.0 g pure glyphosate acid is neutralized with 17.1 g of the tetraethylenepentamine derivative synthesized as above, in 210.5 g deionized water. Processing time is 5 hours, at 50° C.

Example 38

A mixture of oleamide derivatives of tetraethylenepentamine having a oleoyl to tetraethylenepentamine mole ratio of 1.2:1, abbreviated in tables herein as "1.2C17=CO-TEPA", is synthesized by a procedure similar to that of Example 24. The reaction mixture consists of 37.3 g technical grade tetraethylenepentamine (Aldrich) and 100.0 g technical grade methyl oleate, purity 70% (Aldrich).

A colloidal composition of the invention is then prepared by a procedure similar to that of Example 4, except that 12.0 g pure glyphosate acid is neutralized with 23.1 g of the tetraethylenepentamine derivatives mixture synthesized as above, in 204.8 g deionized water. Processing time is 5 hours, at 50° C.

Example 39

A mixture of oleamide derivatives of tetraethylenepentamine having a oleoyl to tetraethylenepentamine mole ratio of 1.5:1, abbreviated in tables herein as "1.5C17=CO-TEPA", is synthesized by a procedure similar to that of Example 24. The reaction mixture consists of 29.8 g technical grade tetraethylenepentamine (Aldrich) and 67.8 g technical grade methyl oleate, purity 70% (Aldrich).

A colloidal composition of the invention is then prepared by a procedure similar to that of Example 4, except that 12.0 g pure glyphosate acid is neutralized with 32.9 g of the tetraethylenepentamine derivatives mixture synthesized as above, in 194.8 g deionized water. Processing time is 5 hours, at 50° C.

Example 40

A mixture of stearamide derivatives of tetraethylenepentamine having a stearoyl to tetraethylenepentamine mole ratio of 1.5:1, abbreviated in tables herein as "1.5C17-CO-TEPA", is synthesized by a procedure similar to that of Example 24. The reaction mixture consists of 25.4 g technical grade tetraethylenepentamine (Aldrich) and 60.0 g methyl stearate, purity 97% (Aldrich).

A colloidal composition of the invention is then prepared by a procedure similar to that of Example 4, except that 12.0 g pure glyphosate acid is neutralized with 23.6 g of the tetraethylenepentamine derivatives mixture synthesized as above, in 204.4 g deionized water. Processing time is 3 hours, at 60° C.

Example 41

A dioleamide derivative of tetraethylenepentamine, abbreviated in tables herein as "2C17=CO-TEPA", is synthesized by a procedure similar to that of Example 24. The reaction mixture consists of 22.4 g technical grade tetraethylenepentamine (Aldrich) and 100.0 g technical grade methyl oleate, purity 70% (Aldrich).

A colloidal composition of the invention is then prepared by a procedure similar to that of Example 4, except that 12.0 g pure glyphosate acid is neutralized with 35.3 g of the tetraethylenepentamine derivative synthesized as above, in 192.4 g deionized water. Processing time is 5 hours, at 50° C.

Example 42

A distearamide derivative of tetraethylenepentamine, abbreviated in tables herein as "2C17-CO-TEPA", is synthesized by a procedure similar to that of Example 24. The reaction mixture consists of 18.9 g technical grade tetraethylenepentamine (Aldrich) and 60.0 g methyl stearate, purity 97% (Aldrich).

A colloidal composition of the invention is then prepared by a procedure similar to that of Example 4, except that 12.0 g pure glyphosate acid is neutralized with 46.0 g of the tetraethylenepentamine derivative synthesized as above, in 341.7 g deionized water. Processing time is 3 hours, at 60° C.

Example 43

A mixture of n-octanamide derivatives of bis(hexamethylene)triamine having an n-octanoyl to bis(hexamethylene)triamine mole ratio of 1.2:1, abbreviated in tables herein as "1.2C7-CO-DHTA", is synthesized by a procedure similar to that of Example 24. The reaction mixture consists of 52.8 g bis(hexamethylene)triamine, purity 99% (Aldrich) and 46.6 g methyl n-octanoate, purity 99% (Aldrich).

A colloidal composition of the invention is then prepared by a procedure similar to that of Example 4, except that 12.0 g pure glyphosate acid is neutralized with 39.4 g of the bis(hexamethylene)triamine derivatives mixture synthesized as above, in 188.3 g deionized water. Processing time is 3 hours, at 50° C.

Example 44

A distearamide derivative of triethylenetetramine, abbreviated in tables herein as "2C17-CO-TETA", is synthesized by a procedure similar to that of Example 24. The reaction mixture consists of 20.0 g triethylenetetramine hydrate, purity 98% (Aldrich) and 72.3 g methyl stearate, purity 97% (Aldrich).

A colloidal composition of the invention is then prepared by a procedure similar to that of Example 4, except that 12.0 g pure glyphosate acid is neutralized with 24.7 g of the triethylenetetramine derivative synthesized as above, in 203.3 g deionized water. Processing time is 3 hours, at 60° C.

Example 45

A dioleamide derivative of triethylenetetramine, abbreviated in tables herein as "2C17=CO-TETA", is synthesized by a procedure similar to that of Example 24. The reaction mixture consists of 29.0 g technical grade triethylenetetramine, purity 60% (Aldrich) and 100.0 g technical grade methyl oleate, purity 70% (Aldrich).

A colloidal composition of the invention is then prepared by a procedure similar to that of Example 4, except that 12.0 g pure glyphosate acid is neutralized with 37.0 g of the triethylenetetramine derivative synthesized as above, in 191.0 g deionized water. Processing time is 3 hours, at 60° C.

Example 46

A mixture of oleamide derivatives of triethylenetetramine having an oleoyl to triethylenetetramine mole ratio of 1.2:1, abbreviated in tables herein as "1.2C17=CO-TETA", is synthesized by the following procedure. Into a 500 ml vessel are introduced 81.2 g technical grade triethylenetetramine, purity 60% (Aldrich) and 169.0 g technical grade methyl oleate, purity 70% (Aldrich) to form a reaction mixture. The reaction mixture is heated at 200° C. for 4 hours. The methanol (24 ml) generated during formation of the amide is extracted during the reaction using a Dean-Stark apparatus. The product of the reaction is recovered in a toluene-water mixture, forming an emulsion to which ethanol is added until the emulsion is broken to form separate aqueous and organic phases. After separation of the aqueous phase, the organic phase is washed with water, followed by addition of sufficient ethanol to break the resulting emulsion as in the previous step. The aqueous phase is again separated and the organic phase once again washed with water followed by ethanol addition as before. Finally the organic phase is dried over magnesium sulfate and the solvent is evaporated. The resulting product is dried overnight under vacuum.

A colloidal composition of the invention is then prepared by a procedure similar to that of Example 4, except that 12.0 g pure glyphosate acid is neutralized with 31.2 g of the purified triethylenetetramine derivatives mixture synthesized as above, in 196.6 g deionized water. Processing time is 5 hours, at 50° C.

Example 47

A crude cocoamide derivative of triethylenetetramine, abbreviated in tables herein as "coco-CO-TETA", in which the acyl groups are derived from coconut oil, is synthesized by the following procedure. Into a 250 ml vessel are introduced 54.5 g technical grade triethylenetetramine, purity 60% (Aldrich) and 48.8 g coconut oil (Aldrich), to form a reaction mixture. The reaction mixture is heated at 200° C. for 4 hours.

A colloidal composition of the invention is then prepared by a procedure similar to that of Example 4, except that 11.4 g pure glyphosate acid is neutralized with 9.2 g of the crude triethylenetetramine derivative synthesized as above, in 99 g deionized water. Processing time is 15 minutes at 25° C. followed by 45 minutes at 70° C.

Example 48

A crude palmamide derivative of triethylenetetramine, abbreviated in tables herein as "palm-CO-TETA", in which the acyl groups are derived from palm oil, is synthesized by a procedure similar to that of Example 47. The reaction mixture consists of 48.6 g technical grade triethylenetetramine, purity 60% (Aldrich) and 56.0 g palm oil (Aldrich).

A colloidal composition of the invention is then prepared by a procedure similar to that of Example 4, except that 11.3 g pure glyphosate acid is neutralized with 11.1 g of the crude triethylenetetramine derivative synthesized as above, in 97 g deionized water. Processing time is 15 minutes at 25° C. followed by 45 minutes at 70° C.

Example 49

A crude castoramide derivative of triethylenetetramine, abbreviated in tables herein as "castor-CO-TETA", in which the acyl groups are derived from castor oil, is synthesized by a procedure similar to that of Example 47. The reaction mixture consists of 48.6 g technical grade triethylenetetramine, purity 60% (Aldrich) and 62.0 g castor oil (ProLabo).

A colloidal composition of the invention is then prepared by a procedure similar to that of Example 4, except that 11.3 g pure glyphosate acid is neutralized with 11.8 g of the crude triethylenetetramine derivative synthesized as above, in 97 g deionized water. Processing time is 15 minutes, at 25° C.

Example 50

A crude oliveamide derivative of triethylenetetramine, abbreviated in tables herein as "olive-CO-TETA", in which the acyl groups are derived from olive oil, is synthesized by a procedure similar to that of Example 47. The reaction mixture consists of 34.8 g technical grade triethylenetetramine, purity 60% (Aldrich) and 41.5 g olive oil (Croda).

A colloidal composition of the invention is then prepared by a procedure similar to that of Example 4, except that 11.3 g pure glyphosate acid is neutralized with 11.8 g of the crude triethylenetetramine derivative synthesized as above, in 97 g deionized water. Processing time is 15 minutes at 25° C. followed by 45 minutes at 70° C.

Example 51

A crude oliveamide derivative of tetraethylenepentamine, abbreviated in tables herein as "olive-CO-TEPA", in which the acyl groups are derived from olive oil, is synthesized by a procedure similar to that of Example 47. The reaction mixture consists of 40.0 g technical grade tetraethylenepentamine (Aldrich) and 49.2 g olive oil (Puget).

A colloidal composition of the invention is then prepared by a procedure similar to that of Example 4, except that 11.3 g pure glyphosate acid is neutralized with 13.2 g of the crude tetraethylenepentamine derivative synthesized as above, in 95 g deionized water. Processing time is 15 minutes, at 25° C.

Example 52

A crude palmamide derivative of tetraethylenepentamine, abbreviated in tables herein as "palm-CO-TEPA", in which the acyl groups are derived from palm oil, is synthesized by a procedure similar to that of Example 47. The reaction mixture consists of 40.0 g technical grade tetraethylenepentamine (Aldrich) and 47.4 g palm oil (Aldrich).

A colloidal composition of the invention is then prepared by a procedure similar to that of Example 4, except that 11.3 g pure glyphosate acid is neutralized with 11.8 g of the crude tetraethylenepentamine derivative synthesized as above, in 97 g deionized water. Processing time is 15 minutes at 25° C. followed by 60 minutes at 70° C.

Example 53

A crude castoramide derivative of tetraethylenepentamine, abbreviated in tables herein as "castor-CO-TEPA", in which the acyl groups are derived from castor oil, is synthesized by a procedure similar to that of Example 47. The reaction mixture consists of 40.0 g technical grade tetraethylenepentamine (Aldrich) and 52.7 g castor oil (Aldrich).

A colloidal composition of the invention is then prepared by a procedure similar to that of Example 4, except that 11.3 g pure glyphosate acid is neutralized with 13.1 g of the crude tetraethylenepentamine derivative synthesized as above, in 95 g deionized water. Processing time is 15 minutes, at 25° C.

Example 54

A crude cocoamide derivative of tetraethylenepentamine, abbreviated in tables herein as "coco-CO-TEPA", in which the acyl groups are derived from coconut oil, is synthesized by a procedure similar to that of Example 47. The reaction mixture consists of 43.2 g technical grade tetraethylenepentamine (Aldrich) and 40.0 g coconut oil (Aldrich).

A colloidal composition of the invention is then prepared by a procedure similar to that of Example 4, except that 11.5 g pure glyphosate acid is neutralized with 11.2 g of the crude tetraethylenepentamine derivative synthesized as above, in 97 g deionized water. Processing time is 6 minutes, at 70° C.

Example 55

A crude cocoamide derivative of trimethylenediamine, abbreviated in tables herein as "coco-CO-TDA", in which the acyl groups are derived from coconut oil, is synthesized by a procedure similar to that of Example 47. The reaction mixture consists of 20.0 g trimethylenediamine, purity 99% (Aldrich) and 59.0 g coconut oil (Aldrich).

A colloidal composition of the invention is then prepared by a procedure similar to that of Example 4, except that 11.5 g pure glyphosate acid is neutralized with 11.2 g of the crude trimethylenediamine derivative synthesized as above, in 97 g deionized water. Processing time is 2 hours, at 50° C.

Example 56

A crude cocoamide derivative of dipropylenetriamine, abbreviated in tables herein as "coco-CO-DPTA", in which the acyl groups are derived from coconut oil, is synthesized by a procedure similar to that of Example 47. The reaction mixture consists of 30.0 g dipropylenetriamine, purity 99% (Aldrich) and 50.0 g coconut oil (Aldrich).

A colloidal composition of the invention is then prepared by a procedure similar to that of Example 4, except that 11.5 g pure glyphosate acid is neutralized with 16.8 g of the crude dipropylenetriamine derivative synthesized as above, in 92 g deionized water. Processing time is 2 hours, at 70° C.

Example 57

A crude castoramide derivative of dipropylenetriamine, abbreviated in tables herein as "castor-CO-DPTA", in which the acyl groups are derived from castor oil, is synthesized by a procedure similar to that of Example 47. The reaction mixture consists of 25.0 g dipropylenetriamine, purity 99% (Aldrich) and 59.3 g castor oil (Aldrich).

A colloidal composition of the invention is then prepared by a procedure similar to that of Example 4, except that 11.5 g pure glyphosate acid is neutralized with 22.5 g of the crude dipropylenetriamine derivative synthesized as above, in 86.0 g deionized water. Processing time is 2 hours, at 70° C.

Example 58

A crude cocoamide derivative of butylenediamine, abbreviated in tables herein as "coco-CO-BDA", in which the acyl groups are derived from coconut oil, is synthesized by a procedure similar to that of Example 47. The reaction mixture consists of 25.0 g butylenediamine, purity 99% (Aldrich) and 62.0 g coconut oil (Aldrich).

A colloidal composition of the invention is then prepared by a procedure similar to that of Example 4, except that 11.6 g pure glyphosate acid is neutralized with 34.2 g of the crude butylenediamine derivative synthesized as above, in 74 g deionized water. Processing time is 2 hours at 70° C. followed by 16 hours at 25° C.

Example 59

A crude palmamide derivative of hexamethylenediamine, abbreviated in tables herein as "palm-CO-HDA", in which the acyl groups are derived from palm oil, is synthesized by a procedure similar to that of Example 47. The reaction mixture consists of 46.7 g hexamethylenediamine, purity 99% (Aldrich) and 103.0 g palm oil (Aldrich).

A colloidal composition of the invention is then prepared by a procedure similar to that of Example 4, except that 11.5 g pure glyphosate acid is neutralized with 36.5 g of the crude hexamethylenediamine derivative synthesized as above, in 192.0 g deionized water. Processing time is 4 hours at 70° C. followed by 16 hours at 25° C.

Example 60

A crude cocoamide derivative of hexamethylenediamine, abbreviated in tables herein as "coco-CO-HDA", in which the acyl groups are derived from coconut oil, is synthesized by a procedure similar to that of Example 47. The reaction mixture consists of 46.7 g hexamethylenediamine, purity 99% (Aldrich) and 50.0 g coconut oil (Aldrich).

A colloidal composition of the invention is then prepared by a procedure similar to that of Example 4, except that 11.5 g pure glyphosate acid is neutralized with 29.2 g of the crude hexamethylenediamine derivative synthesized as above, in 79 g deionized water. Processing time is 3 hours, at 70° C.

Example 61

A crude palmamide derivative of bis(hexamethylene) triamine, abbreviated in tables herein as "palm-CO-DHTA", in which the acyl groups are derived from palm oil, is synthesized by a procedure similar to that of Example 47. The reaction mixture consists of 60.0 g bis(hexamethylene) triamine, purity 99% (Aldrich) and 80.0 g palm oil (Aldrich).

A colloidal composition of the invention is then prepared by a procedure similar to that of Example 4, except that 12.0 g pure glyphosate acid is neutralized with 25.9 g of the crude bis(hexamethylene)triamine derivative synthesized as above, in 202.1 g deionized water. Processing time is 5 hours, at 70° C.

Example 62

A crude castoramide derivative of bis(hexamethylene) triamine, abbreviated in tables herein as "castor-CO-DHTA", in which the acyl groups are derived from castor oil, is synthesized by a procedure similar to that of Example 47. The reaction mixture consists of 40.0 g bis (hexamethylene)triamine, purity 99% (Aldrich) and 57.8 g castor oil (Aldrich).

A colloidal composition of the invention is then prepared by a procedure similar to that of Example 4, except that 1.5 g pure glyphosate acid is neutralized with 26.6 g of the crude bis(hexamethylene)triamine derivative synthesized as above, in 82 g deionized water. Processing time is 6 hours, at 70° C.

Example 63

A crude cocoamide derivative of bis(hexamethylene) triamine, abbreviated in tables herein as "coco-CO-DHTA", in which the acyl groups are derived from coconut oil, is synthesized by a procedure similar to that of Example 47. The reaction mixture consists of 30.0 g bis(hexamethylene) triamine, purity 99% (Aldrich) and 35.0 g coconut oil (Aldrich).

A colloidal composition of the invention is then prepared by a procedure similar to that of Example 4, except that 11.5 g pure glyphosate acid is neutralized with 23.8 g of the crude bis(hexamethylene)triamine derivative synthesized as above, in 85 g deionized water. Processing time is 5 hours, at 70° C.

Example 64

A crude oliveamide derivative of bis(hexamethylene) triamine, abbreviated in tables herein as "olive-CO-DHTA", in which the acyl groups are derived from olive oil, is synthesized by a procedure similar to that of Example 47. The reaction mixture consists of 35.0 g bis(hexamethylene) triamine, purity 99% (Aldrich) and 47.0 g olive oil (Aldrich).

A colloidal composition of the invention is then prepared by a procedure similar to that of Example 4, except that 12.0 g pure glyphosate acid is neutralized with 28.6 g of the crude bis(hexamethylene)triamine derivative synthesized as above, in 199 g deionized water. Processing time is 9 hours, at 60° C.

Example 65

A soyamide derivative of tetraethylenepentamine, abbreviated in tables herein as "soy-CO-TEPA", in which the acyl groups are derived from soybean oil, is synthesized by the following procedure. Into a 250 ml vessel are introduced 40.0 g technical grade tetraethylenepentamine (Aldrich) and 40.0 g methylated (transesterified) soybean oil (Dubois), to form a reaction mixture. The reaction mixture is heated at 200° C. for 4 hours. The methanol (7 g) generated during formation of the amide is extracted during the reaction using a Dean-Stark apparatus.

A colloidal composition of the invention is then prepared by a procedure similar to that of Example 4, except that 11.5 g pure glyphosate acid is neutralized with 11.1 g of the tetraethylenepentamine derivative synthesized as above, in 98 g deionized water. Processing time is 1 hour, at 25° C.

Example 66

A purified cocoamide derivative of triethylenetetramine, abbreviated in tables herein as "coco-CO-TETA", in which the acyl groups are derived from coconut oil, is synthesized by the following procedure. Into a 250 ml vessel are introduced 54.5 g technical grade triethylenetetramine, purity 60% (Aldrich) and 48.8 g coconut oil (Aldrich), to form a reaction mixture. The reaction mixture is heated at 200° C. for 4 hours. The reaction product is recovered in a toluene-water mixture, forming an emulsion to which ethanol is added until the emulsion is broken to form an aqueous phase and an organic phase. After separation of the aqueous phase, the organic phase is washed with water, followed by addition of sufficient ethanol to break the resulting emulsion as in the previous step. The aqueous phase is again separated and the organic phase once again washed with water followed by ethanol addition as before. Finally the organic phase is dried over magnesium sulfate and the solvent is evaporated. The product is then dried overnight under vacuum.

A colloidal composition of the invention is then prepared by a procedure similar to that of Example 4, except that 12.0 g pure glyphosate acid is neutralized with 17.1 g of the triethylenetetramine derivative synthesized as above, in 210.9 g deionized water. Processing time is 3 hours, at 25° C.

Example 67

N-palmityl triethylenetetramine, abbreviated in tables herein as "1C16-TETA", is synthesized by a procedure similar to that of Example 4. The reaction mixture consists of 80.0 g technical grade triethylenetetramine, purity 60% (Aldrich), 100.0 g 1-bromohexadecane, purity 97% (Aldrich), 36.0 g sodium bicarbonate and 400 ml ethanol.

A colloidal composition of the invention is then prepared by a procedure similar to that of Example 4, except that 12.0 g pure glyphosate acid is neutralized with 21.2 g N-palmityl triethylenetetramine synthesized as above, in 206.8 g deionized water. Processing time is 4 hours, at 70° C.

Example 68

A colloidal composition of the invention is prepared by a procedure similar to that of Example 4, except that 12.1 g pure glyphosate acid is neutralized with 20.0 g N-oleyl trimethylenediamine (Radiamine™ 6572 of Fina), abbreviated in tables herein as "1C18=TDA", in 88.2 g deionized water. Processing time is 1 hour at 80° C., followed by 8 hours at 20° C.

Example 69

A colloidal composition of the invention is prepared by a procedure similar to that of Example 4, except that 12.4 g pure glyphosate acid is neutralized with 17.6 g N-stearyl trimethylenediamine (Radiamine™ 6570 of CECA), abbreviated in tables herein as "1C18-TDA", in 92.1 g deionized water. Processing time is 1 hour at 80° C., followed by 8 hours at 20° C.

Example 70

A colloidal composition of the invention is prepared by a procedure similar to that of Example 4, except that 12.0 g pure glyphosate acid is neutralized with 14.9 g N-lauryl trimethylenediamine (Genamin™ LAP-100D of Clariant), abbreviated in tables herein as "1C12-TDA", in 93.6 g deionized water. Processing time is 1 hour at 80° C., followed by 8 hours at 20° C.

Example 71

The compositions of Examples 4–70 are subjected to the following observations and measurements.

Appearance of the concentrate composition is recorded on completion of the preparation process described in the Examples above.

The concentrate composition is diluted to a glyphosate a.e. concentration of 0.5% by weight for measurement of pH.

An estimate of the maximum glyphosate loading ($C_{max}$) as percent a.e. by weight attainable with the particular amphiphilic salt of each Example is made by testing the colloidal composition preparation procedure with progressively lower amounts of deionized water to determine if the resulting composition shows acceptable homogeneity indicative of at least short-term stability. In most cases testing is done at concentration increments of 5 percentage points by weight. Thus, for example, a $C_{max}$ estimate of 15% by weight means that a homogeneous colloidal formulation can be prepared at 15% but not at 20% by weight. In a few cases testing was done at smaller concentration increments; these cases will be apparent from the data presented below.

Table 2 shows the results of the above observations and measurements, together with calculated mole ratios (nA/X) where appropriate and actual glyphosate loading of the compositions whose preparation is described in Examples 4–70. Mole ratios shown assume 100% purity of the polyamine used to neutralize the glyphosate; however purity was generally not determined, thus the mole ratios shown are probably higher than the true values of nA/X in most cases.

TABLE 2

Results for Example 71

| Example | Polyamine[1] | Mole ratio[2] | Loading (wt %)[3] | Appearance | pH | $C_{max}$ (wt %) |
|---|---|---|---|---|---|---|
| 4 | 1C12-TETA | 3.41 | 5.0 | brown, opaque, nacreous | 5.4 | <5 |
| 5 | 1C18-TETA | 3.40 | 5.0 | milky | 4.8 | 5 |

TABLE 2-continued

Results for Example 71

| Example | Polyamine[1] | Mole ratio[2] | Loading (wt %)[3] | Appearance | pH | $C_{max}$ (wt %) |
|---|---|---|---|---|---|---|
| 6 | 2C18-TETA | 2.13 | 5.0 | flocculated | 4.7 | 10 |
| 7 | 1C8-TEPA | 1.97 | 5.0 | yellow, clear | 5.2 | 35 |
| 8a | 1C12-TEPA | 2.49 | 5.0 | turbid | 5.1 | 25 |
| 8b | | 2.49 | 5.0 | | 4.3 | |
| 9 | 1C18-TEPA | 3.26 | 5.0 | brown, opaque | 3.5 | 5 |
| 10a | 2C18-TEPA | 2.84 | 4.9 | brown, opaque | 4.2 | 5 |
| 10b | | 3.35 | 5.0 | | 4.2 | |
| 11a | coco-TDA | 0.95 | 5.0 | yellow, clear | 3.8 | 20 |
| 11b | | 1.02 | 5.0 | | 3.3 | |
| 12a | tallow-TDA | 0.93 | 5.0 | yellow, clear | 3.7 | 15 |
| 12b | | 0.93 | 5.0 | | 3.0 | |
| 13a | 1C18-TDA | 0.81 | 5.0 | yellow, clear | 3.4 | 15 |
| 13b | | 0.82 | 5.0 | | 2.7 | |
| 14a | tallow-DPTA | 1.06 | 5.0 | yellow, clear | 4.1 | 20 |
| 14b | | 1.06 | 4.9 | | 3.2 | |
| 15 | coco-DPTA | 1.02 | 5.0 | yellow, clear | 4.0 | 15 |
| 16 | 1C12-BDA | 1.41 | 5.0 | yellow, clear | 4.0 | 20 |
| 17 | 1C18-BDA | 2.21 | 5.0 | brown, opaque | 4.3 | 5 |
| 18a | 1C12-HDA | 1.46 | 4.9 | slightly flocculated | 5.1 | 20 |
| 18b | | 2.39 | 5.0 | | 5.1 | |
| 19 | 1C10-DHTA | 1.64 | 5.0 | yellow, clear | 5.3 | 25 |
| 20a | 1C12-DHTA | 1.22 | 5.0 | yellow, clear | 4.8 | 24 |
| 20b | | 1.22 | 5.0 | | 3.4 | |
| 21 | 2C12-TETA | 1.67 | 5.0 | yellow, clear | 4.5 | 20 |
| 22 | 1C14-HDA | 1.71 | 5.0 | opaque | 4.2 | 5 |
| 23 | 1C8=S-HDA | 2.97 | 5.0 | turbid | 4.5 | 5 |
| 24 | 1.5C11-CO-DETA | 1.55 | 5.0 | brown, turbid | 4.4 | 5 |
| 25 | 1.2C17=CO-DETA | 2.66 | 5.0 | brown, opaque | 4.6 | 5 |
| 26 | 1.2C9-CO-TETA | 1.31 | 5.0 | brown, turbid | 4.1 | 5 |
| 27 | 2C9-CO-TETA | 1.96 | 5.0 | opaque | 3.9 | 5 |
| 28 | 2C11-CO-TETA | 1.85 | 5.0 | opaque | 4.3 | 5 |
| 29 | 1.2C17-CO-TETA | 2.03 | 5.0 | brown, opaque | 3.8 | 5 |
| 30 | 1.5C17-CO-TETA | 2.03 | 5.0 | brown, opaque | 4.0 | 5 |
| 31a | 1.2C17=CO-TETA[4] | 3.51 | 5.0 | brown, opaque | 4.2 | 5 |
| 31b | | 3.45 | 5.1 | | 3.2 | |
| 32 | 1.2C9-CO-TEPA | 1.05 | 5.0 | slightly flocculated | 3.3 | 35 |
| 33 | 1C7-CO-TEPA | 1.46 | 5.0 | brown, clear | 4.6 | 5 |
| 34 | 1.5C9-CO-TEPA | 1.29 | 5.0 | brown, clear | 4.1 | 5 |
| 35 | 2C9-CO-TEPA | 1.21 | 5.0 | brown, clear | 4.1 | 5 |
| 36 | 1.2C11-CO-TEPA | 1.21 | 5.0 | yellow, clear | 4.1 | 30 |
| 37 | 2C11-CO-TEPA | 1.29 | 5.0 | brown, clear | 3.8 | 20 |
| 38 | 1.2C17=CO-TEPA | 2.44 | 5.0 | brown, turbid | 3.8 | 5 |
| 39 | 1.5C17=CO-TEPA | 2.77 | 5.0 | brown, turbid | 4.5 | 5 |
| 40 | 1.5C17-CO-TEPA | 1.98 | 5.0 | yellow, clear | 3.8 | 5 |
| 41 | 2C17=CO-TEPA | 2.08 | 5.0 | brown, opaque | 4.0 | 10 |
| 42 | 2C17-CO-TEPA | 2.69 | 3.0 | brown, opaque, tending to gel | 4.2 | 5 |
| 43 | 1.2C7-CO-DHTA | 2.72 | 5.0 | brown, opaque, tending to gel | 3.9 | 5 |
| 44 | 2C17-CO-TETA | 1.03 | 5.0 | brown, opaque | 5.0 | 5 |
| 45 | 2C17=CO-TETA | 1.55 | 5.0 | brown, opaque | 4.3 | 5 |
| 46 | 1.2C17=CO-TETA[5] | 2.66 | 5.0 | yellow, clear | 4.6 | n.d. |
| 47 | coco-CO-TETA | n.d. | 9.6 | yellow, clear | 4.6 | 40 |
| 48 | palm-CO-TETA | n.d. | 9.4 | yellow, turbid | 4.7 | 35 |
| 49 | castor-CO-TETA | n.d. | 9.4 | yellow, clear | 4.8 | 30 |
| 50 | olive-CO-TETA | n.d. | 9.4 | yellow, turbid | 4.7 | 30 |
| 51 | olive-CO-TEPA | n.d. | 9.4 | brown, clear | 4.6 | 30 |
| 52 | palm-CO-TEPA | n.d. | 9.4 | brown, turbid | 4.6 | 35 |
| 53 | castor-CO-TEPA | n.d. | 9.4 | yellow, clear | 4.6 | 30 |
| 54 | coco-CO-TEPA | n.d. | 9.6 | yellow, clear | 4.7 | 30 |
| 55 | coco-CO-TDA | n.d. | 9.6 | milky | 4.7 | 10 |
| 56 | coco-CO-DPTA | n.d. | 9.6 | yellow, clear | 4.7 | 10 |
| 57 | castor-CO-DPTA | n.d. | 9.6 | yellow, clear | 4.7 | 20 |
| 58 | coco-CO-BDA | n.d. | 9.7 | white, creamy | 4.6 | 10 |
| 59 | palm-CO-HDA | n.d. | 4.8 | milky, viscous | 4.8 | n.d. |
| 60 | coco-CO-HDA | n.d. | 9.6 | opaque, viscous | 4.4 | 15 |
| 61 | palm-CO-DHTA | n.d. | 5.0 | yellow, clear | 4.2 | 10 |
| 62 | castor-CO-DHTA | n.d. | 9.5 | brown, opaque | 4.9 | 18 |
| 63 | coco-CO-DHTA | n.d. | 9.6 | yellow, opaque | 4.9 | 14 |
| 64 | olive-CO-DHTA | n.d. | 5.0 | yellow, clear | 5.8 | <10 |
| 65 | soy-CO-TEPA | n.d. | 9.5 | yellow, clear | 4.7 | 35 |
| 66 | coco-CO-TETA | n.d. | 5.0 | yellow, clear | 4.7 | 17 |
| 67 | 1C16-TETA | 3.23 | 5.0 | yellow, clear | 4.6 | n.d. |
| 68 | 1C18=TDA | 1.72 | 10.0 | brown, viscous | 4.6 | n.d. |

TABLE 2-continued

Results for Example 71

| Example | Polyamine[1] | Mole ratio[2] | Loading (wt %)[3] | Appearance | pH | $C_{max}$ (wt %) |
|---|---|---|---|---|---|---|
| 69 | 1C18-TDA | 1.47 | 10.2 | yellow, clear | 4.0 | n.d. |
| 70 | 1C12-TDA | 1.73 | 10.0 | yellow, clear | 5.1 | 15 |

[1] abbreviations for polyamines can be understood by reference to the Examples.
[2] mole ratio of amino groups to glyphosate a.e. (nA/X); for molecular weight calculation, tallowamine considered as $C_{18}H_{35}$ (oleyl), cocoalkyl considered as $C_{12}H_{25}$ (lauryl).
[3] glyphosate a.e. loading of concentrate composition of the Example indicated.
[4] this sample is not washed to remove water-soluble components.
[5] this sample is washed to remove water-soluble components.
n.d. = not determined.

Example 72

The compositions of Examples 5 and 6 (comprising salts of glyphosate prepared with N-stearyl and N,N-distearyl triethylenetetramine respectively) are evaluated for herbicidal effectiveness in a greenhouse test by foliar application to a representative annual broadleaf species, velvetleaf (*Abutilon theophrasti*, ABUTH) and a representative annual narrowleaf species, Japanese millet, a form of barnyardgrass (*Echinochloa crus-galli*, ECHCF). For comparative purposes, the following commercial standard formulations are included in the test:

MON 0139, an aqueous solution of the mono (isopropylammonium) salt of glyphosate, containing 62% by weight of said salt and no other formulation ingredients except water, available from Monsanto Company; and Roundup® Ultra herbicide, an aqueous solution concentrate formulation of the mono(isopropylammonium) salt of glyphosate, containing 41% by weight of said salt together with a surfactant, this product being sold as an agricultural herbicide by Monsanto Company in the U.S.A. MON 0139 contains glyphosate at a concentration of about 680 grams of acid equivalent per liter (g a.e./l) and Roundup® Ultra herbicide contains 356 g a.e./l.

The following procedure is used for the greenhouse test.

Seeds of the plant species indicated are planted in 85 mm square pots in a soil mix which has previously been steam sterilized and prefertilized with a 14-14-14 NPK slow release fertilizer at a rate of 3.6 kg/m³. The pots are placed in a greenhouse with sub-irrigation. About one week after emergence, seedlings are thinned as needed, including removal of any unhealthy or abnormal plants, to create a uniform series of test pots.

The plants are maintained for the duration of the test in the greenhouse where they receive a minimum of 14 hours of light per day. If natural light is insufficient to achieve the daily requirement, artificial light with an intensity of approximately 475 microeinsteins is used to make up the difference. Exposure temperatures are not precisely controlled but average about 27° C. during the day and about 18° C. during the night. Plants are sub-irrigated throughout the test to ensure adequate soil moisture levels. Relative humidity is maintained at about 50% for the duration of the test.

Pots are assigned to different treatments in a fully randomized experimental design with 3 replications. A set of pots is left untreated as a reference against which effects of the treatments can later be evaluated. Two sets of 3 replications are provided for treatments with Roundup® Ultra, to ensure a sound basis is available for comparison of herbicidal effectiveness of compositions of the invention.

Application of glyphosate compositions to foliage is made by spraying with a track sprayer fitted with a TeeJet™ 9501E nozzle calibrated to deliver a spray volume of 93 liters per hectare (l/ha) at a pressure of 166 kilopascals (kPa). Application is made when the plants are 2–3 weeks old. After treatment, pots are returned to the greenhouse until ready for evaluation, in this Example 15 days after treatment (DAT).

Treatments are made using dilute aqueous compositions, prepared by dilution with water of preformulated concentrate compositions. All comparisons are made at equal glyphosate acid equivalent rates. The required degree of dilution for a glyphosate concentrate composition to make a plant treatment composition is calculated from the equation $$A = RS/VC$$

where A is the volume in milliliters (ml) of the glyphosate composition to be added to the plant treatment composition being prepared, R is the desired glyphosate rate in grams of acid equivalent per hectare (g a.e./ha), S is the total volume in milliliters (ml) of plant treatment composition being prepared, V is the application rate in liters per hectare (l/ha) of plant treatment composition, conventionally referred to as "spray volume", and C is the concentration of glyphosate in grams of acid equivalent per liter (g a.e./l) in the glyphosate composition.

For evaluation of herbicidal effectiveness, all plants in the test are examined by a single practiced technician, who records percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as the one described in this Example it is normal to apply compositions at rates which are expected to give less than 85% inhibition, as this makes it easier to discriminate among compositions having different levels of effectiveness.

Results of the test of Example 72 are given in Table 3 below.

TABLE 3

Herbicidal effectiveness data for Example 72

| Glyphosate composition | Glyphosate rate g a.e./ha | % Inhibition ABUTH | % Inhibition ECHCF |
|---|---|---|---|
| MON 0139 | 200 | 0 | 50 |
| | 400 | 2 | 62 |
| | 600 | 43 | 75 |
| | 800 | 72 | 77 |
| | 1000 | 83 | 85 |
| Roundup ® Ultra (first set) | 200 | 20 | 50 |
| | 400 | 57 | 60 |
| | 600 | 75 | 82 |
| | 800 | 88 | 93 |
| | 1000 | 95 | 94 |
| Roundup ® Ultra (second set) | 200 | 5 | 67 |
| | 400 | 33 | 73 |
| | 600 | 72 | 83 |
| | 800 | 87 | 85 |
| | 1000 | 90 | 96 |
| Example 5: 1C18-TETA | 200 | 0 | 30 |
| | 400 | 27 | 33 |
| | 600 | 68 | 33 |
| | 800 | 82 | 40 |
| | 1000 | 80 | 45 |
| Example 6: 2C18-TETA | 200 | 0 | 5 |
| | 400 | 47 | 15 |
| | 600 | 70 | 10 |
| | 800 | 80 | 33 |
| | 1000 | 90 | 42 |

In this test the colloidal dispersions of Examples 5 and 6 provided herbicidal effectiveness on ABUTH superior to that provided by isopropylammonium glyphosate (MON 0139) at equal glyphosate a.e. rates. However, herbicidal effectiveness of these colloidal dispersions was very weak on ECHCF, and even on ABUTH was not as great as that provided by the commercial standard Roundup® Ultra in this test.

Example 73

Substantially the same procedure as used in Example 72 is followed in a greenhouse test by foliar application to ABUTH and ECHCF. Evaluation of herbicidal effectiveness is conducted 15 DAT. The compositions included in this test are those of Examples 7 and 8a (comprising salts of glyphosate prepared with N-(n-octyl) and N-lauryl tetraethylenepentamine respectively), 11a–13a (comprising salts of glyphosate prepared with N-cocoalkyl, N-tallowalkyl and N-stearyl trimethylenediamine respectively), 14a and 15 (comprising salts of glyphosate prepared with N-tallowalkyl and N-cocoalkyl dipropylenetriamine respectively), and 19 and 20a (comprising salts of glyphosate prepared with N-(n-decyl) and N-lauryl bis(hexamethylene)triamine respectively). Results of the test of Example 73 are given in Table 4 below.

TABLE 4

Herbicidal effectiveness data for Example 73

| Glyphosate composition | Glyphosate rate g a.e./ha | % Inhibition ABUTH | % Inhibition ECHCF |
|---|---|---|---|
| MON 0139 | 200 | 3 | 48 |
| | 400 | 17 | 55 |
| | 600 | 33 | 82 |
| | 800 | 70 | 87 |

TABLE 4-continued

Herbicidal effectiveness data for Example 73

| Glyphosate composition | Glyphosate rate g a.e./ha | % Inhibition ABUTH | % Inhibition ECHCF |
|---|---|---|---|
| | 1000 | 95 | 95 |
| Roundup ® Ultra (first set) | 200 | 3 | 62 |
| | 400 | 20 | 89 |
| | 600 | 73 | 96 |
| | 800 | 90 | 96 |
| | 1000 | 92 | 97 |
| Roundup ® Ultra (second set) | 200 | 0 | 70 |
| | 400 | 30 | 90 |
| | 600 | 75 | 93 |
| | 800 | 82 | 97 |
| | 1000 | 90 | 98 |
| Example 7: 1C8-TEPA | 200 | 0 | 33 |
| | 400 | 32 | 62 |
| | 600 | 78 | 82 |
| | 800 | 83 | 87 |
| | 1000 | 87 | 90 |
| Example 8a: 1C12-TEPA | 200 | 2 | 40 |
| | 400 | 47 | 55 |
| | 600 | 87 | 60 |
| | 800 | 88 | 85 |
| | 1000 | 90 | 93 |
| Example 11a: coco-TDA | 200 | 0 | 45 |
| | 400 | 67 | 62 |
| | 600 | 83 | 75 |
| | 800 | 93 | 93 |
| | 1000 | 93 | 99 |
| Example 12a: tallow-TDA | 200 | 17 | 52 |
| | 400 | 75 | 68 |
| | 600 | 88 | 82 |
| | 800 | 88 | 97 |
| | 1000 | 97 | 99 |
| Example 13a: 1C18-TDA | 200 | 20 | 57 |
| | 400 | 78 | 80 |
| | 600 | 77 | 94 |
| | 800 | 89 | 94 |
| | 1000 | 97 | 100 |
| Example 14a: tallow-DPTA | 200 | 3 | 45 |
| | 400 | 37 | 57 |
| | 600 | 78 | 68 |
| | 800 | 80 | 87 |
| | 1000 | 88 | 97 |
| Example 15: coco-DPTA | 200 | 0 | 53 |
| | 400 | 25 | 63 |
| | 600 | 70 | 88 |
| | 800 | 78 | 96 |
| | 1000 | 80 | 99 |
| Example 19: 1C10-DHTA | 200 | 0 | 27 |
| | 400 | 30 | 55 |
| | 600 | 50 | 80 |
| | 800 | 88 | 82 |
| | 1000 | 87 | 93 |
| Example 20a: 1C12-DHTA | 200 | 0 | 60 |
| | 400 | 33 | 72 |
| | 600 | 60 | 88 |
| | 800 | 83 | 98 |
| | 1000 | 83 | 99 |

In this test the colloidal dispersions of Examples 11a–13a, comprising salts of glyphosate with N-alkyl and N-alkenyl trimethylenediamines, gave particularly strong herbicidal performance, especially on ABUTH.

Example 74

Substantially the same procedure as used in Example 72 is followed in a greenhouse test by foliar application to ABUTH and ECHCF. Evaluation of herbicidal effectiveness is conducted 17 DAT. The compositions included in this test are those of Examples 4 (comprising a salt of glyphosate prepared with N-lauryl triethylenetetramine), 9 (comprising a salt of glyphosate prepared with N-stearyl tetraethylenepentamine), 16 (comprising a salt of glyphosate prepared with N-lauryl butylenediamine), 24 (comprising a salt of glyphosate prepared with n-lauramide derivatives of diethylenetriamine), 32 and 33 (comprising salts of glyphosate prepared with n-decanamide and n-octanamide derivatives of tetraethylenepentamine respectively), and 43 (comprising a salt of glyphosate prepared with n-octanamide derivatives of bis(hexamethylene)triamine). Results of the test of Example 74 are given in Table 5 below.

TABLE 5

Herbicidal effectiveness data for Example 74

| Glyphosate composition | Glyphosate rate g a.e./ha | % Inhibition ABUTH | % Inhibition ECHCF |
|---|---|---|---|
| MON 0139 | 200 | 8 | 70 |
|  | 400 | 50 | 75 |
|  | 600 | 78 | 85 |
|  | 800 | 83 | 90 |
|  | 1000 | 95 | 96 |
| Roundup ® Ultra (first set) | 200 | 65 | 83 |
|  | 400 | 78 | 99 |
|  | 600 | 91 | 99 |
|  | 800 | 99 | 100 |
|  | 1000 | 99 | 100 |
| Roundup ® Ultra (second set) | 200 | 60 | 83 |
|  | 400 | 75 | 98 |
|  | 600 | 88 | 100 |
|  | 800 | 99 | 99 |
|  | 1000 | 98 | 100 |
| Example 4: 1C12-TETA | 200 | 50 | 47 |
|  | 400 | 68 | 77 |
|  | 600 | 78 | 97 |
|  | 800 | 67 | 100 |
|  | 1000 | 96 | 98 |
| Example 9: 1C18-TEPA | 200 | 27 | 47 |
|  | 400 | 53 | 77 |
|  | 600 | 75 | 85 |
|  | 800 | 82 | 90 |
|  | 1000 | 83 | 83 |
| Example 16: 1C12-BDA | 200 | 48 | 85 |
|  | 400 | 67 | 97 |
|  | 600 | 92 | 98 |
|  | 800 | 98 | 100 |
|  | 1000 | 98 | 99 |
| Example 24: 1.5C11-CO-DETA | 200 | 52 | 77 |
|  | 400 | 82 | 83 |
|  | 600 | 93 | 93 |
|  | 800 | 98 | 99 |
|  | 1000 | 98 | 99 |
| Example 32: 1.2C9-CO-TEPA | 200 | 43 | 80 |
|  | 400 | 60 | 88 |
|  | 600 | 85 | 98 |
|  | 800 | 80 | 100 |
|  | 1000 | 92 | 100 |
| Example 33: 1C7-CO-TEPA | 200 | 33 | 73 |
|  | 400 | 68 | 83 |
|  | 600 | 72 | 100 |
|  | 800 | 87 | 96 |
|  | 1000 | 88 | 100 |
| Example 43: 1.2C7-CO-DHTA | 200 | 38 | 75 |
|  | 400 | 77 | 98 |
|  | 600 | 78 | 99 |
|  | 800 | 88 | 100 |
|  | 1000 | 98 | 99 |

In this test none of the colloidal dispersions of the Examples outperformed the commercial standard Roundup® Ultra on ABUTH or ECHCF.

Example 75

Substantially the same procedure as used in Example 72 is followed in a greenhouse test by foliar application to ABUTH and ECHCF. Evaluation of herbicidal effectiveness is conducted 16 DAT. The compositions included in this test are those of Examples 10a (comprising a salt of glyphosate prepared with a distearamide derivative of tetraethylenepentamine), 18a (comprising a salt of glyphosate prepared with a lauramide derivative of hexamethylenediamine), 25 (comprising a salt of glyphosate prepared with oleamide derivatives of diethylenetriamine), and 26 and 28–31a (comprising salts of glyphosate prepared with n-decanamide, dilauramide, stearamide (1.2 moles), stearamide (1.5 moles) and oleamide derivatives of triethylenetetramine respectively). Results of the test of Example 75 are given in Table 6 below.

TABLE 6

Herbicidal effectiveness data for Example 75

| Glyphosate composition | Glyphosate rate g a.e./ha | % Inhibition ABUTH | % Inhibition ECHCF |
|---|---|---|---|
| MON 0139 | 200 | 5 | 27 |
|  | 400 | 53 | 52 |
|  | 600 | 70 | 67 |
|  | 800 | 78 | 78 |
|  | 1000 | 95 | 78 |
| Roundup ® Ultra (first set) | 200 | 33 | 57 |
|  | 400 | 67 | 67 |
|  | 600 | 83 | 83 |
|  | 800 | 93 | 97 |
|  | 1000 | 98 | 97 |
| Roundup ® Ultra (second set) | 200 | 30 | 62 |
|  | 400 | 60 | 73 |
|  | 600 | 83 | 77 |
|  | 800 | 87 | 85 |
|  | 1000 | 95 | 92 |
| Example 10a: 2C18-TEPA | 200 | 3 | 25 |
|  | 400 | 47 | 30 |
|  | 600 | 53 | 40 |
|  | 800 | 70 | 47 |
|  | 1000 | 83 | 60 |
| Example 18a: 1C12-HDA | 200 | 3 | 15 |
|  | 400 | 5 | 33 |
|  | 600 | 48 | 72 |
|  | 800 | 68 | 83 |
|  | 1000 | 78 | 92 |
| Example 25: 1.2C17 = CO-DETA | 200 | 2 | 33 |
|  | 400 | 35 | 60 |
|  | 600 | 75 | 73 |
|  | 800 | 88 | 88 |
|  | 1000 | 92 | 87 |
| Example 26: 1.2C9-CO-TETA | 200 | 8 | 20 |
|  | 400 | 40 | 50 |
|  | 600 | 62 | 73 |
|  | 800 | 75 | 73 |
|  | 1000 | 80 | 77 |
| Example 28: 2C11-CO-TETA | 200 | 5 | 8 |
|  | 400 | 27 | 40 |
|  | 600 | 58 | 53 |
|  | 800 | 70 | 60 |
|  | 1000 | 87 | 65 |
| Example 29: 1.2C17-CO-TETA | 200 | 3 | 20 |
|  | 400 | 55 | 28 |
|  | 600 | 63 | 43 |
|  | 800 | 77 | 57 |
|  | 1000 | 91 | 60 |
| Example 30: 1.5C17-CO-TETA | 200 | 20 | 0 |
|  | 400 | 27 | 30 |
|  | 600 | 50 | 30 |
|  | 800 | 75 | 40 |
|  | 1000 | 92 | 50 |
| Example 31a: 1.2C17 = CO-TETA | 200 | 55 | 43 |
|  | 400 | 77 | 53 |
|  | 600 | 90 | 63 |
|  | 800 | 96 | 63 |
|  | 1000 | 98 | 67 |

In this test the highest level of herbicidal activity on ABUTH was seen with the colloidal dispersion of Example 31a.

Example 76

Substantially the same procedure as used in Example 76 is followed in a greenhouse test by foliar application to ABUTH and ECHCF. Evaluation of herbicidal effectiveness is conducted 16 DAT. The compositions included in this test are those of Examples 27 (comprising a salt of glyphosate prepared with a di(n-octanamide) derivative of triethylenetetramine), and 34–39 and 41 (comprising salts of glyphosate prepared with n-decanamide (1.5 moles), n-decanamide (2 moles), lauramide (1.2 moles), lauramide (2 moles), oleamide (1.2 moles), oleamide (1.5 moles) and oleamide (2 moles) derivatives of tetraethylenepentamine respectively). Results of the test of Example 76 are given in Table 7 below.

TABLE 7

Herbicidal effectiveness data for Example 76

| Glyphosate composition | Glyphosate rate g a.e./ha | % Inhibition ABUTH | % Inhibition ECHCF |
|---|---|---|---|
| MON 0139 | 200 | 8 | 33 |
|  | 400 | 47 | 53 |
|  | 600 | 68 | 68 |
|  | 800 | 77 | 78 |
|  | 1000 | 88 | 94 |
| Roundup ® Ultra (first set) | 200 | 30 | 60 |
|  | 400 | 55 | 80 |
|  | 600 | 78 | 99 |
|  | 800 | 92 | 99 |
|  | 1000 | 95 | 100 |
| Roundup ® Ultra (second set) | 200 | 37 | 55 |
|  | 400 | 68 | 77 |
|  | 600 | 87 | 93 |
|  | 800 | 88 | 92 |
|  | 1000 | 93 | 96 |
| Example 27: 2C9-CO-TETA | 200 | 37 | 63 |
|  | 400 | 72 | 77 |
|  | 600 | 78 | 83 |
|  | 800 | 93 | 80 |
|  | 1000 | 93 | 90 |
| Example 34: 1.5C9-CO-TEPA | 200 | 37 | 43 |
|  | 400 | 63 | 77 |
|  | 600 | 87 | 82 |
|  | 800 | 93 | 90 |
|  | 1000 | 88 | 83 |
| Example 35: 2C9-CO-TEPA | 200 | 5 | 30 |
|  | 400 | 53 | 72 |
|  | 600 | 77 | 91 |
|  | 800 | 80 | 83 |
|  | 1000 | 83 | 93 |
| Example 36: 1.2C11-CO-TEPA | 200 | 13 | 60 |
|  | 400 | 67 | 87 |
|  | 600 | 83 | 85 |
|  | 800 | 95 | 95 |
|  | 1000 | 96 | 97 |
| Example 37: 2C11-CO-TEPA | 200 | 57 | 57 |
|  | 400 | 75 | 60 |
|  | 600 | 83 | 83 |
|  | 800 | 94 | 93 |
|  | 1000 | 94 | 97 |
| Example 38: 1.2C17 = CO-TEPA | 200 | 45 | 53 |
|  | 400 | 65 | 80 |
|  | 600 | 87 | 77 |
|  | 800 | 87 | 99 |
|  | 1000 | 90 | 98 |
| Example 39: 1.5C17 = CO-TEPA | 200 | 50 | 62 |
|  | 400 | 67 | 73 |
|  | 600 | 75 | 87 |
|  | 800 | 88 | 98 |
|  | 1000 | 88 | 97 |
| Example 41: 2C17 = CO-TEPA | 200 | 43 | 40 |
|  | 400 | 60 | 63 |
|  | 600 | 75 | 78 |
|  | 800 | 80 | 85 |
|  | 1000 | 83 | 73 |

In this test many colloidal dispersions of the Examples performed at least comparably to the commercial standard Roundup® Ultra on ABUTH.

Example 77

Substantially the same procedure as used in Example 72 is followed in a greenhouse test by foliar application to ABUTH and ECHCF. Evaluation of herbicidal effectiveness is conducted 21 DAT. The compositions included in this test are those of Examples 17 (comprising a salt of glyphosate prepared with N-stearyl butylenediamine), 23 (comprising a salt of glyphosate prepared with an N-(n-octenyl) succinimide derivative of hexamethylenediamine), and 40 and 42 (comprising salts of glyphosate prepared with stearamide derivatives of tetraethylenepentamine). Results of the test of Example 77 are given in Table 8 below.

TABLE 8

Herbicidal effectiveness data for Example 77

| Glyphosate composition | Glyphosate rate g a.e./ha | % Inhibition ABUTH | % Inhibition ECHCF |
|---|---|---|---|
| MON 0139 | 200 | 0 | 50 |
|  | 400 | 20 | 77 |
|  | 600 | 45 | 87 |
|  | 800 | 47 | 88 |
|  | 1000 | 73 | 95 |
| Roundup ® Ultra (first set) | 200 | 25 | 77 |
|  | 400 | 50 | 95 |
|  | 600 | 63 | 98 |
|  | 800 | 92 | 100 |
|  | 1000 | 100 | 100 |
| Roundup ® Ultra (second set) | 200 | 10 | 80 |
|  | 400 | 40 | 97 |
|  | 600 | 60 | 99 |
|  | 800 | 90 | 100 |
|  | 1000 | 98 | 100 |
| Example 17: 1C18-BDA | 200 | 27 | 20 |
|  | 400 | 43 | 33 |
|  | 600 | 53 | 63 |
|  | 800 | 63 | 70 |
|  | 1000 | 70 | 77 |
| Example 23: 1C8 = S-HDA | 200 | 18 | 75 |
|  | 400 | 40 | 92 |
|  | 600 | 53 | 95 |
|  | 800 | 67 | 99 |
|  | 1000 | 91 | 100 |
| Example 40: 1.5C17-CO-TEPA | 200 | 27 | 20 |
|  | 400 | 43 | 50 |
|  | 600 | 50 | 65 |
|  | 800 | 67 | 82 |
|  | 1000 | 77 | 83 |
| Example 42: 2C17-CO-TEPA | 200 | 17 | 5 |
|  | 400 | 33 | 7 |
|  | 600 | 43 | 30 |
|  | 800 | 53 | 30 |
|  | 1000 | 75 | 45 |

In this test none of the colloidal dispersions of the Examples matched the herbicidal performance of the commercial standard Roundup® Ultra on ABUTH or ECHCF.

Example 78

Substantially the same procedure as used in Example 72 is followed in a greenhouse test by foliar application to ABUTH and ECHCF. Evaluation of herbicidal effectiveness is conducted 16 DAT. The compositions included in this test are those of Examples 12a and 13a (comprising salts of glyphosate prepared with N-tallowalkyl and N-stearyl trimethylenediamines respectively), 21 (comprising a salt of glyphosate prepared with N,N-dilauryl triethylenetetramine), 22 (comprising a salt of glyphosate prepared with N-myristyl hexamethylenediamine), and 44 and 45 (comprising salts of glyphosate prepared with distearamide and dioleamide derivatives of triethylenetetramine respectively). Results of the test of Example 78 are given in Table 9 below.

TABLE 9

Herbicidal effectiveness data for Example 78

| Glyphosate composition | Glyphosate rate g a.e./ha | % Inhibition ABUTH | ECHCF |
|---|---|---|---|
| MON 0139 | 200 | 0 | 40 |
|  | 400 | 33 | 52 |
|  | 600 | 72 | 55 |
|  | 800 | 72 | 67 |
|  | 1000 | 87 | 68 |
| Roundup ® Ultra (first set) | 200 | 45 | 73 |
|  | 400 | 60 | 87 |
|  | 600 | 83 | 95 |
|  | 800 | 90 | 98 |
|  | 1000 | 92 | 98 |
| Roundup ® Ultra (second set) | 200 | 55 | 63 |
|  | 400 | 78 | 75 |
|  | 600 | 83 | 97 |
|  | 800 | 93 | 92 |
|  | 1000 | 93 | 98 |
| Example 12a: tallow-TDA | 200 | 23 | 47 |
|  | 400 | 70 | 72 |
|  | 600 | 78 | 75 |
|  | 800 | 92 | 82 |
|  | 1000 | 97 | 82 |
| Example 13a: 1C18-TDA | 200 | 43 | 53 |
|  | 400 | 75 | 57 |
|  | 600 | 88 | 75 |
|  | 800 | 93 | 83 |
|  | 1000 | 97 | 85 |
| Example 21: 2C12-TETA | 200 | 48 | 50 |
|  | 400 | 62 | 60 |
|  | 600 | 80 | 72 |
|  | 800 | 97 | 73 |
|  | 1000 | 98 | 78 |
| Example 22: 1C14-HDA | 200 | 50 | 53 |
|  | 400 | 65 | 70 |
|  | 600 | 83 | 80 |
|  | 800 | 88 | 93 |
|  | 1000 | 97 | 87 |
| Example 44: 2C17-CO-TETA | 200 | 65 | 53 |
|  | 400 | 75 | 57 |
|  | 600 | 82 | 63 |
|  | 800 | 90 | 67 |
|  | 1000 | 96 | 78 |
| Example 45: 2C17 = CO-TETA | 200 | 57 | 53 |
|  | 400 | 78 | 57 |
|  | 600 | 83 | 70 |
|  | 800 | 88 | 83 |
|  | 1000 | 94 | 86 |

In this test all of the colloidal dispersions of the Examples substantially matched the herbicidal performance of the commercial standard Roundup® Ultra on ABUTH.

Example 79

Substantially the same procedure as used in Example 72 is followed in a greenhouse test by foliar application to ABUTH and ECHCF. Evaluation of herbicidal effectiveness is conducted 17 DAT. The compositions included in this test are those of Examples 47–50 (comprising salts of glyphosate prepared with cocoamide, palmamide, castoramide and oliveamide derivatives of triethylenetetramine respectively), and 51–53 (comprising salts of glyphosate prepared with oliveamide, palmamide and castoramide derivatives of tetraethylenepentamine respective). Results of the test of Example 79 are given in Table 10 below.

TABLE 10

Herbicidal effectiveness data for Example 79

| Glyphosate composition | Glyphosate rate g a.e./ha | % Inhibition ABUTH | ECHCF |
|---|---|---|---|
| MON 0139 | 100 | 2 | 20 |
|  | 200 | 40 | 30 |
|  | 400 | 72 | 50 |
|  | 600 | 77 | 67 |
|  | 800 | 98 | 72 |
| Roundup ® Ultra (first set) | 100 | 67 | 65 |
|  | 200 | 88 | 73 |
|  | 400 | 98 | 98 |
|  | 600 | 100 | 100 |
|  | 800 | 100 | 100 |
| Roundup ® Ultra (second set) | 100 | 57 | 72 |
|  | 200 | 87 | 83 |
|  | 400 | 96 | 97 |
|  | 600 | 100 | 100 |
|  | 800 | 100 | 99 |
| Example 47: coco-CO-TETA | 100 | 2 | 67 |
|  | 200 | 28 | 73 |
|  | 400 | 80 | 92 |
|  | 600 | 93 | 99 |
|  | 800 | 99 | 100 |
| Example 48: palm-CO-TETA | 100 | 13 | 65 |
|  | 200 | 25 | 70 |
|  | 400 | 85 | 73 |
|  | 600 | 92 | 90 |
|  | 800 | 99 | 98 |
| Example 49: castor-CO-TETA | 100 | 20 | 65 |
|  | 200 | 60 | 83 |
|  | 400 | 97 | 99 |
|  | 600 | 99 | 100 |
|  | 800 | 100 | 100 |
| Example 50: olive-CO-TETA | 100 | 55 | 70 |
|  | 200 | 73 | 72 |
|  | 400 | 91 | 90 |
|  | 600 | 99 | 98 |
|  | 800 | 99 | 99 |
| Example 51: olive-CO-TEPA | 100 | 7 | 62 |
|  | 200 | 20 | 67 |
|  | 400 | 68 | 82 |
|  | 600 | 94 | 82 |
|  | 800 | 98 | 97 |
| Example 52: palm-CO-TEPA | 100 | 10 | 53 |
|  | 200 | 20 | 67 |
|  | 400 | 63 | 72 |
|  | 600 | 98 | 90 |
|  | 800 | 99 | 96 |
| Example 53: castor-CO-TEPA | 100 | 5 | 65 |
|  | 200 | 30 | 73 |
|  | 400 | 87 | 97 |
|  | 600 | 98 | 100 |
|  | 800 | 99 | 100 |

In this test none of the colloidal dispersions of the Examples, with the exception of Example 50, substantially matched the herbicidal performance of the commercial standard Roundup® Ultra on ABUTH; of the others, Example 49 came closest.

Example 80

Substantially the same procedure as used in Example 72 is followed in a greenhouse test by foliar application to ABUTH and ECHCF. Evaluation of herbicidal effectiveness is conducted 16 DAT. The compositions included in this test are those of Examples 10b (comprising a salt of glyphosate prepared with N,N-distearyl tetraethylenepentamine), 18b (comprising a salt of glyphosate prepared with N-lauryl hexamethylenediamine), and 20b (comprising a salt of glyphosate prepared with N-lauryl bis(hexamethylene) triamine). Results of the test of Example 80 are given in Table 11 below.

TABLE 11

Herbicidal effectiveness data for Example 80

| Glyphosate composition | Glyphosate rate g a.e./ha | % Inhibition ABUTH | % Inhibition ECHCF |
|---|---|---|---|
| MON 0139 | 100 | 27 | 38 |
| | 200 | 60 | 47 |
| | 400 | 85 | 53 |
| | 600 | 94 | 63 |
| | 800 | 98 | 70 |
| Roundup ® Ultra (first set) | 100 | 55 | 62 |
| | 200 | 83 | 82 |
| | 400 | 95 | 100 |
| | 600 | 100 | 98 |
| | 800 | 100 | 100 |
| Roundup ® Ultra (second set) | 100 | 50 | 55 |
| | 200 | 75 | 72 |
| | 400 | 96 | 97 |
| | 600 | 97 | 100 |
| | 800 | 98 | 100 |
| Example 10b: 2C18-TEPA | 100 | 55 | 20 |
| | 200 | 65 | 10 |
| | 400 | 78 | 17 |
| | 600 | 85 | 33 |
| | 800 | 93 | 45 |
| Example 18b: 1C12-HDA | 100 | 65 | 53 |
| | 200 | 87 | 70 |
| | 400 | 99 | 85 |
| | 600 | 100 | 93 |
| | 800 | 100 | 100 |
| Example 20b: 1C12-DHTA | 100 | 55 | 67 |
| | 200 | 80 | 70 |
| | 400 | 98 | 79 |
| | 600 | 99 | 98 |
| | 800 | 100 | 100 |

In this test all three of the colloidal dispersions of the Examples substantially matched the herbicidal performance of the commercial standard Roundup® Ultra on ABUTH. The composition of Example 10b exhibited notably weak herbicidal effectiveness on ECHCF in this test.

Example 81

Substantially the same procedure as used in Example 72 is followed in a greenhouse test by foliar application to ABUTH and ECHCF. Evaluation of herbicidal effectiveness is conducted 18 DAT. The compositions included in this test are those of Examples 18b (comprising a salt of glyphosate prepared with N-lauryl hexamethylenediamine), 20b (comprising a salt of glyphosate prepared with N-lauryl bis(hexamethylene)triamine), 59 and 60 (comprising salts of glyphosate prepared with palmamide and cocoamide derivatives of hexamethylenediamine respectively), and 62, 63 and 65 (comprising salts of glyphosate prepared with castoramide, cocoamide and soyamide derivatives of bis(hexamethylene)triamine respectively). Results of the test of Example 81 are given in Table 12 below.

TABLE 12

Herbicidal effectiveness data for Example 81

| Glyphosate composition | Glyphosate rate g a.e./ha | % Inhibition ABUTH | % Inhibition ECHCF |
|---|---|---|---|
| MON 0139 | 100 | 23 | 27 |
| | 200 | 60 | 55 |
| | 400 | 82 | 68 |
| | 600 | 98 | 87 |
| | 800 | 100 | 87 |
| Roundup ® Ultra (first set) | 100 | 65 | 83 |
| | 200 | 95 | 94 |
| | 400 | 100 | 100 |
| | 600 | 100 | 100 |
| | 800 | 100 | 100 |
| Roundup ® Ultra (second set) | 100 | 60 | 77 |
| | 200 | 97 | 98 |
| | 400 | 100 | 100 |
| | 600 | 100 | 100 |
| | 800 | 100 | 100 |
| Example 18b: 1C12-HDA | 100 | 53 | 72 |
| | 200 | 94 | 83 |
| | 400 | 99 | 96 |
| | 600 | 100 | 100 |
| | 800 | 100 | 100 |
| Example 20b: 1C12-DHTA | 100 | 33 | 73 |
| | 200 | 83 | 82 |
| | 400 | 98 | 90 |
| | 600 | 100 | 99 |
| | 800 | 100 | 100 |
| Example 59: palm-CO-HDA | 100 | 82 | 73 |
| | 200 | 96 | 88 |
| | 400 | 99 | 96 |
| | 600 | 100 | 100 |
| | 800 | 100 | 97 |
| Example 60: coco-CO-HDA | 100 | 70 | 82 |
| | 200 | 96 | 92 |
| | 400 | 99 | 99 |
| | 600 | 100 | 100 |
| | 800 | 100 | 100 |
| Example 62: castor-CO-DHTA | 100 | 8 | 75 |
| | 200 | 75 | 88 |
| | 400 | 98 | 96 |
| | 600 | 100 | 100 |
| | 800 | 100 | 100 |
| Example 63: coco-CO-DHTA | 100 | 77 | 68 |
| | 200 | 96 | 75 |
| | 400 | 100 | 97 |
| | 600 | 100 | 99 |
| | 800 | 100 | 100 |
| Example 65: soy-CO-TEPA | 100 | 2 | 67 |
| | 200 | 43 | 68 |
| | 400 | 88 | 80 |
| | 600 | 99 | 83 |
| | 800 | 100 | 91 |

In this test the colloidal dispersions of Examples 59, 60 and 63 exhibited the greatest herbicidal effectiveness.

Example 82

Substantially the same procedure as used in Example 72 is followed in a greenhouse test by foliar application to ABUTH and ECHCF, except that only one set of 3 replicates is treated with Roundup® Ultra in this test. Evaluation of herbicidal effectiveness is conducted 17 DAT. The compositions included in this test are those of Examples 10b (comprising a salt of glyphosate prepared with distearyl tetraethylenepentamine), 11b and 13b (comprising salts of glyphosate prepared with N-cocoalkyl and N-stearyl trimethylenediamine respectively), 18b (comprising a salt of glyphosate prepared with N-lauryl hexamethylenediamine), and 20b (comprising a salt of glyphosate prepared with N-lauryl bis(hexamethylene)triamine). Results of the test of Example 82 are given in Table 13 below.

TABLE 13

Herbicidal effectiveness data for Example 82

| Glyphosate composition | Glyphosate rate g a.e./ha | % Inhibition ABUTH | ECHCF |
|---|---|---|---|
| MON 0139 | 50 | 0 | 0 |
|  | 100 | 0 | 33 |
|  | 200 | 50 | 35 |
|  | 400 | 82 | 65 |
|  | 600 | 83 | 75 |
| Roundup ® Ultra | 50 | 10 | 50 |
|  | 100 | 53 | 75 |
|  | 200 | 85 | 91 |
|  | 400 | 98 | 100 |
|  | 600 | 99 | 100 |
| Example 10b: 2C18-TEPA | 50 | 0 | 30 |
|  | 100 | 0 | 17 |
|  | 200 | 55 | 38 |
|  | 400 | 77 | 52 |
|  | 600 | 87 | 62 |
| Example 11b: coco-TDA | 50 | 0 | 35 |
|  | 100 | 0 | 50 |
|  | 200 | 72 | 75 |
|  | 400 | 97 | 98 |
|  | 600 | 100 | 100 |
| Example 13b: 1C18-TDA | 50 | 3 | 38 |
|  | 100 | 50 | 53 |
|  | 200 | 77 | 84 |
|  | 400 | 90 | 99 |
|  | 600 | 99 | 100 |
| Example 18b: 1C12-HDA | 50 | 0 | 55 |
|  | 100 | 12 | 60 |
|  | 200 | 78 | 98 |
|  | 400 | 97 | 100 |
|  | 600 | 100 | 100 |
| Example 20b: 1C12-DHTA | 50 | 0 | 50 |
|  | 100 | 37 | 65 |
|  | 200 | 77 | 90 |
|  | 400 | 98 | 100 |
|  | 600 | 99 | 100 |

In this test none of the colloidal dispersions of the Examples matched the herbicidal performance of the commercial standard Roundup® Ultra.

Example 83

Substantially the same procedure as used in Example 72 is followed, except where noted below, in a greenhouse test by foliar application to two representative annual broadleaf species, wild radish (*Raphanus sativus*, RAPSN) and tall morningglory (*Ipomoea purpurea*, PHBPU), and a representative perennial narrowleaf species, quackgrass (*Elymus repens*, AGRRE). Soil is prefertilized with a 6-7-8 organic NPK fertilizer at a rate of 3.9 kg/m$^3$. Plants receive 16 hours of light per day. Temperatures are maintained at approximately 23° C. during the day and approximately 18° C. during the night. Relative humidity is maintained at approximately 70%. Only one set of 3 replicates is assigned to Roundup® Ultra in this test. Evaluation of herbicidal effectiveness is conducted about 21 DAT. The compositions included in this test are those of Examples 10a (comprising a salt of glyphosate prepared with N,N-distearyl tetraethylenepentamine), 18a (comprising a salt of glyphosate prepared with N-lauryl hexamethylenediamine), 20a (comprising a salt of glyphosate prepared with N-lauryl bis(hexamethylene)triamine), 47–50 (comprising salts of glyphosate prepared with cocoamide, palmamide, castoramide and oliveamide derivatives of triethylenetetramine respectively), 51–53 (comprising salts of glyphosate prepared with oliveamide, palmamide and castoramide derivatives of tetraethylenepentamine respectively), 59 and 60 (comprising salts of glyphosate prepared with palmamide and cocoamide derivatives of hexamethylenediamine respectively), and 62, 63 and 65 (comprising salts of glyphosate prepared with castoramide, cocoamide and soyamide derivatives of bis(hexamethylene)triamine respectively). Results of the test of Example 83 are given in Table 14 below.

TABLE 14

Herbicidal effectiveness data for Example 83

| Glyphosate composition | Glyphosate rate g a.e./ha | % Inhibition RAPSN | PHBPU | AGRRE |
|---|---|---|---|---|
| MON 0139 | 360 | 32 | 50 | 43 |
|  | 549 | 57 | 50 | 58 |
|  | 720 | 65 | 53 | 42 |
| Roundup ® Ultra | 360 | 85 | 42 | 67 |
|  | 540 | 95 | 68 | 78 |
|  | 720 | 95 | 63 | 83 |
| Example 10a: 2C18-TEPA | 360 | 28 | 45 | 22 |
|  | 540 | 43 | 38 | 22 |
|  | 720 | 38 | 45 | 33 |
| Example 18a: 1C12-HDA | 360 | 65 | 62 | 43 |
|  | 540 | 90 | 52 | 62 |
|  | 720 | 93 | 58 | 73 |
| Example 20a: 1C12-DHTA | 360 | 70 | 48 | 55 |
|  | 540 | 90 | 68 | 67 |
|  | 720 | 94 | 62 | 73 |
| Example 47: coco-CO-TETA | 360 | 70 | 43 | 45 |
|  | 540 | 63 | 55 | 53 |
|  | 720 | 83 | 78 | 65 |
| Example 48: palm-CO-TETA | 360 | 65 | 55 | 38 |
|  | 540 | 82 | 50 | 52 |
|  | 720 | 85 | 48 | 65 |
| Example 49: castor-CO-TETA | 360 | 55 | 58 | 47 |
|  | 540 | 63 | 50 | 60 |
|  | 720 | 90 | 60 | 60 |
| Example 50: olive-CO-TETA | 360 | 57 | 48 | 32 |
|  | 540 | 67 | 55 | 47 |
|  | 720 | 88 | 60 | 60 |
| Example 51: olive-CO-TEPA | 360 | 67 | 50 | 32 |
|  | 540 | 88 | 60 | 52 |
|  | 720 | 77 | 57 | 60 |
| Example 52: palm-CO-TEPA | 360 | 52 | 42 | 55 |
|  | 540 | 67 | 50 | 48 |
|  | 720 | 75 | 57 | 50 |
| Example 53: castor-CO-TEPA | 360 | 52 | 50 | 43 |
|  | 540 | 80 | 65 | 43 |
|  | 720 | 75 | 67 | 62 |
| Example 59: palm-CO-HDA | 360 | 95 | 58 | 62 |
|  | 540 | 96 | 63 | 68 |
|  | 720 | 95 | 75 | 73 |
| Example 60: coco-CO-HDA | 360 | 78 | 40 | 52 |
|  | 540 | 95 | 63 | 57 |
|  | 720 | 87 | 58 | 80 |
| Example 62: castor-CO-DHTA | 360 | 77 | 52 | 45 |
|  | 540 | 82 | 55 | 67 |
|  | 720 | 95 | 67 | 80 |
| Example 63: coco-CO-DHTA | 360 | 92 | 57 | 45 |
|  | 540 | 99 | 60 | 53 |
|  | 720 | 99 | 58 | 67 |
| Example 65: soy-CO-TEPA | 360 | 68 | 50 | 47 |
|  | 540 | 62 | 57 | 40 |
|  | 720 | 90 | 63 | 48 |

In this test the greatest herbicidal effectiveness on RAPSN was exhibited by the colloidal dispersions of Examples 59 and 63, and on PHBPU by those of Examples 47 and 59. On AGRRE, none of the compositions of the Examples matched the herbicidal performance of the commercial standard Roundup® Ultra.

Example 84

Substantially the same procedure as used in Example 83 is followed in a greenhouse test on RAPSN, PHBPU and AGRRE, except that an early evaluation of herbicidal effectiveness on RAPSN and PHBPU is conducted 5 DAT, as an indication of enhanced early symptom development, as well as a later evaluation on all three species conducted 22 DAT. The compositions included in this test are those of Examples 5 and 6 (comprising salts of glyphosate prepared with N-stearyl and N,N-distearyl triethylenetetramines respectively), 7 and 8a (comprising salts of glyphosate prepared with N-(n-octyl) and N-lauryl tetraethylenepentamines respectively), 11a–13a (comprising salts of glyphosate prepared with N-cocoalkyl, N-tallowalkyl and N-stearyl trimethylenediamines respectively), 14a and 15 (comprising salts of glyphosate prepared with N-tallowalkyl and N-cocoalkyl dipropylenetriamines respectively), and 19 and 20a (comprising salts of glyphosate prepared with N-(n-decyl) and N-lauryl bis(hexamethylene)triamines respectively). Results of the test of Example 84 are given in Table 15 below.

The composition of Example 20a also exhibited the greatest herbicidal effectiveness of all tested compositions on RAPSN.

Example 85

Substantially the same procedure as used in Example 83 is followed in a greenhouse test on RAPSN, PHBPU and AGRRE, except that an early evaluation of herbicidal effectiveness on RAPSN and PHBPU is conducted 9 DAT, as an indication of enhanced early symptom development, as well as a later evaluation on all three species conducted 17 DAT. The compositions included in this test are those of Examples 4 (comprising a salt of glyphosate prepared with N-lauryl triethylenetetramine), 9 (comprising a salt of glyphosate prepared with N-stearyl tetraethylenepentamine), 16 (comprising a salt of glyphosate prepared with N-lauryl butylenediamine), 22 (comprising a salt of glyphosate prepared with N-myristyl hexamethylenediamine), 32 and 33 (comprising salts of glyphosate prepared with n-decanamide and n-octanamide derivatives of tetraethylenepentamine respectively), and 43 (comprising a salt of glyphosate prepared with n-octanamide derivatives of bis(hexamethylene) triamine). Results of the test of Example 85 are given in Table 16 below.

TABLE 15

Herbicidal effectiveness data for Example 84

| Glyphosate composition | Glyphosate rate g a.e./ha | % Inhibition | | | | |
|---|---|---|---|---|---|---|
| | | 5 DAT | | 22 DAT | | |
| | | RAPSN | PHBPU | AGRRE | RAPSN | PHBPU |
| MON 0139 | 360 | 10 | 18 | 30 | 43 | 28 |
| | 540 | 10 | 15 | 32 | 55 | 35 |
| | 720 | 10 | 17 | 32 | 47 | 40 |
| Roundup ® Ultra | 360 | 17 | 20 | 73 | 67 | 47 |
| | 540 | 30 | 23 | 80 | 67 | 63 |
| | 720 | 23 | 38 | 95 | 75 | 88 |
| Example 5: | 360 | 15 | 10 | 10 | 50 | 25 |
| 1C18-TETA | 540 | 15 | 15 | 10 | 72 | 23 |
| | 720 | 15 | 15 | 10 | 55 | 30 |
| Example 6: | 360 | 15 | 15 | 5 | 38 | 27 |
| 2C18-TETA | 540 | 12 | 15 | 20 | 43 | 33 |
| | 720 | 15 | 15 | 28 | 58 | 32 |
| Example 7: | 360 | 17 | 15 | 33 | 33 | 38 |
| 1C8-TEPA | 540 | 10 | 15 | 20 | 45 | 55 |
| | 720 | 15 | 15 | 20 | 53 | 65 |
| Example 8a: | 360 | 15 | 15 | 30 | 62 | 38 |
| 1C12-TEPA | 540 | 15 | 15 | 18 | 47 | 58 |
| | 720 | 17 | 15 | 40 | 52 | 47 |
| Example 11a: | 360 | 13 | 15 | 20 | 38 | 32 |
| coco-TDA | 540 | 15 | 15 | 47 | 52 | 38 |
| | 720 | 15 | 15 | 50 | 57 | 68 |
| Example 12a: | 360 | 15 | 15 | 50 | 45 | 27 |
| tallow-TDA | 540 | 15 | 15 | 28 | 68 | 57 |
| | 720 | 15 | 15 | 52 | 53 | 63 |
| Example 13a: | 360 | 12 | 15 | 20 | 53 | 58 |
| 1C18-TDA | 540 | 17 | 15 | 20 | 58 | 40 |
| | 720 | 15 | 15 | 30 | 58 | 58 |
| Example 14a: | 360 | 15 | 17 | 20 | 55 | 45 |
| tallow-DPTA | 540 | 13 | 15 | 25 | 58 | 50 |
| | 720 | 23 | 15 | 30 | 55 | 40 |
| Example 15: | 360 | 15 | 15 | 18 | 58 | 22 |
| coco-DPTA | 540 | 15 | 17 | 27 | 57 | 30 |
| | 720 | 15 | 15 | 15 | 55 | 50 |
| Example 19: | 360 | 15 | 15 | 57 | 57 | 30 |
| 1C10-DHTA | 540 | 20 | 15 | 87 | 65 | 47 |
| | 720 | 17 | 17 | 82 | 73 | 57 |
| Example 20a: | 360 | 18 | 15 | 62 | 67 | 47 |
| 1C12-DHTA | 540 | 32 | 15 | 98 | 75 | 38 |
| | 720 | 17 | 15 | 80 | 82 | 70 |

In this test only the colloidal dispersions of Examples 19 and 20a came close to matching the herbicidal performance of the commercial standard Roundup® Ultra on AGRRE.

TABLE 16

Herbicidal effectiveness data for Example 35

| Glyphosate composition | Glyphosate rate g a.e./ha | % Inhibition | | | | |
|---|---|---|---|---|---|---|
| | | 9 DAT | | 17 DAT | | |
| | | RAPSN | PHBPU | AGRRE | RAPSN | PHBPU |
| MON 0139 | 360 | 20 | 15 | 18 | 43 | 37 |
| | 540 | 30 | 17 | 28 | 63 | 37 |
| | 720 | 20 | 15 | 37 | 60 | 42 |
| Roundup ® Ultra | 360 | 28 | 18 | 70 | 67 | 45 |
| | 540 | 67 | 38 | 83 | 80 | 72 |
| | 720 | 42 | 18 | 90 | 77 | 53 |
| Example 4: 1C12-TETA | 360 | 40 | 12 | 18 | 67 | 32 |
| | 540 | 47 | 15 | 23 | 73 | 37 |
| | 720 | 30 | 23 | 28 | 68 | 37 |
| Example 9: 1C18-TEPA | 360 | 22 | 12 | 15 | 52 | 23 |
| | 540 | 40 | 15 | 15 | 65 | 27 |
| | 720 | 63 | 17 | 20 | 78 | 32 |
| Example 16: 1C12-BDA | 360 | 40 | 17 | 55 | 70 | 35 |
| | 540 | 58 | 20 | 52 | 78 | 30 |
| | 720 | 58 | 17 | 62 | 73 | 35 |
| Example 22: 1C14-HDA | 360 | 43 | 48 | 53 | 73 | 60 |
| | 540 | 40 | 45 | 70 | 70 | 58 |
| | 720 | 45 | 30 | 72 | 77 | 68 |
| Example 32: 1.2C9-CO-TEPA | 360 | 28 | 17 | 45 | 53 | 37 |
| | 540 | 35 | 15 | 75 | 67 | 35 |
| | 720 | 38 | 15 | 68 | 68 | 55 |
| Example 33: 1C7-CO-TEPA | 360 | 30 | 15 | 33 | 53 | 30 |
| | 540 | 25 | no data | 43 | 60 | 38 |
| | 720 | 28 | 22 | 55 | 57 | 43 |
| Example 43: 1.2C7-CO-DHTA | 360 | 25 | 15 | 17 | 50 | 35 |
| | 540 | 40 | 15 | 20 | 57 | 30 |
| | 720 | 45 | 17 | 18 | 68 | 33 |

In this test none of the colloidal dispersions of the Examples matched the herbicidal performance of the commercial standard Roundup® Ultra.

Example 86

Substantially the same procedure as used in Example 83 is followed followed in a greenhouse test on RAPSN, PHBPU and AGRRE. Two sets of Roundup® Ultra treatments were included. Evaluation of herbicidal effectiveness is conducted about 21 DAT. The compositions included in this test are those of Examples 10a (comprising a salt of glyphosate prepared with N,N-distearyl tetraethylenepentamine), 18a (comprising a salt of glyphosate prepared with N-lauryl hexamethylenediamine), 25 (comprising a salt of glyphosate prepared with oleamide derivatives of diethylenetriamine), 26–31a (comprising salts of glyphosate prepared with n-decanamide, di(n-decanamide), dilauramide, stearamide (1.2 moles), stearamide (1.5 moles) and oleamide derivatives of triethylenetetramine respectively), and 34–39 and 41 (comprising salts of glyphosate prepared with n-decanamide, di(n-decanamide), lauramide, dilauramide, oleamide (1.2 moles), oleamide (1.5 moles) and dioleamide derivatives of tetraethylenepentamine respectively). Results of the test of Example 86 are given in Table 17 below.

TABLE 17

Herbicidal effectiveness data for Example 86

| Glyphosate composition | Glyphosate rate g a.e./ha | % Inhibition | | |
|---|---|---|---|---|
| | | RAPSN | PHBPU | AGRRE |
| MON 0139 | 360 | 33 | 30 | 33 |
| | 540 | 32 | 70 | 43 |
| | 720 | 50 | 65 | 65 |
| Roundup ® Ultra (first set) | 360 | 50 | 78 | 63 |
| | 540 | 42 | 93 | 65 |
| | 720 | 53 | 96 | 80 |
| Roundup ® Ultra (second set) | 360 | 43 | 72 | 20 |
| | 540 | 45 | 100 | 42 |
| | 720 | 45 | 99 | 43 |
| Example 10a: 2C18-TEPA | 360 | 30 | 37 | 15 |
| | 540 | 37 | 72 | 22 |
| | 720 | 42 | 48 | 33 |
| Example 18a: 1C12-HDA | 360 | 42 | 87 | 45 |
| | 540 | 57 | 87 | 60 |
| | 720 | 63 | 93 | 63 |
| Example 25: 1.2C17 = CO-DETA | 360 | 58 | 80 | 55 |
| | 540 | 48 | 98 | 73 |
| | 720 | 72 | 99 | 75 |
| Example 26: 1.2C9-CO-TETA | 360 | 38 | 75 | 28 |
| | 540 | 48 | 78 | 58 |
| | 720 | 43 | 73 | 70 |
| Example 27: 2C9-CO-TETA | 360 | 50 | 77 | 63 |
| | 540 | 63 | 80 | 67 |
| | 720 | 60 | 93 | 68 |
| Example 28: 2C11-CO-TETA | 360 | 45 | 77 | 50 |
| | 540 | 57 | 99 | 43 |
| | 720 | 67 | 88 | 68 |
| Example 29: 1.2C17-CO-TETA | 360 | 27 | 37 | 42 |
| | 540 | 30 | 72 | 18 |
| | 720 | 32 | 48 | 22 |
| Example 30: | 360 | 38 | 50 | 22 |

TABLE 17-continued

Herbicidal effectiveness data for Example 86

| Glyphosate composition | Glyphosate rate g a.e./ha | % Inhibition RAPSN | PHBPU | AGRRE |
|---|---|---|---|---|
| 1.5C17-CO-TETA | 540 | 35 | 58 | 23 |
|  | 720 | 40 | 63 | 13 |
| Example 31a: 1.2C17= CO-TETA | 360 | 57 | 94 | 42 |
|  | 540 | 57 | 93 | 40 |
|  | 720 | 58 | 100 | 62 |
| Example 34: 1.5C9-CO-TEPA | 360 | 55 | 60 | 42 |
|  | 540 | 55 | 65 | 50 |
|  | 720 | 63 | 78 | 70 |
| Example 35: 2C9-CO-TEPA | 360 | 45 | 67 | 48 |
|  | 540 | 52 | 73 | 65 |
|  | 720 | 48 | 68 | 63 |
| Example 36: 1.2C11-CO-TEPA | 360 | 37 | 65 | 32 |
|  | 540 | 52 | 75 | 52 |
|  | 720 | 55 | 80 | 65 |
| Example 37: 2C11-CO-TEPA | 360 | 53 | 60 | 37 |
|  | 540 | 53 | 84 | 33 |
|  | 720 | 55 | 92 | 80 |
| Example 38: 1.2C17= CO-TEPA | 360 | 47 | 65 | 38 |
|  | 540 | 60 | 99 | 43 |
|  | 720 | 52 | 85 | 47 |
| Example 39: 1.5C17= CO-TEPA | 360 | 60 | 88 | 48 |
|  | 540 | 57 | 94 | 50 |
|  | 720 | 68 | 99 | 63 |
| Example 41: 2C17= CO-TEPA | 360 | 55 | 93 | 33 |
|  | 540 | 60 | 99 | 55 |
|  | 720 | 73 | 100 | 53 |

In this test there was a significant discrepancy in the results on AGRRE for the two sets of Roundup® Ultra treatments, and it is suggested that the data for this species be disregarded. Herbicidal performance on both RAPSN and PHBPU obtained with the colloidal dispersions of Examples 18a, 25, 31a, 39 and 41 substantially equalled or exceeded that obtained with the commercial standard Roundup® Ultra.

Example 87

Substantially the same procedure as used in Example 83 is followed followed in a greenhouse test on RAPSN, PHBPU and AGRRE. Two sets of Roundup® Ultra treatments were included. Evaluation of herbicidal effectiveness is conducted about 21 DAT. The compositions included in this test are those of Examples 17 (comprising a salt of glyphosate prepared with N-stearyl butylenediamine), 21 (comprising a salt of glyphosate prepared with N,N-dilauryl triethylenetetramine), 22 (comprising a salt of glyphosate prepared with N-myristyl hexamethylenediamine), 23 (comprising a salt of glyphosate prepared with an N-(n-octenyl)succinimide derivative of hexamethylenediamine), 40 and 42 (comprising stearamide (1.5 moles) and distearamide derivatives of tetraethylenepentamine respectively), and 44 and 45 (comprising salts of glyphosate prepared with distearamide and dioleamide and dioleamide derivatives of triethylenetetramine respectively). Results of the test of Example 87 are given in Table 18 below.

TABLE 18

Herbicidal effectiveness data for Example 87

| Glyphosate composition | Glyphosate rate g a.e./ha | % Inhibition RAPSN | PHBPU | AGRRE |
|---|---|---|---|---|
| MON 0139 | 360 | 48 | 43 | 53 |
|  | 540 | 57 | 47 | 57 |
|  | 720 | 78 | 57 | 65 |
| Roundup ® Ultra (first set) | 360 | 58 | 58 | 78 |
|  | 540 | 95 | 58 | 88 |
|  | 720 | 83 | 65 | 97 |
| Roundup ® Ultra (second set) | 360 | 77 | 57 | 47 |
|  | 540 | 78 | 53 | 70 |
|  | 720 | 87 | 55 | 67 |
| Example 17: 1C18-BDA | 360 | 43 | 35 | 42 |
|  | 540 | 40 | 45 | 42 |
|  | 720 | 35 | 50 | 53 |
| Example 21: 2C12-TETA | 360 | 63 | 55 | 53 |
|  | 540 | 68 | 75 | 67 |
|  | 720 | 70 | 72 | 75 |
| Example 22: 1C14-HDA | 360 | 88 | 63 | 78 |
|  | 540 | 92 | 78 | 88 |
|  | 720 | 88 | 80 | 95 |
| Example 23: 1C8= S-HDA | 360 | 89 | 62 | 87 |
|  | 540 | 83 | 73 | 99 |
|  | 720 | 82 | 82 | 96 |
| Example 40: 1.5C17-CO-TEPA | 360 | 65 | 50 | 48 |
|  | 540 | 75 | 50 | 53 |
|  | 720 | 68 | 53 | 60 |
| Example 42: 2C17-CO-TEPA | 360 | 55 | 45 | 30 |
|  | 540 | 48 | 28 | 32 |
|  | 720 | 38 | 35 | 37 |
| Example 44: 2C17-CO-TETA | 360 | 53 | 42 | 42 |
|  | 540 | 65 | 48 | 40 |
|  | 720 | 60 | 47 | 52 |
| Example 45: 2C17= CO-TETA | 360 | 75 | 70 | 67 |
|  | 540 | 87 | 82 | 70 |
|  | 720 | 99 | 83 | 83 |

As in the test of Example 86, there was a significant discrepancy in the results on AGRRE for the two sets of Roundup® Ultra treatments, and it is suggested that the data for this species be disregarded. Herbicidal performance on both RAPSN and PHBPU obtained with the colloidal dispersions of Examples 22, 23 and 45 substantially equalled or exceeded that obtained with the commercial standard Roundup® Ultra.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A plant treatment composition for application to foliage of a plant, comprising an aqueous application medium wherein are colloidally dispersed supramolecular aggregates comprising one or more amphiphilic salt(s) having anions of an anionic exogenous chemical substance and cations derived by protonation of one or more polyamine derivative (s), each such polyamine derivative having a number n not less than 1 of amino groups that can be protonated to form cationic primary, secondary or tertiary ammonium groups, and being of formula II:

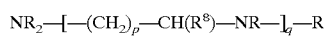

$$NR_2-[-(CH_2)_p-CH(R^8)-NR-]_q-R \qquad \text{II}$$

wherein $R^8$ is hydrogen or a $C_{1-6}$ alkyl group, p is an integer from 1 to about 5 q is an integer from 1 to about 10, and each R is independently hydrogen, a $C_{1-6}$ alkyl group, or a group —L—R' wherein R' is a saturated or unsaturated fatty hydrocarbyl chain and L is a bonding function, provided that at least one R is such a group —L—R'; said bonding function L being selected from
(a) a carbonyl bridge between the R' group and a nitrogen atom, and
(b) a succinyl bridge between the R' group and a nitrogen atom forming, with the nitrogen atom from which an attached R group is dropped, a succinimidyl function;
said composition containing
(i) a molar amount X in total of said exogenous chemical substance, in all salt and acid forms thereof present, sufficient to elicit a biological response when the composition is applied to the foliage of the plant at a rate of about 10 to about 1000 l/ha,
(ii) a molar amount A in total of said polyamine derivative(s) and cations derived therefrom, and
(iii) a zero or molar amount B in total of one or more monovalent base(s) and cations derived therefrom, said base(s) being other than a polyamine or derivative thereof, such that nA/(nA+B) is about 0.01 to 1, and (nA+B)/X is about 0.5 to about 10.

2. The composition of claim 1 wherein n is not less than 2, and wherein more than one of the amino groups in the polyamine derivative are, when formulated in the composition with the exogenous chemical substance, in the form of cationic primary, secondary or tertiary ammonium groups.

3. The composition of claim 1 wherein (nA+B)/X is about 0.5 to about 5.

4. The composition of claim 1 wherein (nA+B)/X is about 0.5 to about 2.

5. The composition of claim 1 wherein, in formula II, p is 1 to 5, $R^8$ is hydrogen except where p is 1 in which case $R^8$ is hydrogen or a methyl group, q is 1 to 4, and bonding functions L are all carbonyl bridges.

6. The composition of claim 5 wherein only one R group is a group —L—R' and all other R groups are hydrogen, said group —L—R' having 8 to 18 carbon atoms.

7. The composition of claim 1 wherein said monovalent base(s) produce alkali metal cations, ammonium cations, or organic ammonium or sulfonium cations having in total 1–6 carbon atoms.

8. The composition of claim 7 wherein said cations are sodium, ammonium, dimethylammonium, isopropylammonium, monoethanolammonium or trimethylsulfonium cations.

9. The composition of claim 1 wherein the exogenous chemical substance is a nematicide selected from 3,4,4-trifluoro-3-butenoic acid and N-(3,4,4-trifluoro-1-oxo-3-butenyl)glycine.

10. The composition of claim 1 wherein the exogenous chemical substance is a herbicide.

11. The composition of claim 10 wherein the herbicide is selected from acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, glyphosate, haloxyfop, imazameth, imazethabenz, imazamox, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr.

12. The composition of claim 10 wherein the herbicide is an imidazolinone herbicide.

13. The composition of claim 10 wherein the herbicide is selected from N-phosphonomethylglycine and DL-homoalanin-4-yl(methyl)phosphinate.

14. The composition of claim 1 wherein nA/(nA+B) is about 0.01 to about 0.2.

15. The composition of claim 1 wherein nA/(nA+B) is about 0.1 to 1.

16. The composition of claim 1, further comprising an adjuvant amount of an amphiphilic quaternary ammonium compound, or mixture of such compounds, each having formula VIII:

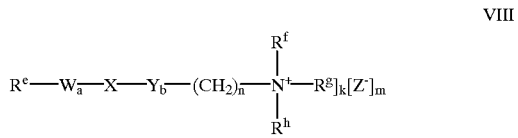

wherein $R^e$ is a hydrocarbyl or haloalkyl group having about 6 to about 22 carbon atoms; W and Y are independently O or NH; a and b are independently 0 or 1 but at least one of a and b is 1; X is CO, SO or $SO_2$; n is 2 to 4; $R^f$, $R_g$ and $R^h$ are independently $C_{1-4}$ alkyl; $Z^-$ is a suitable anion; and k and m are integers such that positive electrical charges on cations balance negative electrical charges on anions.

17. The composition of claim 16 wherein, in the formula for said amphiphilic quaternary ammonium compound or mixture of such compounds, $R^e$ is a saturated perfluoroalkyl group having about 6 to about 12 carbon atoms, X is $SO_2$, Y is NH, a is 0, b is 1, n is 3, $R^f$, $R^g$ and $R^h$ are methyl groups, k and m are each 1, and $Z^-$ is a chloride, bromide or iodide anion.

18. The composition of claim 1, further comprising an adjuvant amount of an oil or mixture of oils.

19. The composition of claim 18 wherein said oil(s) are selected from triglyceride esters of fatty acids of animal, vegetable or synthetic origin, paraffins, polysiloxanes, fatty acids and esters and amides thereof.

20. The composition of claim 18 wherein said oil(s) are triglyceride esters of fatty acids of animal, vegetable or synthetic origin.

21. The composition of claim 18 wherein said oil(s) each have a chemical structure corresponding to formula IX:

where $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and Y is O or NH.

22. The composition of claim 21 wherein said oil(s) are selected from methyl oleate, ethyl oleate, isopropyl myristate, isopropyl palmitate and butyl stearate.

23. A process for eliciting a biological activity in a plant or in a pathogen, parasite or feeding organism present in or on a plant, comprising a step of applying to foliage of the plant a biologically effective amount of a plant treatment composition of any of claims 1 to 22.

24. A liquid concentrate composition that comprises about 5% to about 50% by weight of an anionic exogenous chemical substance expressed as acid equivalent, and that when diluted with a suitable amount of water forms a plant treatment composition of claim 1.

25. An aqueous concentrate composition that comprises about 5% to about 50% by weight of an anionic exogenous chemical substance expressed as acid equivalent, and that when diluted with a suitable amount of water forms a plant treatment composition of claim 1.

26. A herbicidal composition for application to foliage of a plant, comprising an aqueous application medium wherein are colloidally dispersed supramolecular aggregates comprising one or more amphiphilic salt(s) having anions of N-phosphonomethylglycine and cations derived by protonation of one or more polyamine derivative(s), each such polyamine derivative having a number n not less than 1 of amino groups that can be protonated to form cationic primary, secondary or tertiary ammonium groups, and being of formula II:

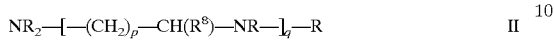      II wherein $R^8$ is hydrogen or a $C_{1-6}$ alkyl group, p is an integer from 1 to about 5, q is an integer from 1 to about 10, and each R is independently hydrogen, a $C_{1-6}$ alkyl group, or a group —L—R' wherein R' is a saturated or unsaturated fatty hydrocarbyl chain and L is a bonding function, provided that at least one R is such a group —L—R'; said bonding function L being selected from (a) a carbonyl bridge between the R' group and a nitrogen atom, and (b) a succinyl bridge between the R' group and a nitrogen atom forming, with the nitrogen atom from which an attached R group is dropped, a succinimidyl function;

said composition containing (i) a molar amount X in total of said exogenous chemical substance, in all salt and acid forms thereof present, sufficient to elicit a biological response when the composition is applied to the foliage of the plant at a rate of about 10 to about 1000 l/ha, (ii) a molar amount A in total of said polyamine derivative(s) and cations derived therefrom, and (iii) a zero or molar amount B in total of one or more monovalent base(s) and cations derived therefrom, said base(s) being other than a polyamine or derivative thereof, such that nA/(nA+B) is about 0.01 to 1, and (nA+B)/X is about 0.5 to about 10.

27. The composition of claim 26 wherein (nA+B)/X is about 0.5 to about 5.

28. The composition of claim 26 wherein (nA+B)/X is about 0.5 to about 2.

29. The composition of claim 26 wherein nA/(nA+B) is about 0.01 to about 0.2.

30. The composition of claim 26 wherein nA/(nA+B) is about 0.1 to 1.

31. The composition of claim 26, further comprising an adjuvant amount of an amphiphilic quaternary ammonium compound, or mixture of such compounds, each having is formula VIII:

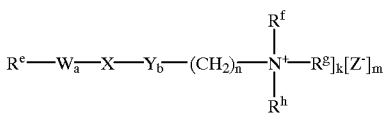      VIII wherein $R^e$ is a hydrocarbyl or haloalkyl group having about 6 to about 22 carbon atoms; W and Y are independently O or NH; a and b are independently 0 or 1 but at least one of a and b is 1; X is CO, SO or $SO_2$; n is 2 to 4; $R^f$, $R^g$ and $R^h$ are independently $C_{1-4}$ alkyl; $Z^-$ is a suitable anion; and k and m are integers such that positive electrical charges on cations balance negative electrical charges on anions.

32. The composition of claim 31 wherein, in the formula for said amphiphilic quaternary ammonium compound or mixture of such compounds, $R^e$ is a saturated perfluoroalkyl group having about 6 to about 12 carbon atoms, X is $SO_2$, Y is NH, a is 0, b is 1, n is 3, $R^f$, $R^g$ and $R^h$ are methyl groups, k and m are each 1, and $Z^-$ is a chloride, bromide or iodide anion.

33. The composition of claim 26, further comprising an adjuvant amount of an oil or mixture of oils.

34. The composition of claim 33 wherein said oil(s) are selected from triglyceride esters of fatty acids of animal, vegetable or synthetic origin, paraffins, polysiloxanes, fatty acids and esters and amides thereof.

35. The composition of claim 33 wherein said oil(s) are triglyceride esters of fatty acids of animal, vegetable or synthetic origin.

36. The composition of claim 33 wherein said oil(s) each have a chemical structure corresponding to formula IX:

      IX wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and Y is O or NH.

37. The composition of claim 36 wherein said oil(s) are selected from methyl oleate, ethyl oleate, isopropyl myristate, isopropyl palmitate and butyl stearate.

38. An aqueous concentrate composition that comprises about 5% to about 50% by weight of N-phosphonomethylglycine expressed as acid equivalent, and that when diluted with a suitable amount of water forms a herbicidal composition of claim 26.

39. A process for killing or controlling undesired plants comprising a step of applying to foliage of the plants a herbicidally effective amount of a herbicidal composition of any of claims 26 to 37.

* * * * *